(12) United States Patent
Mickle et al.

(10) Patent No.: US 7,223,735 B2
(45) Date of Patent: May 29, 2007

(54) ABUSE RESISTANT LYSINE AMPHETAMINE COMPOUNDS

(75) Inventors: Travis Mickle, Charlottesville, VA (US); Suma Krishnan, Blacksburg, VA (US); James Scott Moncrief, Blacksburg, VA (US); Christopher Lauderback, Blacksburg, VA (US); Barney Bishop, Annandale, VA (US); Rob Oberlender, Blacksburg, VA (US); Thomas Piccariello, Blacksburg, VA (US)

(73) Assignee: New River Pharmaceuticals Inc., Radford, VA (US)

( * ) Notice: Subject to any disclaimer, the term of this patent is extended or adjusted under 35 U.S.C. 154(b) by 127 days.

(21) Appl. No.: 10/857,619

(22) Filed: Jun. 1, 2004

(65) Prior Publication Data

US 2005/0038121 A1 Feb. 17, 2005

Related U.S. Application Data

(60) Provisional application No. 60/567,801, filed on May 5, 2004, provisional application No. 60/473,929, filed on May 29, 2003.

(51) Int. Cl.
*A61K 38/00* (2006.01)
(52) U.S. Cl. .......................... 514/18; 514/12; 424/1.69
(58) Field of Classification Search .................. 514/18
See application file for complete search history.

(56) References Cited

U.S. PATENT DOCUMENTS

| | | | |
|---|---|---|---|
| 3,028,395 A | 4/1962 | Gillingham | |
| 3,028,430 A | 4/1962 | Gillingham | |
| 3,676,492 A | 7/1972 | Biel et al. | |
| 3,706,831 A | 12/1972 | Plotnikoff et al. | |
| 3,843,696 A | 10/1974 | Wagner et al. | |
| 3,846,399 A | 11/1974 | Hirschmann et al. | |
| 3,878,187 A | 4/1975 | Schneider et al. | |
| 3,884,898 A | 5/1975 | Schneider | |
| 3,975,342 A | 8/1976 | Gross | |
| 3,998,799 A | 12/1976 | Bodor et al. | |
| 4,000,280 A | 12/1976 | Florvall et al. | |
| 4,025,501 A | 5/1977 | Leute | |
| 4,040,907 A | 8/1977 | Ullman et al. | |
| 4,043,989 A | 8/1977 | Schneider et al. | |
| 4,064,235 A | 12/1977 | Yanaihera et al. | |
| 4,064,236 A | 12/1977 | Dorn et al. | |
| 4,297,346 A | 10/1981 | Rips et al. | |
| 4,356,166 A | 10/1982 | Peterson et al. | |
| 4,399,121 A | 8/1983 | Albarella et al. | |
| 4,427,660 A | 1/1984 | Schiffman et al. | |
| 4,457,907 A | 7/1984 | Porter | |
| 4,552,864 A | 11/1985 | Antoni et al. | |
| 4,650,675 A | 3/1987 | Borel et al. | |
| 4,801,575 A | 1/1989 | Pardridge | |
| 4,863,735 A | 9/1989 | Kohn et al. | |
| 4,902,505 A | 2/1990 | Pardridge et al. | |
| 4,960,790 A | 10/1990 | Stella et al. | |
| 4,976,962 A | 12/1990 | Bichon et al. | |
| 5,026,827 A | 6/1991 | Miyazaki | |
| 5,073,641 A | 12/1991 | Bundgaard et al. | |
| 5,087,616 A | 2/1992 | Myers et al. | |
| 5,169,933 A | 12/1992 | Anderson et al. | |
| 5,183,883 A | 2/1993 | Tanaka et al. | |
| 5,219,564 A | 6/1993 | Zalipsky et al. | |
| 5,233,025 A | 8/1993 | Miyazaki et al. | |
| 5,238,714 A | 8/1993 | Wallace et al. | |
| 5,362,831 A | 11/1994 | Mongelli et al. | |
| 5,470,997 A | 11/1995 | Buechler et al. | |
| 5,501,987 A | 3/1996 | Ordonez et al. | |
| 5,529,915 A | 6/1996 | Phillips et al. | |
| 5,534,496 A | 7/1996 | Lee et al. | |
| 5,670,477 A | 9/1997 | Poduslo et al. | |
| 5,762,909 A | 6/1998 | Uzgiris | |
| 5,767,227 A | 6/1998 | Latham et al. | |
| 5,846,743 A | 12/1998 | Janmey et al. | |

(Continued)

FOREIGN PATENT DOCUMENTS

AU          54168/65          1/1965

(Continued)

OTHER PUBLICATIONS

Aggarwal, et al., "Synthesis and Biological Evaluation of Prodrugs of Zidovudine," *J. Med. Chem.*, 33(5):1505-1511 (1990).

(Continued)

*Primary Examiner*—Cecilia J. Tsang
*Assistant Examiner*—Maury Audet
(74) *Attorney, Agent, or Firm*—Hunton & Williams LLP

(57) ABSTRACT

The present invention describes compounds, compositions and methods of using the same comprising lysine covalently attached to amphetamine. These compounds and compositions are useful for reducing or preventing abuse and overdose of amphetamine. These compounds and compositions find particular use in providing an abuse-resistant alternative treatment for certain disorders, such as attention deficit hyperactivity disorder (ADHD), ADD, narcolepsy, and obesity. Oral bioavailability of amphetamine is maintained at therapeutically useful doses. At higher doses bioavailability is substantially reduced, thereby providing a method of reducing oral abuse liability. Further, compounds and compositions of the invention decrease the bioavailability of amphetamine by parenteral routes, such as intravenous or intranasal administration, further limiting their abuse liability.

18 Claims, 55 Drawing Sheets

U.S. PATENT DOCUMENTS

| | | | |
|---|---|---|---|
| 5,851,536 A | 12/1998 | Yager et al. | |
| 5,882,645 A | 3/1999 | Toth et al. | |
| 5,891,459 A | 4/1999 | Cooke et al. | |
| 5,898,033 A | 4/1999 | Swadesh et al. | |
| 5,910,569 A | 6/1999 | Latham et al. | |
| 5,935,988 A | 8/1999 | Matzke et al. | |
| 5,948,750 A | 9/1999 | Garsky et al. | |
| 5,952,294 A | 9/1999 | Lazo et al. | |
| 5,977,163 A | 11/1999 | Li et al. | |
| 6,005,004 A | 12/1999 | Katz et al. | |
| 6,030,941 A | 2/2000 | Summerton et al. | |
| 6,043,230 A | 3/2000 | Arimilli et al. | |
| 6,048,736 A | 4/2000 | Kosak | |
| 6,074,659 A | 6/2000 | Kunz et al. | |
| 6,093,391 A | 7/2000 | Kabanov et al. | |
| 6,235,718 B1 | 5/2001 | Balasubramanium | |
| 6,255,285 B1 | 7/2001 | Kotake | |
| 6,258,836 B1 | 7/2001 | Shashoua | |
| 6,306,993 B1 | 10/2001 | Rothbard et al. | |
| 6,309,633 B1 | 10/2001 | Ekwuribe et al. | |
| 6,407,137 B2 | 6/2002 | Shashoua | |
| 6,458,842 B1 | 10/2002 | Dickinson et al. | |
| 6,632,922 B1 | 10/2003 | Deming et al. | |
| 6,680,365 B1 | 1/2004 | Deming et al. | |
| 6,686,446 B2 | 2/2004 | Deming et al. | |
| 6,716,452 B1 | 4/2004 | Piccariello et al. | |
| 6,740,641 B2 | 5/2004 | Gao | |
| 6,784,186 B1 | 8/2004 | Jackson | |
| 6,913,768 B2 | 7/2005 | Couch et al. | |
| 7,105,486 B2 * | 9/2006 | Mickle et al. | 514/12 |
| 2001/0031873 A1 | 10/2001 | Greenwald et al. | |
| 2002/0098999 A1 | 7/2002 | Gallop et al. | |
| 2002/0099013 A1 | 7/2002 | Piccariello et al. | |
| 2002/0115725 A1 * | 8/2002 | Epstein et al. | 514/649 |
| 2002/0151526 A1 | 10/2002 | Gallop et al. | |
| 2002/0151529 A1 | 10/2002 | Cundy et al. | |
| 2002/0173468 A1 | 11/2002 | Lerchen et al. | |
| 2002/0183390 A1 | 12/2002 | Javitt | |
| 2003/0077297 A1 | 4/2003 | Chen et al. | |
| 2004/0131680 A1 | 7/2004 | Goldenheim et al. | |
| 2004/0132968 A1 | 7/2004 | Reed et al. | |
| 2004/0204434 A1 | 10/2004 | Shafer | |
| 2005/0038121 A1 | 2/2005 | Mickle et al. | |
| 2005/0054561 A1 | 3/2005 | Mickle et al. | |

FOREIGN PATENT DOCUMENTS

| | | | |
|---|---|---|---|
| EP | 0 187 547 A2 | | 7/1987 |
| EP | 0634999 | | 10/1993 |
| FR | 1421130 | | 1/1965 |
| GB | 1092089 | | 11/1967 |
| GB | 1112347 | | 5/1968 |
| JP | 55007242 | | 1/1980 |
| JP | 55028915 | | 2/1980 |
| JP | 4112858 | | 4/1992 |
| JP | 7165684 | | 6/1995 |
| NL | 6414901 | * | 12/1964 |
| WO | WO 93/20048 | | 10/1993 |
| WO | WO 95/12605 | | 5/1995 |
| WO | WO 95/14033 | | 5/1995 |
| WO | WO 97/36616 | | 10/1997 |
| WO | WO 98/04277 | | 2/1998 |
| WO | WO 98/48824 | | 11/1998 |
| WO | WO 02/34237 A1 | | 5/2002 |
| WO | WO 03/03498 | | 5/2003 |

OTHER PUBLICATIONS

Amidon, G., et al., "A Theoretical Basis for a Biopharmaceutic Drug Classification: The Correlation of *in Vitro* Drug Product Dissolution and *in Vivo* Bioavailability," *Pharmaceutical Research*, vol. 12, No. 3 (1995).

Amidon, G.L., et al., "5'-Amino Acid Esters of Antiviral Nucleosides, Acyclovir, and AZT are Absorbed by the Intestinal PEPT1 Peptide Transporter," *Pharm Res*, 16(2):175 (1999), Abstract.

Balimane, P., et al., "Effect of Ionization on the Variable Uptake of Valacyclovir via the Human Intestinal Peptide Transporter (hPepT1) in CHP cells," *Biopharm Drug Dispos*, 21(5):165-174 (2000), Abstract.

Balimane, P.V., et al., "Direct Evidence for Peptide Transporter (PepT1)-Mediated Uptake of a Nonpeptide Prodrug, Valacyclovir," *Biochem Biophys Res Commun*, 250(2):246-251 (1998), Abstract.

Bunevicius, R., "Effects of Thyroxine as Compared with Thyroxine Plus Triiodothyronine in Patients with Hypothyroidism," *The New England Journal of Medicine*, vol. 340, No. 6 (1999).

Burnettem, Thimysta C., et al., "Metabolic Disposition of the Acyclovir Prodrug Valaciclovir in the Rat," *Drug Metabolism and Disposition*, 22(1):60-64 (1994).

Canaris, G., "The Colorado Thyroid Disease Prevalence Study," *Archives Internal Medicine Articles and Abstracts*, vol. 160, No. 4 (2000).

De Vrueh, Remco L.A., et al, "Transport of L-Valine-Acyclovir Via the Oligopeptide Transporter in the Human Intestinal Cell Line, Caco-2," *Journal of Pharmacology and Experimental Therapeutics*, 286(2):1166-1170 (1988).

Friedrichsen, G.M., et al., "Model Prodrugs Designed for the Intestinal Peptide Transporter. A Synthetic Approach for Coupling of Hydroxy-Containing Compounds to Dipeptides," *Eur J Pharm Sci*, 14(1):13-19 (2001, Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448-454 (1999), Abstract.

Han H., et al., "5'-Amino Acid Esters of Antiviral Nucleosides, Acyclovir, and AZT and Absorbed by the Intestinal PEPT1 Peotide Transporter," *Pharm Res*, 15(8):1154-1159 (1998), Abstract.

Han, H.K., et al., "Cellular Uptake Mechanism of Amino Acid Ester prodrugs in Caco-2hPEPT1 Cells Overexpressing a Human Peptide Transporter," *Pharm Res*, 15(9):1382-1386 (1998), Abstract.

Han, Hyo-Kyung, et al., "Targeted Prodrug Design to Optimize Drug Delivery," *AAPS PharmSci*, 2(1): Article 6 (2000).

Havranova, Marie et al., "A High-Molecular Mass Derivative of Trypsin-Kallikrein Inhibitor for Potential Medical Use, II," *Hoppe-Seyler's Z. Physiol. Chem.*, 363:295-303 (1982).

Herrera-Ruiz, D., et al., "Spatial Expression Patterns of Peptide Transporters in the Human and Rat Gastrointestinal Tracts, Caco-2 in vitro Cell Culture Model, and Multiple Human Tissues," *AAPS PharmSci*, 3(1):E9 (2001), Abstract.

Hosztafi, S. et al. "Synthesis and Analgetic Activity of Nicotinic Esters of Morphine Derivatives," Arzneim.-Forsch./Drug Res. 43(II), Nr. 11 (1993).

International Search Report, dated Oct. 9, 2003, for PCT/US03/05525.

International Search Report, dated Sep. 3, 2003.

Knutter, I, et al., "A Novel Inhibitor of the Mammalian Peptide Transporter PEPT1," *Biochemistry*, 40(14):4454-4458 (2001), Abstract.

Kovacs, J., et al., "Glutamic and Aspartic Anhydrides. Rearrangement of N-Carboxyglutamic 1,5-Anhydride to the Leuchs' Anhydride and Conversion of the Latter to Pyroglutamic Acid,".

Kramer, Werner et al., "Intestinal Absorption of Peptides by Coupling to Bile Acids," *The Journal of Biochemistry*, 269(14):10621-10627 (1994).

Leibach, F.H, et al., "Peptide Transporters in the Intestine and the Kidney," *Annu Rev Nutri*, 16:99-119 (1996), Abstract.

Li, Chun, et al., "Complete Regression of Well-Established Tumors Using a Novel Water-Soluble Poly(L-Glutamic Acid)-Paclitaxel Conjugate," *Cancer Res*, 58:2404-2409 (1998).

Marriq, Claudine, et al., "Amino Acid Sequence of the Unique 3,5,3'-Triiodothyronine-Containing Sequence from Porcine Thyroglobulin," *Biochemical and Biophysical Research Communications*, 112(1):206-213 (1983).

Negishi, Naoki, et al., "Coupling of Naltrexone to Biodegradable Poly (α-Amino Acids)," *Pharmaceutical Research*, 4(4):305-310 (1987).

Nishida, Koyo, et al., "Pharmacokinetic Analysis of *in Vivo* Metabolism of Amino Acid or Dipeptide Conjugates of Salicylic Acid in Rabbit Intestinal Microorganisms," *Pharmaceutical Research*, 11(1):160-164 (1994).

Oh, D., et al., "Estimating the Fraction Dose Absorbed from Suspensions of Poorly Soluble Compounds in Humans: A Mathematical Model," *Pharmaceutical Research*, vol. 10, No. 2 (1993).

Oh, DM, et al., "Drug Transport and Targeting. Intestinal Transport," *Pharma Biotechnol*, 12:59-88 (1999), Abstract.

Okada, Masahiko, et al., "Synthesis of Glycopeptide-conjugates via Ring-Opening Polymerization of Sugar-Substituted α-Amino Acid N-Carboxyanhydrides (GlycoNCAs)," *Proc. Japan Acad.*, 73:205-209 (1997).

Orten, James M. et al., "Thyroxine," *Human Biochemistry*, 9$^{th}$ Ed., C.V. Mosby Company, St. Louis,pp. 401-405 (1975).

Pade, V., et al., "Link Between Drug Absorption Solubility and Permeability Measurements in Caco-2 Cells," *Journal of Pharmaceutical Sciences*, vol. 87, No. 12 (1998).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423-429 (1984).

Ryser, Hugues J.P., et al., "Conjugation of Methotrexate to Poly(L-lysine) Increases Drug Transport and Overcomes Drug Resistance in Cultured Cells," *Proc. Natl. Acad. Sci. USA*, 75(8):3867-3870 (1978).

Sawada, Kyoko, et al., "Recognition of L-Amino Acid Ester Compounds by Rat Peptide Transporters PEPT1 and PEPT2," *Journal of Pharmacology and Experimental Therapeutics*, 291(2):705-709 (1999).

Schmidt, Brigitte F., et al., "Peptide-Linked 1,3-Dialkyl-3-acyltriazenes: Gastrin Receptor Directed Antineoplastic Alkylating Agents," *Journal of Medicinal Chemistry*, 37(22):3812-3817 (1994).

Shen, H., et al., "Developmental Expression of PEPT1 and PEPT2 in Rat Small Intestine, Colon, and Kidney," *Pediatr Res*, 49(6):789-795 (2001), Abstract.

Shiraga, T., et al., "Cellular and Molecular Mechanisms of Dietary Regulation on Rat Intestinal H+/Peptide Transporter PepT1," *Gastroenterology*, 116(2):354-362 (1999), Abstract.

Tamai, I., et al., "Improvement of L-dopa Absorption by Dipeptidyl Derivation, Utilizing Peptide Transporter PepT1," *J. Pharma. Sci.*, 87(12):1542-1546 (1988), Abstract.

Toft, A., "Thyroid Hormone Replacement—One Hormore or Two?," *The New England Journal of Medicine*, vol. 340, No. 6 (1999).

Toth, Istvan, "A Novel Chemical Approach to Drug Delivery: Lipidic Amino Acid Conjugates," *Journal of Drug Targeting*, 2:217-239 (1994).

Zunino, Franco, et al., "Anti-Tumor Activity of Daunorubicin Linked to Poly-L-Aspartic Acid," *International Journal of Cancer*, 30:465-470 (1982).

Zunino, Franco, et al., "Comparison of Antitumor Effects of Daunorubicin Covalently Linked to Poly-L-Amino Acid Carriers," *European Journal of Cancer & Clinical Oncology*, 20(3):121-125 (1984).

International Search Report, Oct. 15, 2004.

Thomson Derwent World Patents Index.

Bai, J.P.F. et al., Gastrointestinal Transport of Peptide and Protein Drugs and Prodrugs, In: Welling PG, Balant LP, eds. Handbook of Experimental Pharmacology. Heidelberg: Springer-Verlag; 1994:110:189-206.

Kim, I. et al., A Novel Nucleoside Prodrug-Activating Enzyme: Substrate Specificity of Biphenyl Hydrolase-like Protein, Molecular Pharmaceutics, vol. 1, No. 2, 117-127.

March, J. et al., March's Advanced Organic Chemistry, Chapter 10, Section 10-11 Hydrolysis of Amides, pp. 474-476.

Schenk, J., The functioning neuronal transporter for dopamine: kinetic mechanisms and effects of amphetamines, cocaine and methyphenidata, Progress in Drug Research, vol. 59, 2002.

CAS No. 608137-32-2 (lysine amphetamine free base).

CAS No. 608137-33-3 (di-mesylate salt of lysine amphetamine).

CAS No. 100323-98-6 (di-oxalate salt of lysine amphetamine).

CAS No. 100323-97-5 (racemic lysine amphetamine free base).

CAS No. 5002-60-8, ((R,) stereoisomer of lysine amphetamine free base).

CAS No. 4907-02-2, ((R,) stereoisomer of di-oxalate salt of lysine amphetamine).

International Search Report, dated Dec. 19, 2003 for PCT/US03/05524.

International Search Report, dated Sep. 3, 2003 for PCT/US03/17009.

International Search Report, dated Oct. 15, 2004 for PCT/US04/017204.

* cited by examiner

Oral Formulation: Solution, 0.2 mg/mL in water

Figure 52A
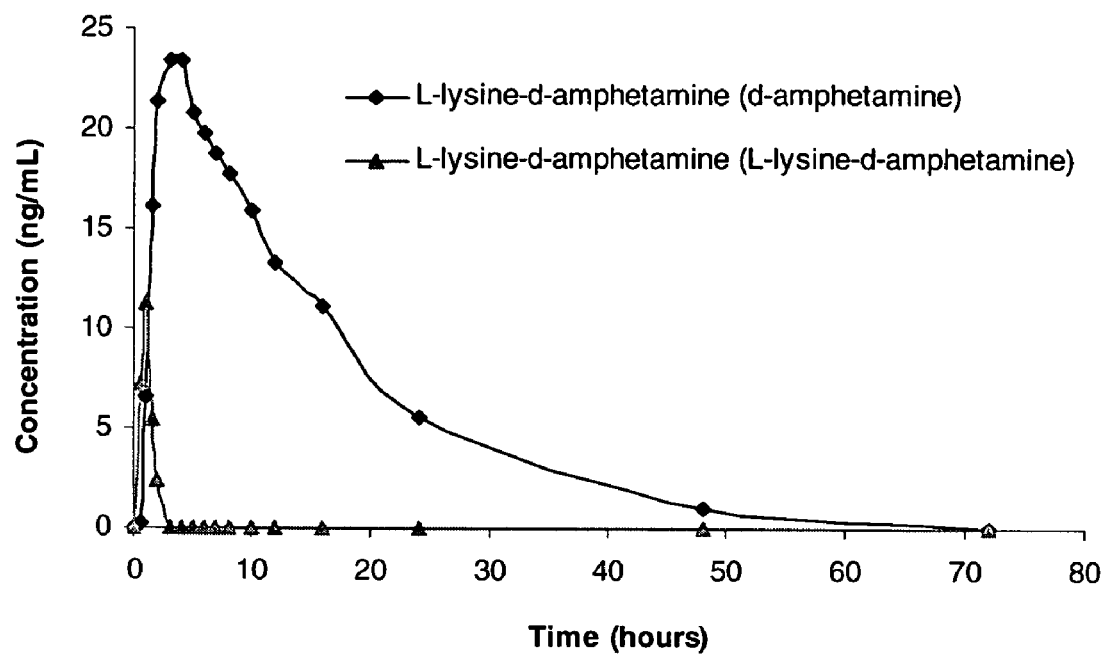
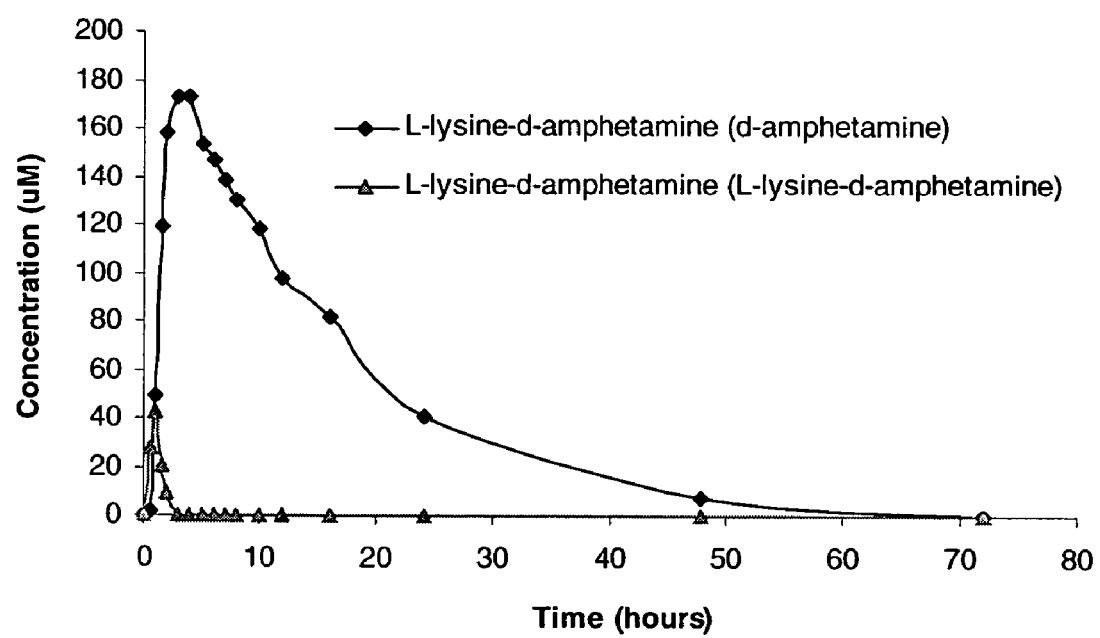
Figure 52B

Figure 53A
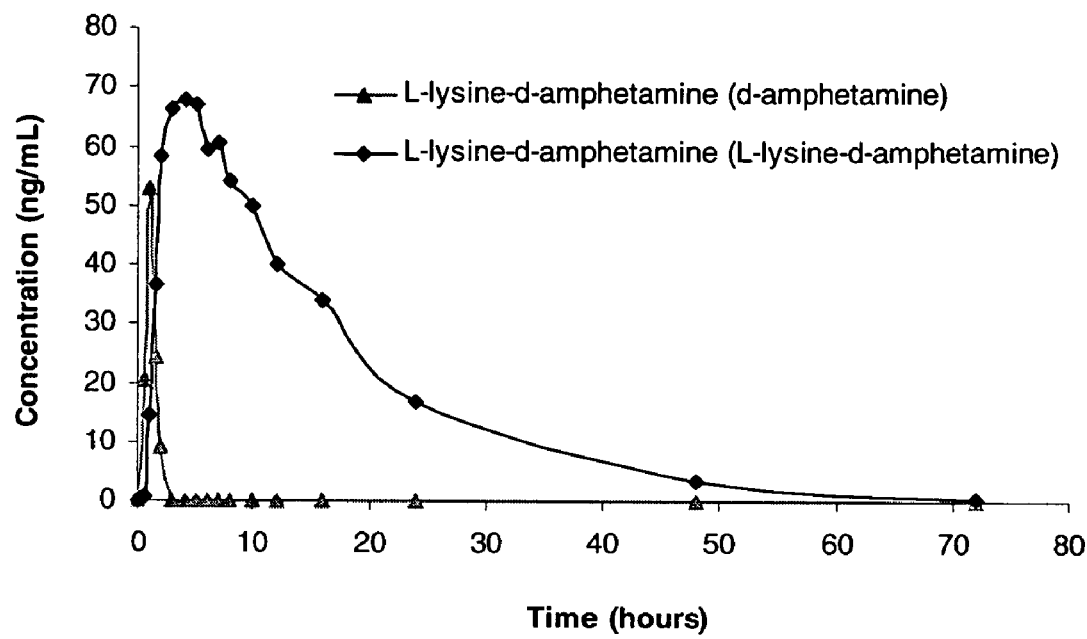
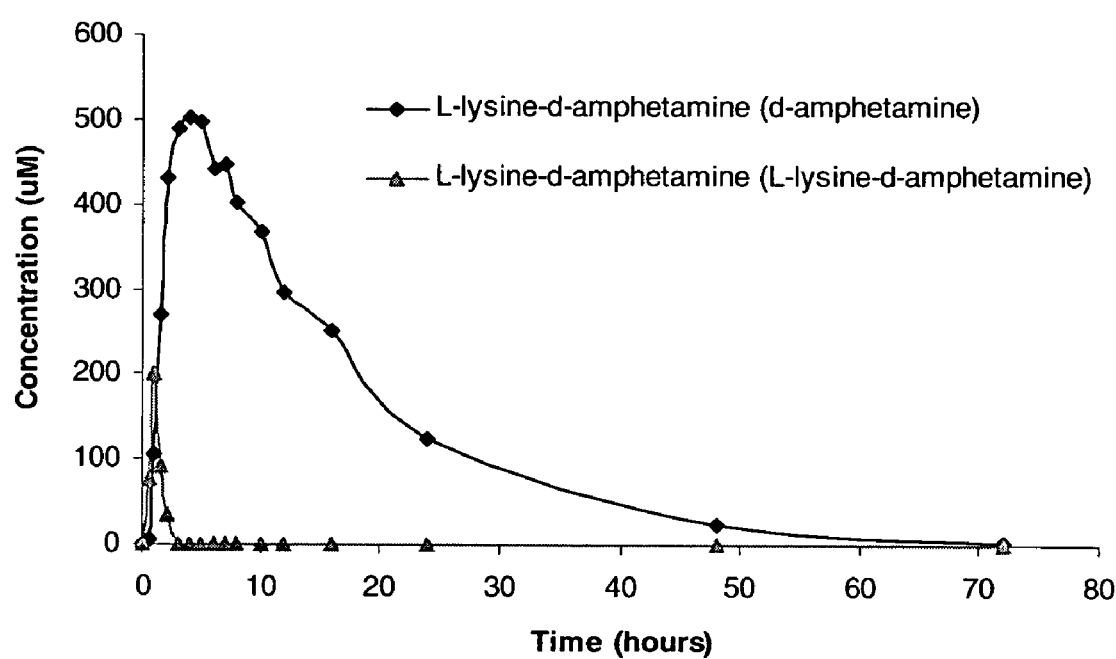
Figure 53B

Figure 54A
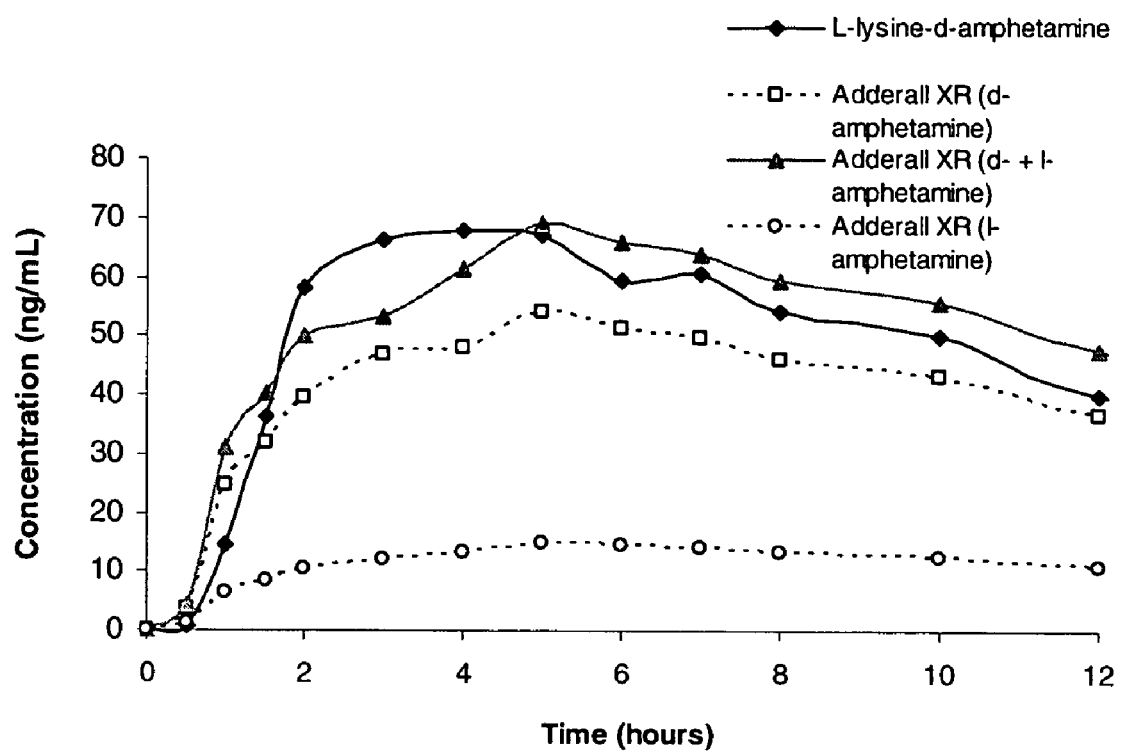
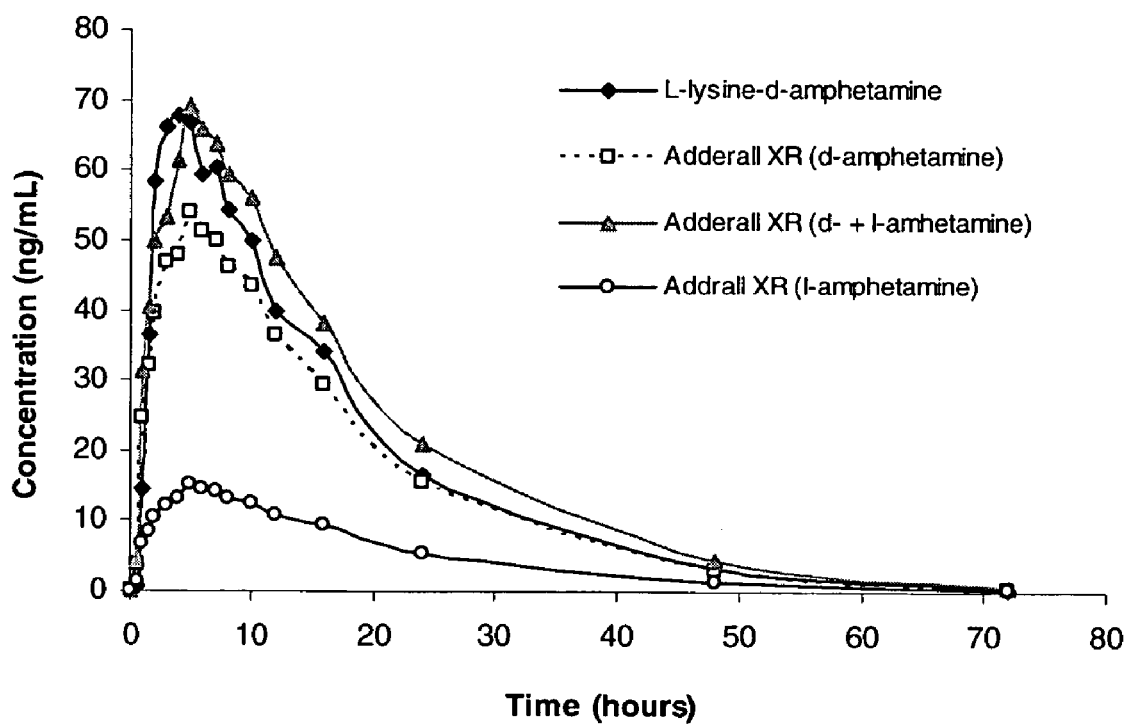
Figure 54B

Figure 55A
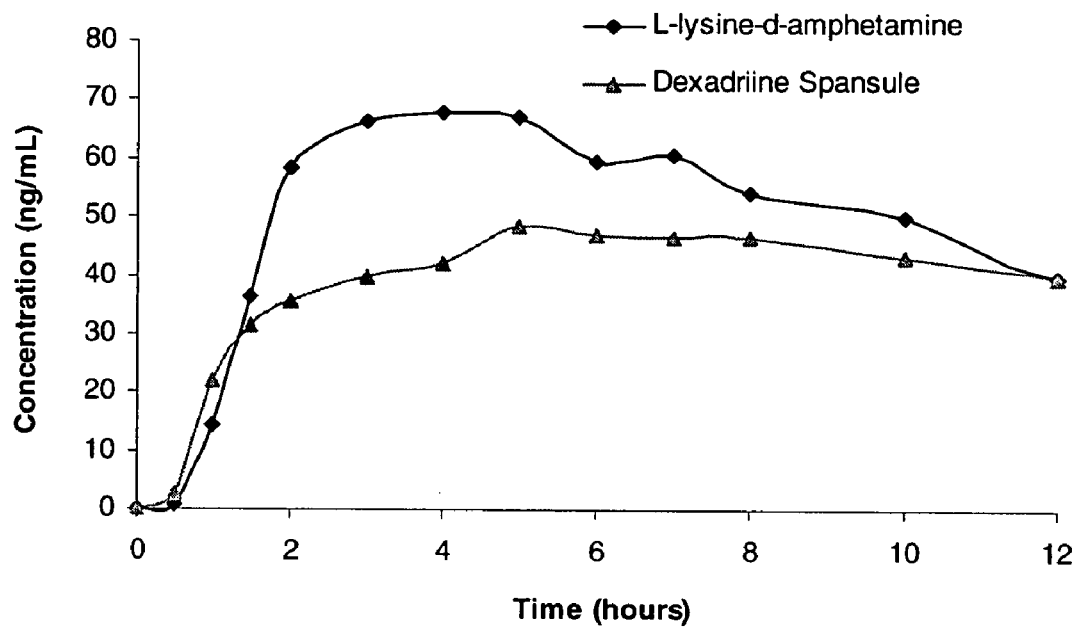
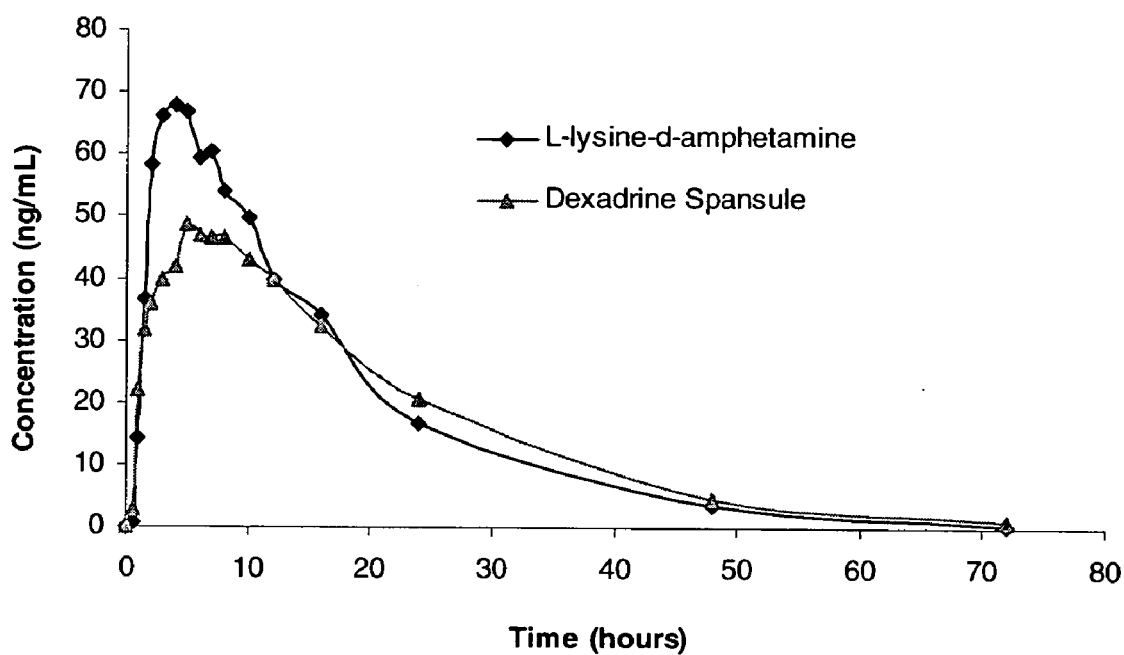
Figure 55B

ABUSE RESISTANT LYSINE AMPHETAMINE COMPOUNDS

CROSS REFERENCE RELATED APPLICATIONS

This application claims benefit under 35 U.S.C. 119(e) to U.S. provisional application No. 60/473,929 filed May 29, 2003 and provisional application No. 60/567,801 filed May 5, 2004, both of which are hereby incorporated by reference in their entirety.

BACKGROUND OF THE INVENTION (i) Field of the Invention

The invention relates to amphetamine compounds, compositions and methods of delivery and use comprising amphetamine covalently bound to a chemical moiety.

The invention relates to compounds comprised of amphetamine covalently bound to a chemical moiety in a manner that diminishes or eliminates pharmacological activity of amphetamine until released. The conjugates are stable in tests that simulate procedures likely to be used by illicit chemists in attempts to release amphetamine. The invention further provides for methods of therapeutic delivery of amphetamine compositions by oral administration. Additionally, release of amphetamine following oral administration occurs gradually over an extended period of time thereby eliminating spiking of drug levels. When taken at doses above the intended prescription, the bioavailability of amphetamine, including peak levels and total amount of drug absorbed, is substantially decreased. This decreases the potential for amphetamine abuse which often entails the use of extreme doses (1 g or more a day). The compositions are also resistant to abuse by parenteral routes of administration, such as intravenous "shooting", intranasal "snorting", or inhalation "smoking", that are often employed in illicit use. The invention thus provides a stimulant based treatment for certain disorders, such as attention deficit hyperactivity disorder (ADHD), which is commonly treated with amphetamine. Treatment of ADHD with compositions of the invention results in substantially decreased abuse liability as compared to existing stimulant treatments.

(ii) Background of the Invention

The invention is directed to amphetamine conjugate compounds, compositions, and methods of manufacture and use thereof. In particular, the invention is directed to an anti-abuse/sustained release formulation which maintains its therapeutic effectiveness when administered orally. The invention further relates to formulations which diminish or reduce the euphoric effect while maintaining therapeutically effective blood concentrations following oral administration.

Amphetamine is prescribed for the treatment of various disorders, including attention deficit hyperactivity disorder (ADHD), obesity and narcolepsy. Amphetamine and methamphetamine stimulate the central nervous system and have been used medicinally to treat ADHD, narcolepsy and obesity. Because of its stimulating effects amphetamine and its derivatives (e.g., amphetamine analogs) are often abused. Similarly, p-methoxyamphetamine, methylenedioxyamphetamine, 2,5-dimethoxy-4-methylamphetamine, 2,4,5-trimethoxyamphetamine and 3,4-methylenedioxymethamphetamine are also often abused.

In children with attention deficit hyperactivity disorder (ADHD), potent CNS stimulants have been used for several decades as a drug treatment given either alone or as an adjunct to behavioral therapy. While methylphenidate (Ritalin) has been the most frequently prescribed stimulant, the prototype of the class, amphetamine (alpha-methyl phenethylamine) has been used all along and increasingly so in recent years. (Bradley C, Bowen M, "Amphetamine (Benzedrine) therapy of children's behavior disorders." *American Journal of Orthopsychiatry* 11: 92) (1941).

The potential for abuse of amphetamines is a major drawback to its use. The high abuse potential has earned it Schedule II status according to the Controlled Substances Act (CSA). Schedule II classification is reserved for those drugs that have accepted medical use but have the highest potential for abuse. The abuse potential of amphetamine has been known for many years and the FDA requires the following black box warning in the package inserts of products:

Furthermore, recent developments in the abuse of prescription drug products increasingly raise concerns about the abuse of amphetamine prescribed for ADHD. Similar to OxyContin, a sustained release formulation of a potent narcotic analgesic, Adderall XR® represents a product with increased abuse liability relative to the single dose tablets. The source of this relates to the higher concentration of amphetamine in each tablet and the potential for release of the full amount of active pharmaceutical ingredient upon crushing. Therefore, like OxyContin, it may be possible for substance abusers to obtain a high dose of the pharmaceutical with rapid onset by snorting the powder or dissolving it in water and injecting it. (Cone, E. J., R. V. Fant, et al., "Oxycodone involvement in drug abuse deaths: a DAWN-based classification scheme applied to an oxycodone post-mortem database containing over 1000 cases." *J Anal Toxicol* 27(2): 57–67; discussion 67) (2003).

It has been noted recently that "53 percent of children not taking medication for ADHD knew of students with the disorder either giving away or selling their medications. And 34 percent of those being treated for the disorder acknowledged they had been approached to sell or trade them." (Dartmouth-Hitchcock, 2003) "Understanding ADHD Stimulant Abuse." http://12.42.224.168/healthyliving/familyhome/jan03familyhomestimulantabuse.htm). In addition, it was reported that students at one prep school obtained Dexedrine and Adderall to either swallow tablets whole or crush and sniff them. (Dartmouth-Hitchcock (2003).

According to the drug enforcement administration (DEA, 2003):

Methylphenidate and amphetamine can be abused orally or the tablets can be crushed and snorted or dissolved in water and injected. The pattern of abuse is characterized by escalation in dose, frequent episodes of binge use followed by severe depression and an overpowering desire to continue the use of these drugs despite serious adverse medical and social consequences.

Rendering this potent stimulant resistant to abuse, particularly by parenteral routes such as snorting or injecting, would provide considerable value to this otherwise effective and beneficial prescription medication.

(DEA (2003). "Stimulant Abuse By School Age Children: A Guide for School Officials."http://www.deadiversion.usdoj.gov/pubs/brochures/stimulant/
stimulant$_{13}$abuse.htm).

Typically, sustained release formulations contain drug particles mixed with or covered by a polymer material, or blend of materials, which are resistant to degradation or disintegration in the stomach and/or in the intestine for a selected period of time. Release of the drug may occur by leaching, erosion, rupture, diffusion or similar actions depending upon the nature of the polymer material or polymer blend used. Additionally, these formulations are subject to breakdown following relatively simple protocols which allows for abuse of the active ingredient.

Conventionally, pharmaceutical manufacturers have used hydrophilic hydrocolloid gelling polymers such as hydroxypropyl methylcellulose, hydroxypropyl cellulose or Pullulan to formulate sustained release tablets or capsules. These polymers first form a gel when exposed to an aqueous environment of low pH thereby slowly diffusing the active medicament which is contained within the polymer matrix. When the gel enters a higher pH environment such as that found in the intestines, however, it dissolves resulting in a less controlled drug release. To provide better sustained release properties in higher pH environments, some pharmaceutical manufacturers use polymers which dissolve only at higher pHs, such as acrylic resins, acrylic latex dispersions, cellulose acetate phthalate, and hydroxypropyl methylcellulose phthalate, either alone or in combination with hydrophilic polymers.

These formulations are prepared by combining the medicament with a finely divided powder of the hydrophilic polymer, or the hydrophilic and water-insoluble polymers. These ingredients are mixed and granulated with water or an organic solvent and the granulation is dried. The dry granulation is then usually further blended with various pharmaceutical additives and compressed into tablets.

Although these types of formulations have been successfully used to manufacture dosage forms which demonstrate sustained release properties, these formulations are subject to several shortcomings including uneven release and are subject to abuse.

The need exists for an abuse resistant dosage form of amphetamine which is therapeutically effective. Further, the need exists for an amphetamine dosage form which provides sustained release and sustained therapeutic effect.

SUMMARY OF INVENTION

The invention provides covalent attachment of amphetamine and derivatives or analogs thereof to a variety of chemical moieties. The chemical moieties may include any substance which results in a prodrug form, i.e., a molecule which is converted into its active form in the body by normal metabolic processes. The chemical moieties may be for instance, amino acids, peptides, glycopeptides, carbohydrates, nucleosides, or vitamins.

The chemical moiety is covalently attached either directly or indirectly through a linker to the amphetamine. The site of attachment is typically determined by the functional group(s) available on the amphetamine.

In one embodiment of the invention, the chemical moiety is a carrier peptide as defined herein. The carrier peptide may be attached to amphetamine through the carrier's N-terminus, C-terminus or side chain of an amino acid which may be either a single amino acid or part of a longer chain sequence (i.e. a dipeptide, tripeptide, an oligopeptide or a polypeptide). Preferably, the carrier peptide is (i) an amino acid, (ii) a dipeptide, (iii) a tripeptide, (iv) an oligopeptide, or (v) polypeptide. The carrier peptide may also be (i) a homopolymer of a naturally occurring amino acid, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids. A further embodiment of the carrier and/or conjugate is that the unattached portion of the carrier/conjugate may be in a free and unprotected state, or in the form of an ester or salt thereof. Preferably, synthetic amino acids with alkyl side chains are selected from alkyls of $C_1$–$C_{17}$ in length and more preferably from $C_1$–$C_6$ in length.

Covalent attachment of a chemical moiety to amphetamine can decrease its pharmacological activity when administered through injection or intranasally. Compositions of the invention, however, provide amphetamine covalently attached to a chemical moiety which remains orally bioavailable. The bioavailability is a result of the hydrolysis of the covalent linkage following oral administration. Hydrolysis is time-dependent, thereby allowing amphetamine to become available in its active form over an extended period of time. In one embodiment, the composition provides oral bioavailability which resembles the pharmacokinetics observed for extended release formulations. In another embodiment, release of amphetamine is diminished or eliminated when delivered by parenteral routes.

In one embodiment, the compositions maintain their effectiveness and abuse resistance following the crushing of the tablet, capsule or other oral dosage form. In contrast, conventional extended release formulations used to control the release of amphetamine through incorporation into matrices are subject to release of up to the entire amphetamine content immediately following crushing. When the content of the crushed tablet is injected or snorted, the large dose of amphetamine produces the "rush" effect sought by addicts.

In one embodiment, the amphetamine is attached to a single amino acid which is either naturally occurring or a synthetic amino acid. In another embodiment, the amphetamine is attached to a dipeptide or tripeptide, which could be any combination of the naturally occurring amino acids and synthetic amino acids. In another embodiment, the amino acids are selected from L-amino acids for digestion by proteases.

In another embodiment, the side chain attachment of amphetamine to the polypeptide or amino acid are selected from homopolymers or heteropolymers of glutamic acid, aspartic acid, serine, lysine, cysteine, threonine, asparagine, arginine, tyrosine, and glutamine. Examples of peptides include, Lys, Ser, Phe, Gly-Gly-Gly, Leu-Ser, Leu-Glu, homopolymers of Glu and Leu, and heteropolymers of (Glu)n-Leu-Ser. In a preferred embodiment, the composition is selected from Lys-Amp, Ser-Amp, Phe-Amp, and Gly-Gly-Gly-Amp.

In another embodiment, the invention provides a carrier and amphetamine which are bound to each other but otherwise unmodified in structure. This embodiment may further be described as the carrier having a free carboxy and/or amine terminal and/or side chain groups other than at the location of attachment for the amphetamine. In a preferred embodiment, the carrier, whether a single amino acid, dipeptide, tripeptide, oligopeptide or polypeptide, comprises only naturally occurring amino acids.

Another embodiment of the invention provides a method for delivering amphetamine dosage which prevents euphoria, comprising administering to a patient in need a composition formulated for oral dosage comprising amphetamine covalently attached to a chemical moiety wherein said blood levels of amphetamine maintain a therapeutically effect level but do not result in a euphoric effect.

In another embodiment, the covalent attachment of a chemical moiety substantially decreases the potential for overdose by decreasing the toxicity of amphetamine at doses above those considered therapeutic, while maintaining its pharmaceutical activity within a normal dose range. Covalent attachment of the chemical moiety may decrease or eliminate the pharmacological activity of amphetamine. Therefore, restoring activity requires release of the amphetamine from the chemical moiety. At higher doses partial or complete saturation of processes responsible for amphetamine release may be reached thus diminishing or eliminating the release of harmful levels of active amphetamine. For example, aspects of pharmacological activity, release, saturation are further depicted in FIGS. 1–55.

In another embodiment of the invention, the covalent attachment of a chemical moiety substantially decreases the potential for overdose by decreasing the rate or overall amount of absorption of the amphetamine when given at doses above those considered therapeutic.

In another embodiment of the invention, the covalent attachment of a chemical moiety substantially decreases the potential for overdose by increasing the rate or overall amount of clearance of amphetamine when given at doses above those considered therapeutic.

Another embodiment provides a method of treating a patient suffering from attention deficit hyperactivity disorder, narcolepsy or obesity comprising providing, administering, prescribing, etc. compositions of the invention.

Another embodiment of the invention provides a method for delivering amphetamine, comprising providing a patient with a therapeutically effective amount of amphetamine covalently attached to a chemical moiety which provides a therapeutically bioequivalent AUC when compared to amphetamine alone but does not provide a $C_{max}$ which results in euphoria when taken orally.

Other objects, advantages and embodiments of the invention are described below and will be obvious from this description and practice of the invention.

BRIEF DESCRIPTION OF DRAWINGS

FIGS. 52A–B. Plasma d-amphetamine and L-lysine-d-amphetamine levels (52A, ng/mL; 52B, μM) over a 72 hour period following oral administration of L-lysine-d-amphetamine (25 mg L-lysine-d-amphetamine mesylate containing 7.37 mg d-amphetamine base) to humans (LC/MS/MS analysis).

FIGS. 53A–B. Plasma d-amphetamine and L-lysine-d-amphetamine levels (53A, ng/mL; 53B, μM) over a 72 hour period following oral administration of L-lysine-d-amphetamine (25 mg L-lysine-d-amphetamine mesylate containing 22.1 mg d-amphetamine base) to humans (LC/MS/MS analysis).

FIGS. 54A–B. Plasma d-amphetamine levels (54A, 0–12 hours; 54B, 0–72 hours) following oral administration of L-lysine-d-amphetamine (75 mg L-lysine-d-amphetamine mesylate containing 22.1 mg d-amphetamine base) or Adderall XR® (35 mg containing 21.9 mg amphetamine base to humans (LC/MS/MS analysis).

FIGS. 55A–B. Plasma d-amphetamine levels (55A, 0–12 hours; 55B, 0–72 hours) following oral administration of L-lysine-d-amphetamine (75 mg L-lysine-d-amphetamine mesylate containing 22.1 mg d-amphetamine base) or Dexadrine Spansule® (30 mg containing 22.1 mg amphetamine base) to humans (LC/MS/MS analysis).

DETAILED DESCRIPTION OF THE INVENTION

Figure 1:
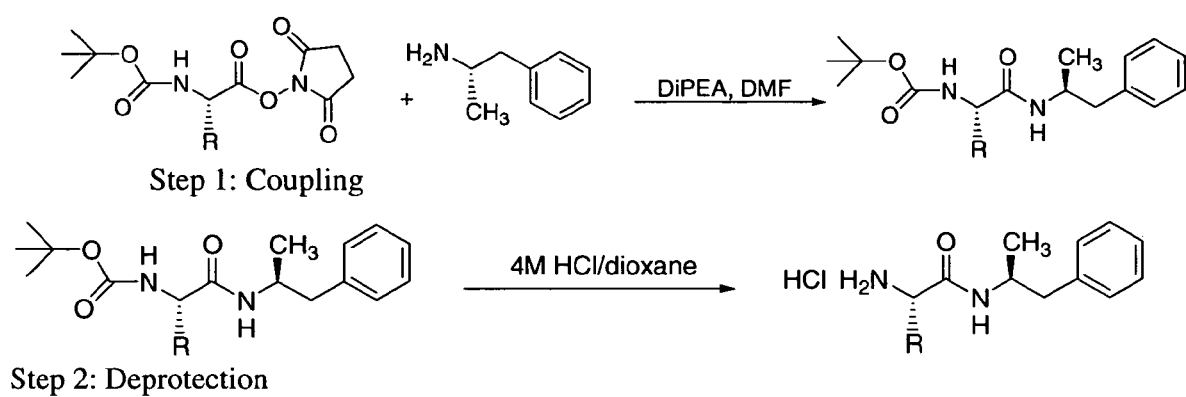
FIG. 1. Synthesis of amino acid amphetamine conjugates.
Figure 2:
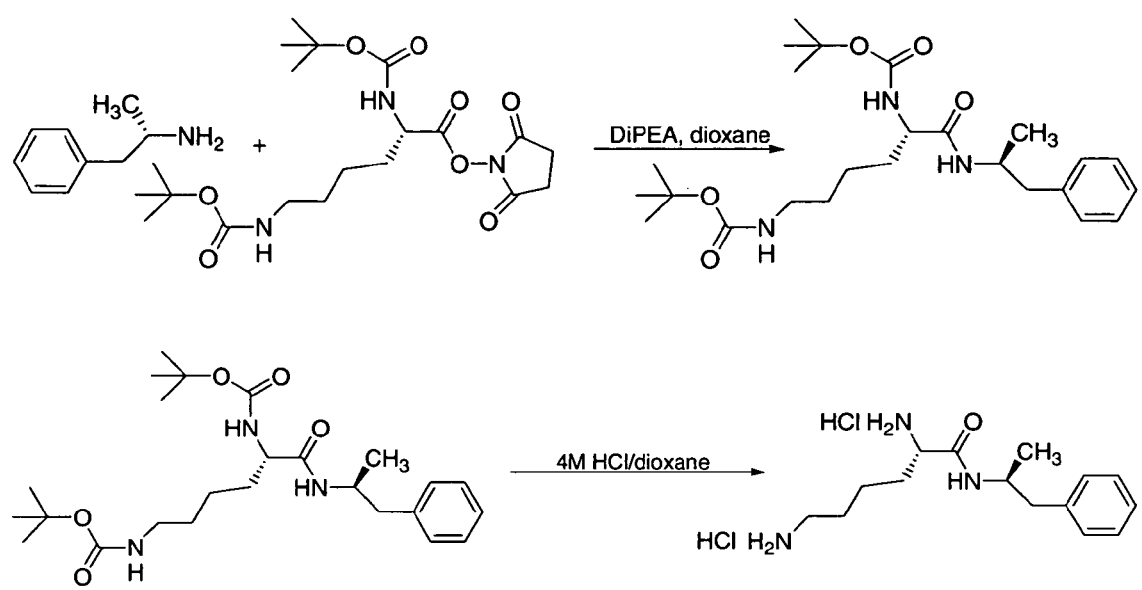
FIG. 2. Synthesis of lysine amphetamine conjugate.
Figure 3:
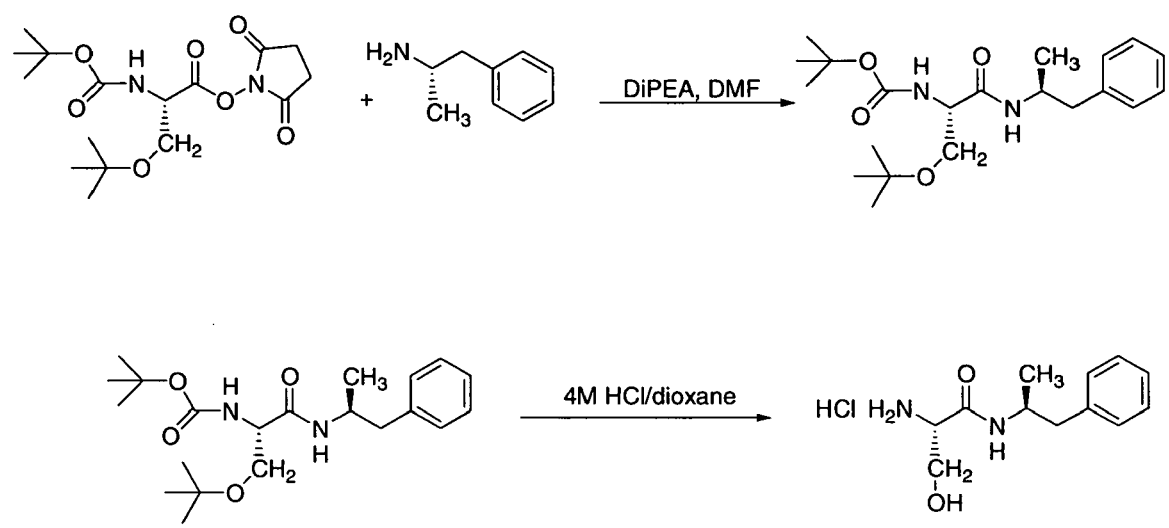
FIG. 3. Synthesis of serine amphetamine conjugate.
Figure 4:
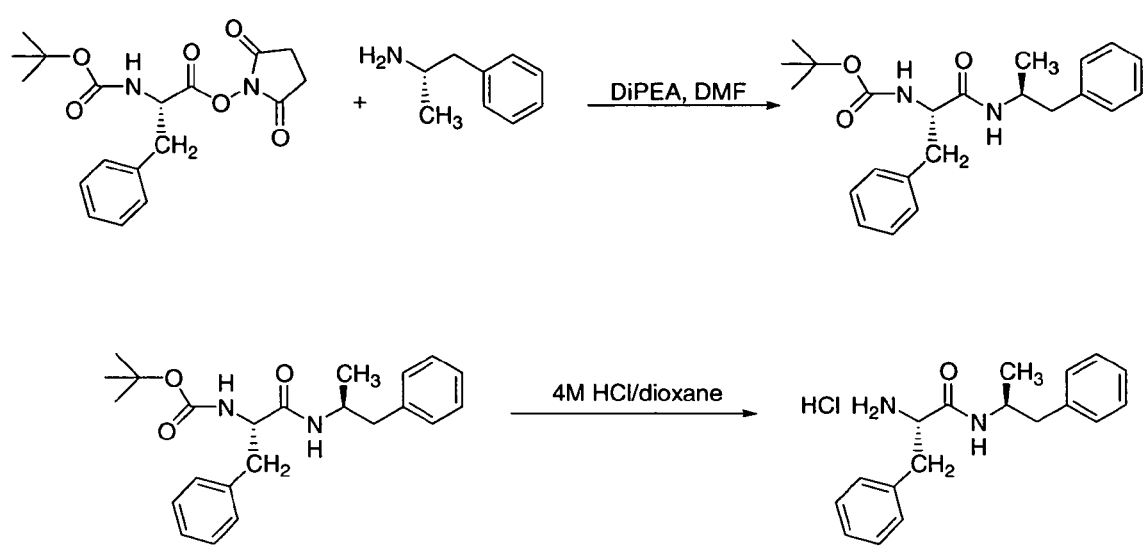
FIG. 4. Synthesis of phenylalanine amphetamine conjugate.
Figure 5:
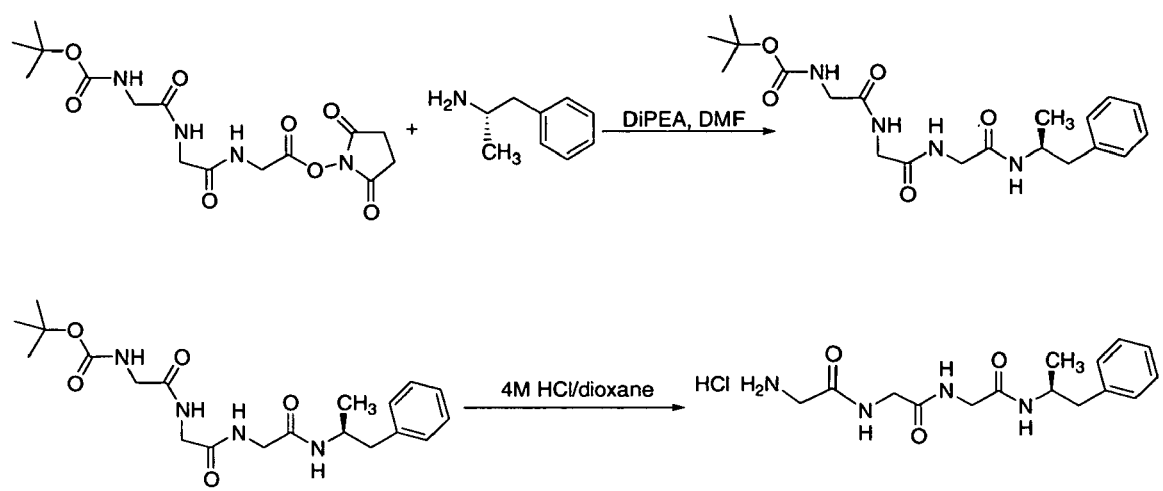
FIG. 5. Synthesis of triglycine amphetamine conjugate.

In accordance with the present invention and as used herein, the following terms are defined with the following meanings, unless explicitly stated otherwise. For additional methods of attaching amphetamine to carriers, see application number U.S. Ser. No. 10/156,527, and/or PCT/US03/05524 and/or PCT/US03/05525 each of which is hereby incorporated by reference in its entirety.

The invention utilizes covalent modification of amphetamine to decrease its potential for causing overdose or abuse. The amphetamine is covalently modified in a manner that decreases its pharmacological activity, as compared to the unmodified amphetamine, at doses above those considered therapeutic. When given at lower doses, such as those intended for therapy, the covalently modified amphetamine retains pharmacological activity similar to that of the unmodified amphetamine. The covalent modification of amphetamine may comprise the attachment of any chemical moiety through conventional chemistry.

Compounds, compositions and methods of the invention provide reduced potential for overdose, reduced potential for abuse or addiction, and/or improve amphetamine's characteristics with regard to high toxicities or suboptimal release profiles. Without wishing to be limited to the following theory, we believe that overdose protection results from a natural gating mechanism at the site of hydrolysis that limits the release of the active amphetamine from the prodrug at greater than therapeutically prescribed amounts. Therefore, abuse resistance is provided by limiting the "rush" or "high" available from the active amphetamine released by the prodrug and limiting the effectiveness of alternative routes of administration. Further, it is believed that the prodrug itself does not cross the blood brain barrier and is thus substantially absent from the central nervous system.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, polypeptide or carrier peptide to illustrate specific embodiments for the active agent conjugate. Preferred lengths of the conjugates and other preferred embodiments are described herein.

Throughout this application the use of "chemical moiety" is meant to include at least amino acid(s), peptide(s), glycopeptide(s), carbohydrate(s), lipid(s), nucleoside(s), or vitamin(s).

Carbohydrates include sugars, starches, cellulose, and related compounds. e.g., $(CH_2O)_n$, wherein n is an integer larger than 2 or $C_n(H_2O)_{n-1}$, with n larger than 5. More specific examples include, for instance, fructose, glucose, lactose, maltose, sucrose, glyceraldehyde, dihydroxyacetone, erythrose, ribose, ribulose, xylulose, galactose, mannose, sedoheptulose, neuraminic acid, dextrin, and glycogen.

A glycoprotein is a carbohydrate (or glycan) covalently linked to protein. The carbohydrate may be in the form of a monosaccharide, disaccharide(s), oligosaccharide(s), polysaccharide(s), or their derivatives (e.g. sulfo- or phospho-substituted).

A glycopeptide is a carbohydrate linked to an oligopeptide composed of L-and /or D-amino acids. A glyco-amino-acid is a saccharide attached to a single amino acid by any kind of covalent bond. A glycosyl-amino-acid is a compound consisting of saccharide linked through a glycosyl linkage (O—, N— or S—) to an amino acid.

A "composition" as used herein refers broadly to any composition containing a described molecule conjugate(s). The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

"Amphetamine" shall mean any of the sympathomimetic phenethylamine derivatives which have central nervous system stimulant activity, such as but not limited to, amphetamine, methamphetamine, p-methoxyamphetamine, methylenedioxyamphetamine, 2,5-dimethoxy-4-methylamphetamine, 2,4,5-trimethoxyamphetamine and 3,4-methylenedioxymethamphetamine.

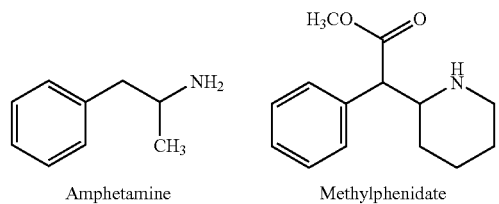

Amphetamine            Methylphenidate

Other embodiments are described according to the following abbreviations.

Lys-Amp=L-lysine-d-amphetamine, Lys-Amph, Lysine-Amphetamine, KAMP,

K-amphetamine, or 2,6-diaminohexanoic acid-(1-methyl-2-phenylethyl)-amide

Phe-Amp=Phenylalanine-Amphetamine, FAMP, or 2-amino-3-phenylpropanoic acid-(1-methyl-2-phenylethyl)-amide, Ser-Amp=Serine-Amphetamine, SAMP, or 2-amino-3-hydroxylpropanoic acid-(1-methyl-2-phenylethyl)-amide, Gly$_3$-Amp=GGG-Amphetamine, GGGAMP, or 2-Amino-N-({[(1-methyl-2-phenyl-ethylcarbomyl)-methyl]-carbomyl}-methyl)-acetamide This patent is meant to cover all compounds discussed regardless of absolute configurations. Thus, natural, L-amino acids are discussed but the use of D-amino acids are also included. Similarly, references to amphetamine should be interpreted as inclusive of dextro- and levo-isomers.

Furthermore, the following abbreviations may be used throughout the patent.

BOC=t-butyloxycarbonyl
CMC=carboxymethylcellulose
DIPEA=di-isopropyl ethyl amine
mp=melting point
NMR=nuclear magnetic resonance
OSu=hydroxysuccinimido ester "In a manner inconsistent with the manufacturer's instructions" is meant to include but is not limited to consuming amounts greater than amounts described on the label or ordered by a licensed physician, and/or altering by any means (e.g. crushing, breaking, melting, separating etc.) the dosage formulation such that the composition maybe injected, inhaled or smoked.

Use of the phrases such as, "decreased", "reduced", "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

For each of the recited embodiments, the amphetamine may be any of the above discussed stimulants. In one embodiment, the amphetamine is dextroamphetamine or methylphenidate.

The attached chemical moiety may be any chemical substance that decreases the pharmacological activity until amphetamine is released. Preferably the chemical moiety is a single amino acid, dipeptide or tripeptide. Amphetamine binds to specific sites to produce various effects (Hoebel, et al., 1989). The attachment of certain chemical moieties can therefore diminish or prevent binding to these biological target sites. Further, the covalent modification may prevent stimulant activity by preventing the drug from crossing the blood-brain barrier. Preferably, absorption of the composition into the brain is prevented or substantially diminished and/or delayed when delivered by routes other than oral administration.

The attached chemical moiety may further comprise naturally occurring or synthetic substances. This includes, but is not limited to, the attachment of amphetamine to amino acids, peptides, lipids, carbohydrates, glycopeptides, nucleic acids or vitamins. These chemical moieties could be expected to affect delayed release in the gastrointestinal tract and prevent rapid onset of the desired activity, particularly when delivered by parenteral routes. (Hoebel, B. G., L. Hernandez, et al., "Microdialysis studies of brain norepinephrine, serotonin, and dopamine release during ingestive behavior. Theoretical and clinical implications." Ann N Y Acad Sci 575: 171–91) (1989).

For each of the recited embodiments, the amino acid or peptide may comprise one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment, the amino acid or peptide is comprised of one or more of the naturally occurring (D) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine. In another embodiment, the amino acid or peptide is comprised of one or more unnatural, non-standard or synthetic amino acids such as, aminohexanoic acid, biphenylalanine, cyclohexylalanine, cyclohexyiglycine, diethyiglycine, dipropyiglycine, 2,3-diaminopropionic acid, homophenylalanine, homoserine, homotyrosine, naphthylalanine, norleucine, omithine, phenylalanine (4-fluoro), phenylalanine(2,3,4,5,6 pentafluoro), phenylalanine(4-vitro), phenyiglycine, pipecolic acid, sarcosine, tetrahydroisoquinoline-3-carboxylic acid, and tert-leucine. In another embodiment, the amino acid or peptide comprises one or more amino acid alcohols, for example, serine and threonine. In another embodiment the amino acid or peptide comprises one or more N-methyl amino acids, for example, N-methyl aspartic acid.

In another embodiment, the specific carriers are utilized as a base short chain amino acid sequence and additional amino acids are added to the terminus or side chain. In another embodiment, the above amino acid sequence may have one more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E], whereas histidine (His)[H] is similar to proline (Pro)[P], and glycine (Gly)[G] is similar to tryptophan (Trp)[W]. In the alternative, the preferred amino acid substitutions may be selected according to hydrophilic properties (i.e., polarity) or other common characteristics associated with the 20 essential amino acids. While preferred embodiments utilize the 20 natural amino acids for their GRAS characteristics, it is recognized that minor substitutions along the amino acid chain which do not effect the essential characteristics of the amino acid chain are also contemplated.

In one embodiment, the carrier range is between one to 12 chemical moieties with one to 8 moieties being preferred. In another embodiment, the number of chemical moieties is selected from 1, 2, 3, 4, 5, 6, or 7. In another embodiment, the molecular weight of the carrier portion of the conjugate is below about 2,500, more preferably below about 1,000, and most preferably below about 500 kD. In one embodiment, the chemical moiety is a single lysine. In another embodiment, the chemical moiety is a lysine bound to an additional chemical moiety.

Another embodiment of the invention is a composition for preventing overdose comprising amphetamine which has been covalently bound to a chemical moiety.

Another embodiment of the invention is a composition for safely delivering amphetamine comprising a therapeutically effective amount of said amphetamine which has been covalently bound to a chemical moiety wherein said chemical moiety reduces the rate of absorption of the amphetamine as compared to delivering the unbound amphetamine.

Another embodiment of the invention is a composition for reducing amphetamine toxicity comprising amphetamine which has been covalently bound to a chemical moiety wherein said chemical moiety increases the rate of clearance when given at doses exceeding those within the therapeutic range of said amphetamine.

Another embodiment of the invention is a composition for reducing amphetamine toxicity comprising amphetamine which has been covalently bound to a chemical moiety wherein said chemical moiety provides a serum release curve which does not increase above amphetamine's toxicity level when given at doses exceeding those within the therapeutic range of amphetamine.

Another embodiment of the invention is a composition for reducing bioavailability of amphetamine comprising amphetamine covalently bound to a chemical moiety wherein said bound amphetamine maintains a steady-state serum release curve which provides a therapeutically effective bioavailability but prevents spiking or increased blood serum concentrations compared to unbound amphetamine when given at doses exceeding those within the therapeutic range of amphetamine.

Another embodiment of the invention is a composition for preventing a $C_{max}$ spike for amphetamine when taken by means other than orally while still providing a therapeutically effective bioavailability curve if taken orally comprising an amphetamine which has been covalently bound to a chemical moiety.

Another embodiment of the invention is a composition for preventing a toxic release profile in a patient comprising amphetamine covalently bound to a chemical moiety wherein said bound amphetamine maintains a steady-state serum release curve which provides a therapeutically effective bioavailability but prevents spiking or increased blood serum concentrations compared to unbound amphetamine.

Another embodiment of the invention is a compound of Formula I:

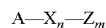

$$A-X_n-Z_m$$

wherein A is an amphetamine as defined herein; X is a chemical moiety as defined herein and n is between 1 and 50 and increments thereof; and Z is a further chemical moiety different from X which acts as an adjuvant and m is between 1 and 50 and increments thereof. In another embodiment, n is between 1 and 50, more preferably between 1 and 10, and m is 0.

Embodiments of the invention provide amphetamine compositions which allow the amphetamine to be therapeutically effective when delivered at the proper dosage but reduces the rate of absorption or extent of bioavailability of the amphetamine when given at doses exceeding those within the therapeutic range of amphetamine. Embodiments of the invention also provide amphetamine compositions wherein the covalently bound chemical moiety increases the rate of clearance of amphetamine when given at doses exceeding those within the therapeutic range of the amphetamine.

In another embodiment, the amphetamine compositions have substantially lower toxicity compared to unbound amphetamine. In another embodiment, the amphetamine compositions reduce or eliminate the possibility of overdose by oral administration. In another embodiment, the amphetamine compositions reduce or eliminate the possibility of overdose by intranasal administration. In another embodiment, the amphetamine compositions reduce or eliminate the possibility of overdose by injection. In another embodiment, the amphetamine compositions reduce or eliminate the possibility of overdose by inhalation.

In another embodiment, the amphetamine conjugates of the invention may further comprise a polymer blend which comprises a hydrophilic polymer and/or a water-insoluble polymer. The polymers may be used according to industry standards to further enhance the sustained release/abuse resistant properties of the amphetamine conjugate without reducing the abuse resistance. For instance, a composition might include: about 70% to about 100% amphetamine conjugate by weight, from about 0.01% to about 10% of a hydrophilic polymer (e.g. hydroxypropyl methylcellulose), from about 0.01% to about 2.5% of a water-insoluble polymer (e.g. acrylic resin), from about 0.01% to about 1.5% of additives (e.g. magnesium stearate), and from about 0.01% to about 1% colorant by weight.

Hydrophilic polymers suitable for use in the sustained release formulations include one or more natural or partially or totally synthetic hydrophilic gums such as acacia, gum tragacanth, locust bean gum, guar gum, or karaya gum, modified cellulosic substances such as methylcellulose, hydroxymethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art, or a combination of such polymers. These hydrophilic polymers gel and would dissolve slowly in aqueous acidic media thereby allowing the amphetamine conjugate to diffuse from the gel in the stomach. When the gel reaches the intestines it would dissolve in controlled quantities in the higher pH medium to allow further sustained release. Preferred hydrophilic polymers are the hydroxypropyl methylcelluloses such as those manufactured by The Dow Chemical Company and known as Methocel ethers, such as Methocel E1OM.

Other formulations may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants such as Emerald Green Lake, FD&C Red No. 40, FD&C Yellow No. 6, D&C Yellow No. 10, or FD&C Blue No. 1 and other various certified color additives (See 21 CFR, Part 74); binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. In one preferred embodiment, a sustained release formulation further comprises magnesium stearate and Emerald Green Lake.

An amphetamine conjugate, which is further formulated with excipients, may be manufactured according to any appropriate method known to those of skill in the art of pharmaceutical manufacture. For instance, the amphetamine-conjugate and a hydrophilic polymer may be mixed in a mixer with an aliquot of water to form a wet granulation. The granulation may be dried to obtain hydrophilic polymer encapsulated granules of amphetamine-conjugate. The resulting granulation may be milled, screened, then blended with various pharmaceutical additives such as, water insoluble polymers, and/or additional hydrophilic polymers. The formulation may then be tableted and may further be film coated with a protective coating which rapidly dissolves or disperses in gastric juices.

However, it should be noted that the amphetamine conjugate controls the release of amphetamine into the digestive tract over an extended period of time resulting in an improved profile when compared to immediate release combinations and prevention of abuse without the addition of the above additives. In a preferred embodiment, no further sustained release additives are required to achieve a blunted or reduced pharmacokinetic curve (e.g., reduced euphoric effect) while achieving therapeutically effective amounts of amphetamine release when taken orally.

The compounds of the invention can be administered by a variety of dosage forms. Any biologically-acceptable dosage form known to persons of ordinary skill in the art, and combinations thereof, are contemplated. Examples of preferred dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets and combinations thereof.

The most effective means for delivering the abuse-resistant compounds of the invention is orally, to permit maximum release of the amphetamine, and provide therapeutic effectiveness and/or sustained release while maintaining abuse resistance. When delivered by oral route the amphetamine is released into circulation, preferably over an extended period of time as compared to amphetamine alone.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient. Tablets and other forms of presentation provided in discrete units conveniently contain a daily dose, or an appropriate fraction thereof, of one or more of the compounds of the invention. For example, units may contain from 5 mg to 500 mg, but more usually from 10 mg to 250 mg, of one or more of the compounds of the invention.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the amphetamine, particularly at doses above those intended for therapy. In another embodiment, the decrease in bioavailability occurs upon intranasal administration. In another embodiment, the decrease in bioavailability occurs upon intravenous administration.

For each of the described embodiments, one or more of the following characteristics may be realized: The toxicity of the amphetamine conjugate is substantially lower than that of the unbound amphetamine. The covalently bound chemical moiety reduces or eliminates the possibility of overdose by oral administration. The covalently bound chemical moiety reduces or eliminates the possibility of overdose or abuse by intranasal administration. The covalently bound chemical moiety reduces or eliminates the possibility of overdose or abuse by injection.

The invention further provides methods for altering amphetamines in a manner that decreases their potential for abuse. Methods of the invention provide various ways to regulate pharmaceutical dosage through covalent attachment of amphetamine to different chemical moieties. One embodiment provides a method of preventing overdose comprising administering to an individual amphetamine which has been covalently bound to a chemical moiety.

Another embodiment provides a method of safely delivering amphetamine comprising providing a therapeutically effective amount of an amphetamine which has been covalently bound to a chemical moiety wherein the chemical moiety reduces the rate of absorption of amphetamine as compared to delivering the unbound amphetamine.

Another embodiment provides a method of reducing amphetamine toxicity comprising providing a patient with amphetamine which has been covalently bound to a chemical moiety, wherein the chemical moiety increases the rate of clearance of pharmacologically active amphetamine (i.e., released amphetamine) when given at doses exceeding those within the therapeutic range of amphetamine.

Another embodiment provides a method of reducing amphetamine toxicity comprising providing a patient with amphetamine which has been covalently bound to a chemical moiety, wherein the chemical moiety provides a serum release curve which does not increase above the amphetamine's toxicity level when given at doses exceeding those within the therapeutic range for the unbound amphetamine.

Another embodiment provides a method of reducing bioavailability of amphetamine comprising providing amphetamine covalently bound to a chemical moiety, wherein the bound amphetamine maintains a steady-state serum release curve which provides a therapeutically effective bioavailability but prevents spiking or increased blood serum concentrations compared to unbound amphetamine when given at doses exceeding those within the therapeutic range for the unbound amphetamine.

Another embodiment provides a method of preventing a $C_{max}$ spike for amphetamine while still providing a therapeutically effective bioavailability curve comprising providing amphetamine which has been covalently bound to a chemical moiety.

In another embodiment, methods of the invention provide bioavailability curves similar to those of FIGS. 6–55.

Another embodiment provides a method for preventing a toxic release profile in a patient comprising administering to a patient amphetamine covalently bound to a chemical moiety, wherein said bound amphetamine maintains a steady-state serum release curve which provides a therapeutically effective bioavailability but prevents spiking or increased blood serum concentrations compared to unbound amphetamine, particularly when taken at doses above prescribed amounts.

Another embodiment of the invention is a method for reducing or preventing abuse of amphetamine comprising providing, administering, or prescribing said composition to a human in need thereof, wherein said composition comprises a chemical moiety covalently attached to amphetamine such that the pharmacological activity of amphetamine is decreased when the composition is used in a manner inconsistent with the manufacturer's instructions.

Another embodiment of the invention is a method for reducing or preventing abuse of amphetamine comprising consuming an amphetamine conjugate of the invention, wherein said conjugate comprises a chemical moiety covalently attached to amphetamine such that the pharmacological activity of amphetamine is substantially decreased when the composition is used in a manner inconsistent with the manufacturer's instructions.

Another embodiment of the invention is a method of preventing overdose of amphetamine comprising providing, administering, or prescribing an amphetamine composition of the invention to a human in need thereof, wherein said composition comprises a chemical moiety covalently attached to amphetamine in a manner that decreases the potential of overdose from amphetamine.

Another embodiment of the invention is a method of preventing overdose of amphetamine, comprising consuming an amphetamine composition of the invention, wherein said composition comprises a chemical moiety covalently attached to amphetamine in a manner that decreases the potential of overdose from amphetamine.

Another embodiment of the invention is a method for reducing or preventing the euphoric effect of amphetamine comprising providing, administering, or prescribing to a human in need thereof, a composition comprising a chemical moiety covalently attached to amphetamine such that the pharmacological activity of amphetamine is decreased when the composition is used in a manner inconsistent with the manufacturer's instructions.

Another embodiment of the invention is a method for reducing or preventing the euphoric effect of amphetamine, comprising consuming a composition comprising a chemical moiety covalently attached to amphetamine such that the pharmacological activity of amphetamine is decreased when the composition is used in a manner inconsistent with the manufacturer's instructions.

Another embodiment of the invention is any of the preceding methods wherein said amphetamine composition is adapted for oral administration, and wherein said amphetamine is resistant to release from said chemical moiety when the composition is administered parenterally, such as intranasally or intravenously. Preferably, said amphetamine may be released from said chemical moiety in the presence of acid and/or enzymes present in the stomach, intestinal tract, or blood serum. Optionally, said composition may be in the form of a tablet, capsule, oral solution, oral suspension, or other oral dosage form discussed herein.

For each of the recited methods, the chemical moiety may be one or more amino acid(s), oligopeptide(s), polypeptide(s), carbohydrate(s), glycopeptide(s), nucleic acid(s), or vitamin(s). Preferably, said chemical moiety is an amino acid, oligopeptide, or polypeptide or carbohydrate. Where the chemical moiety is a polypeptide, preferably said polypeptide comprises fewer than 70 amino acids, fewer than 50 amino acids, fewer than 10 amino acids, or fewer than 4 amino acids. Where the chemical moiety is an amino acid, preferably said amino acid is lysine, serine, phenylalanine or glycine. Most preferably, said amino acid is lysine.

For each of the recited embodiments, covalent attachment may comprise an ester or carbonate bond.

For each of the recited methods, the composition may yield a therapeutic effect without substantial euphoria. Preferably, said amphetamine composition provides a therapeutically bioequivalent AUC when compared to amphetamine alone but does provide a $C_{max}$ which results in euphoria.

Another embodiment of the invention is a method for reducing or preventing abuse of amphetamine comprising orally administering an amphetamine composition of the invention to a human in need thereof, wherein said composition comprises an amino acid or peptide (e.g., lysine) covalently attached to amphetamine such that the pharmacological activity of amphetamine is decreased when the composition is used in a manner inconsistent with the manufacturer's instructions.

Another embodiment is a method of preventing overdose of an amphetamine comprising orally administering an amphetamine composition to a human in need thereof, wherein said composition comprises an amino acid or peptide (e.g., lysine) covalently attached to amphetamine in a manner that decreases the potential of amphetamine to result in overdose.

Another embodiment is a method for reducing or preventing the euphoric effect of amphetamine comprising orally administering an amphetamine composition to a human in need thereof, wherein said composition comprises an amino acid or peptide (e.g., lysine) covalently attached to amphetamine such that the pharmacological activity of amphetamine is decreased when the composition is used in a manner inconsistent with the manufacturer's instructions.

For each of the recited methods of the invention the following properties may be achieved through bonding amphetamine to the chemical moiety. In one embodiment, the toxicity of the compound may be lower than that of the amphetamine when delivered in its unbound state or as a salt thereof. In another embodiment, the possibility of overdose by oral administration is reduced or eliminated. In another embodiment, the possibility of overdose by intranasal administration is reduced or eliminated. In another embodiment, the possibility of overdose by injection administration is reduced or eliminated.

Another embodiment of the invention provides methods of treating various diseases or conditions comprising administering compounds or compositions of the invention which further comprise commonly prescribed active agents for the respective illness or disease wherein the amphetamine is covalently attached to a chemical moiety. For instance, one embodiment of the invention comprises a method of treating attention deficit hyperactivity disorder (ADHD) comprising administering to a patient amphetamine covalently bound to a chemical moiety. Another embodiment provides a method of treating attention deficit disorder (ADD) comprising administering to a patient compounds or compositions of the invention, amphetamine covalently bound to a chemical moiety.

Another embodiment of the invention provides a method of treating narcolepsy comprising administering to a patient compounds or compositions of the invention.

In order to facilitate a more complete understanding of the invention, Examples are provided below. However, the scope of the invention is not limited to specific embodiments disclosed in these Examples, which are for purposes of illustration only.

EXAMPLES

Example 1

General Synthesis of Amino Acid-Amphetamine Conjugates.

Amino acid conjugates were synthesized by the general method described in FIGS. 1–5.

Example 2

Synthesis of L-lysine-d-amphetamine

L-lysine-d-amphetamine was synthesized (see FIG. 2) by the following method:

a. Coupling

| Reagents | MW | Weight | mmoles | Molar Equivalents |
|---|---|---|---|---|
| d-amphetamine freebase | 135.2 | 4.75 g | 35.13 | 1 |
| Boc-Lys(Boc)-OSu | 443.5 | 15.58 g | 35.13 | 1 |
| Di-iPr-Et-Amine | 129 | 906 mg | 7.03 | 0.2, d = 0.74, 1.22 mL |
| 1,4-Dioxane | — | 100 mL | — | — |

To a solution of Boc-Lys(Boc)-OSu (15.58 g, 35.13 mmol) in dioxane (100 mL) under an inert atmosphere was added d-amphetamine freebase (4.75 g, 35.13 mmol) and DiPEA (0.9 g, 1.22 mL, 7.03 mmol). The resulting mixture was allowed to stir at room temperature overnight. Solvent and excess base were then removed using reduced pressure evaporation. The crude product was dissolved in ethyl acetate and loaded on to a flash column (7 cm wide, filled to 24 cm with silica) and eluted with ethyl acetate. The product was isolated; the solvent reduced by rotary evaporation and the purified protected amide was dried by high-vac to obtain a white solid. $^1$H NMR (DMSO-d$_6$) δ 1.02–1.11 (m, 2H, Lys γ-CH$_2$), δ 1.04 (d, 3H, Amp α-CH$_3$), δ 1.22–1.43 (m, 4H, Lys-β and δ-CH$_2$), δ 1.37 (18H, Boc, 6×CH$_3$), δ 2.60–2.72 (2H, Amp CH$_2$), δ 3.75–3.83, (m, 1H, Lys α-H) δ 3.9–4.1 (m, 1H, Amp α-H), δ 6.54–6.61 (d, 1H, amide NH), δ

6.7–6.77 (m, 1H, amide NH), δ 7.12–7.29 (m, 5H, ArH), δ 7.65–7.71 (m, 1, amide NH); mp=86–88° C.

b. Deprotection

| Reagents | MW | Weight | mmoles | Molar Equivalents |
|---|---|---|---|---|
| 4 M HCl in dioxane | 4 mmol/mL | 50 mL | 200 | 6.25 |
| Boc-Lys(Boc)-Amp | 463.6 | 14.84 g | 32 | 1 |
| 1,4-Dioxane | — | 50 mL | — | — |

The protected amide was dissolved in 50 mL of anhydrous dioxane and stirred while 50 mL (200 mmol) of 4M HCl/dioxane was added and stirred at room temperature overnight. The solvents were then reduced by rotary evaporation to afford a viscous oil. Addition of 100 mL MeOH followed by rotary evaporation resulted in a golden colored solid material that was further dried by storage at room temperature under high vacuum.

$^1$H NMR (DMSO-d$_6$) δ 0.86–1.16 (m, 2H, Lys γ-CH$_2$), δ 1.1 (d, 3H, Amp α-CH$_3$), δ 1.40–1.56 (m, 4H, Lys-β and δ-CH$_2$), δ 2.54–2.78 (m, 2H, Amp CH$_2$, 2H, Lys ε-CH$_2$), 3.63–3.74 (m, 1H, Lys α-H), δ 4.00–4.08 (m, 1H, Amp α-H), δ 7.12–7.31 (m, 5H, Amp ArH), δ 8.13–8.33 (d, 3H, Lys amine) δ 8.70–8.78 (d, 1H, amide NH); mp=120–122°

Example 3

Synthesis of Ser-Amp

Ser-Amp was synthesized by a similar method (see FIG. 3) except the amino acid starting material was Boc-Ser(O-C-tBu)-OSu and the deprotection was done using a solution of trifluoroacetic acid instead of HCl.

Example 4

Synthesis of Phe-Amp

Phe-Amp was synthesized by a similar method (see FIG. 4) except the amino acid starting material was Boc-Phe-OSu.

Example 5

Synthesis of Gly$_3$-Amp Gly$_3$-Amp was synthesized by a similar method (see FIG. 5) except the amino acid starting material was Boc-GGG-OSu.

Example 6

Pharmacokinetics of L-lysine-d-amphetamine Compared to d-amphetamine sulfate (ELISA Analysis)

Male Sprague-Dawley rats were provided water ad libitum, fasted overnight and dosed by oral gavage L-lysine-d-amphetamine or d-amphetamine sulfate. In all studies doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. L-lysine-d-amphetamine was also determined to be essentially unreactive in the ELISA (<1%).

Figure 6:
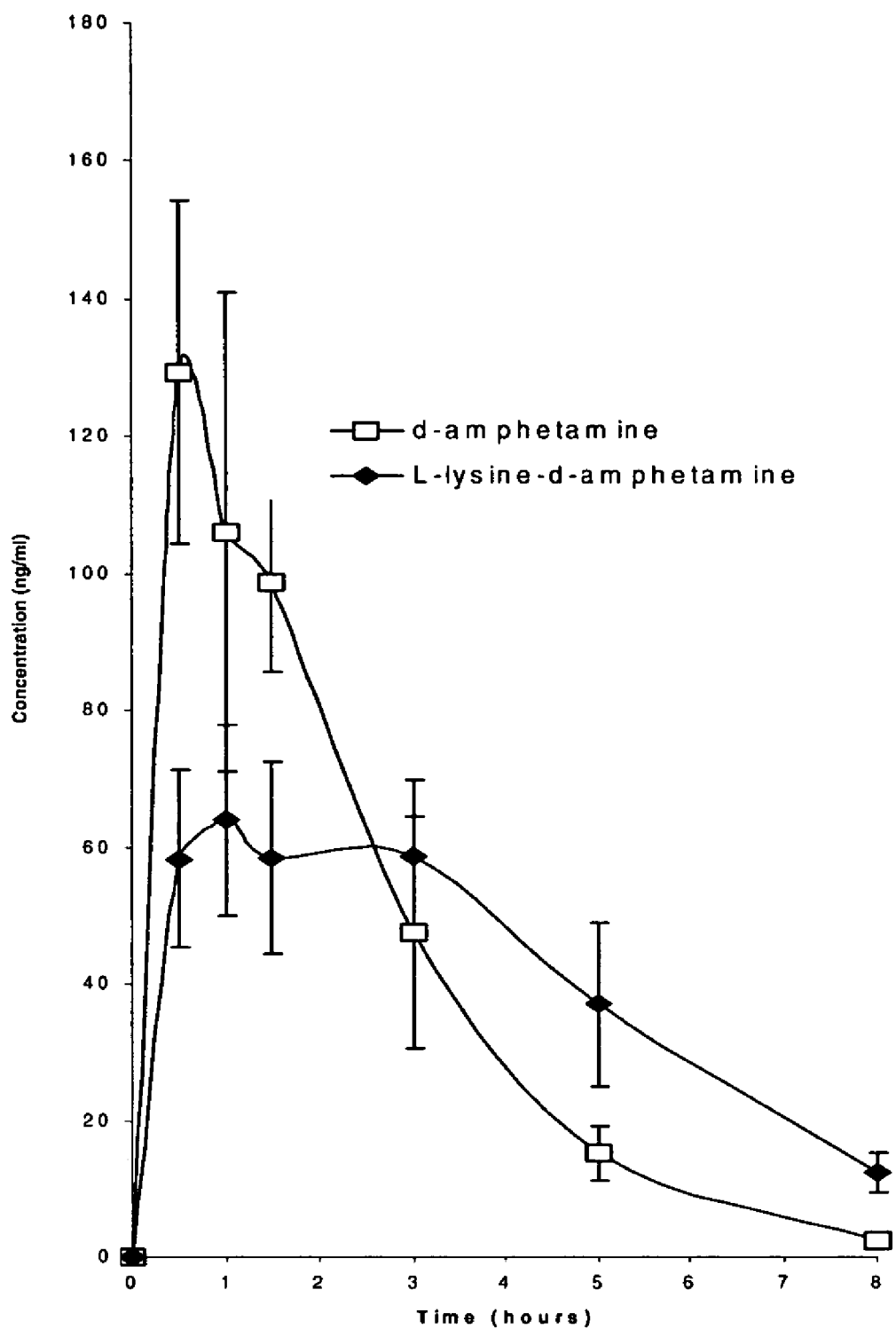
FIG. 6. Plasma concentrations of d-amphetamine from individual animals orally administered d-amphetamine or L-lysine-d-amphetamine.

Mean (n=4) plasma concentration curves of d-amphetamine or L-lysine-d-amphetamine are shown in FIG. 6. Extended release was observed in all four L-lysine-d-amphetamine dosed animals and $C_{max}$ was substantially decreased as compared to animals dosed with d-amphetamine sulfate. Plasma d-amphetamine concentrations of individual animals for d-amphetamine or L-lysine-d-amphetamine are shown in Table 1. The mean plasma d-amphetamine concentrations are shown in Table 2. The time to peak concentration for L-lysine-d-amphetamine was similar to that of d-amphetamine. Pharmacokinetic parameters for oral administration of d-amphetamine or L-lysine-d-amphetamine are summarized in Table 3.

TABLE 1

Plasma Concentrations of d-amphetamine from Individual Animals Orally Administered d-amphetamine or L-lysine-d-amphetamine (3 mg/kg d-amphetamine base).

| | d-amphetamine (ng/ml) | | | | L-lysine-d-amphetamine (ng/ml) | | | |
|---|---|---|---|---|---|---|---|---|
| Time (hours) | Rat #1 | Rat #2 | Rat #3 | Rat #4 | Rat #1 | Rat #2 | Rat #3 | Rat #4 |
| 0.5 | 144 | 157 | 101 | 115 | 52 | 62 | 74 | 44 |
| 1 | 152 | 78 | 115 | 78 | 48 | 72 | 79 | 57 |
| 1.5 | 85 | 97 | 117 | 95 | 42 | 62 | 76 | 53 |
| 3 | 34 | 45 | 72 | 38 | 61 | 60 | 71 | 43 |
| 5 | 20 | 14 | 12 | 15 | 49 | 33 | 44 | 22 |
| 8 | 3 | 3 | 2 | 2 | 15 | 14 | 12 | 8 |

TABLE 2

Mean Plasma Concentrations of d-amphetamine Following Oral Administration of d-amphetamine or L-lysine-d-amphetamine.

| | Plasma d-amphetamine Concentrations (ng/ml) | | | | | |
|---|---|---|---|---|---|---|
| | d-amphetamine | | | L-lysine-d-amphetamine | | |
| Hours | Mean | +/− SD | CV | Mean | +/− SD | CV |
| 0.5 | 129 | 25 | 20 | 58 | 13 | 22 |
| 1 | 106 | 35 | 33 | 64 | 14 | 22 |
| 1.5 | 99 | 13 | 14 | 58 | 14 | 25 |
| 3 | 47 | 17 | 36 | 59 | 11 | 19 |
| 5 | 15 | 4 | 24 | 37 | 12 | 32 |
| 8 | 2 | 1 | 35 | 12 | 3 | 24 |

TABLE 3

Pharmacokinetic Parameters of d-amphetamine Following Oral Administration of d-amphetamine or L-lysine-d-amphetamine.

| Drug | AUC (0–8 h) ng/ml h | Percent Amphetamine | Cmax (ng/ml) | Percent Amphetamine | Mean Peak (ng/ml) | Percent Amphetamine |
|---|---|---|---|---|---|---|
| Amphetamine | 341 +/− 35 | 100 | 111 +/− 27 | 100 | 129 | 100 |
| Lys-Amp | 333 +/− 66 | 98 | 61 +/− 13 | 55 | 64 | 50 |

Example 6 illustrates that when lysine is conjugated to the active agent amphetamine the peak levels of amphetamine are decreased while bioavailability is maintained approximately equal to amphetamine. The bioavailability of amphetamine released from L-lysine-d-amphetamine is similar to that of amphetamine sulfate at the equivalent dose, thus L-lysine-d-amphetamine maintains its therapeutic value. The gradual release of amphetamine from L-lysine-d-amphetamine and decrease in peak levels reduce the possibility of overdose.

Figure 7:
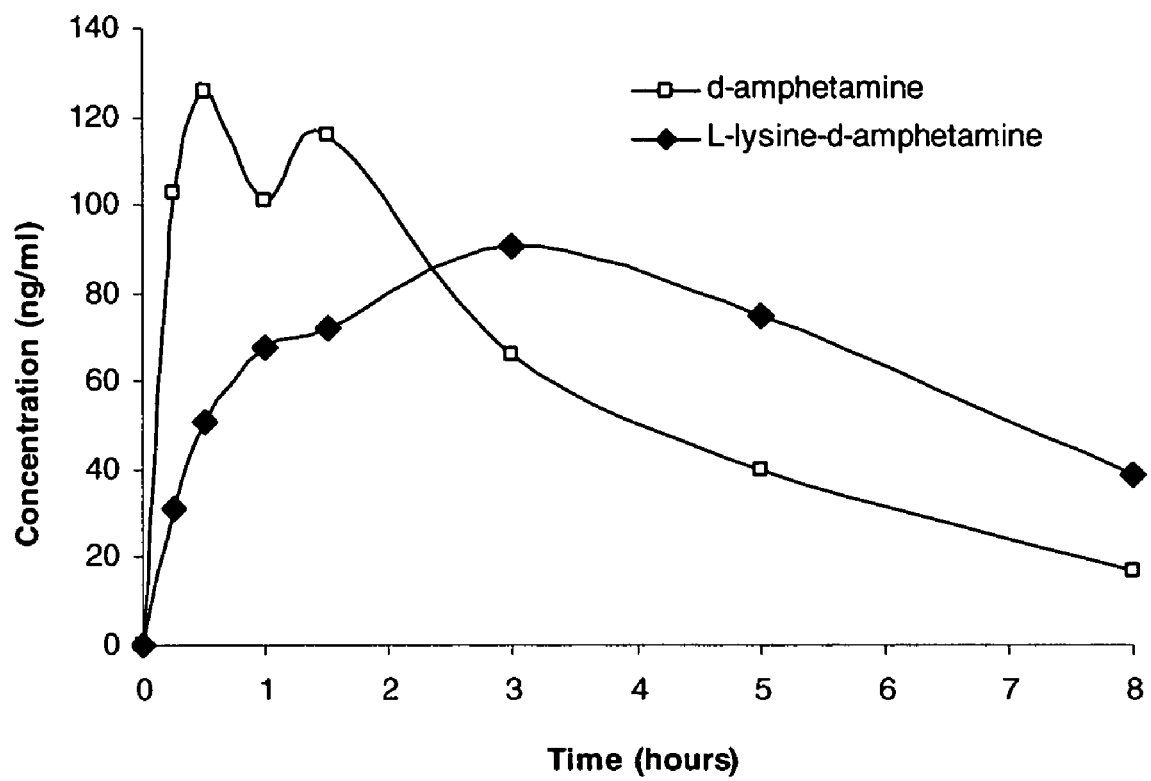
FIG. 7. Plasma concentrations of d-amphetamine following oral administration of d-amphetamine sulfate or L-lysine-d-amphetamine (1.5 mg/kg d-amphetamine base) to rats (ELISA analysis).
Figure 8:
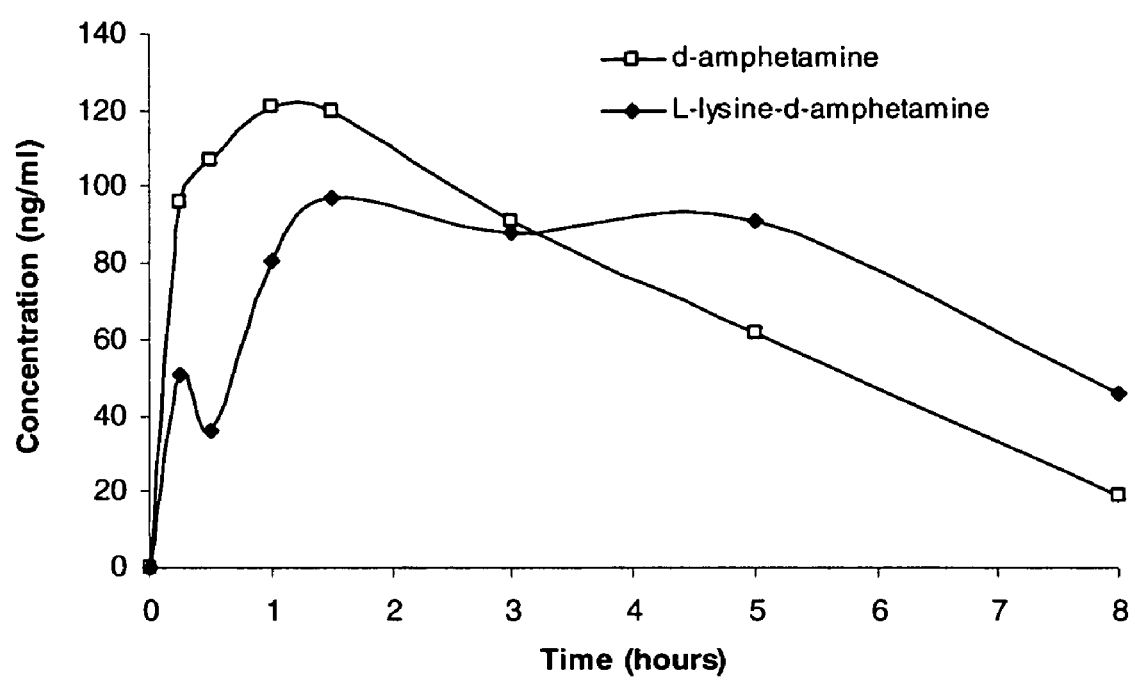
FIG. 8. Plasma concentrations of d-amphetamine following oral administration of d-amphetamine sulfate or L-lysine-d-amphetamine (3 mg/kg d-amphetamine base) to rats (ELISA analysis).
Figure 9:
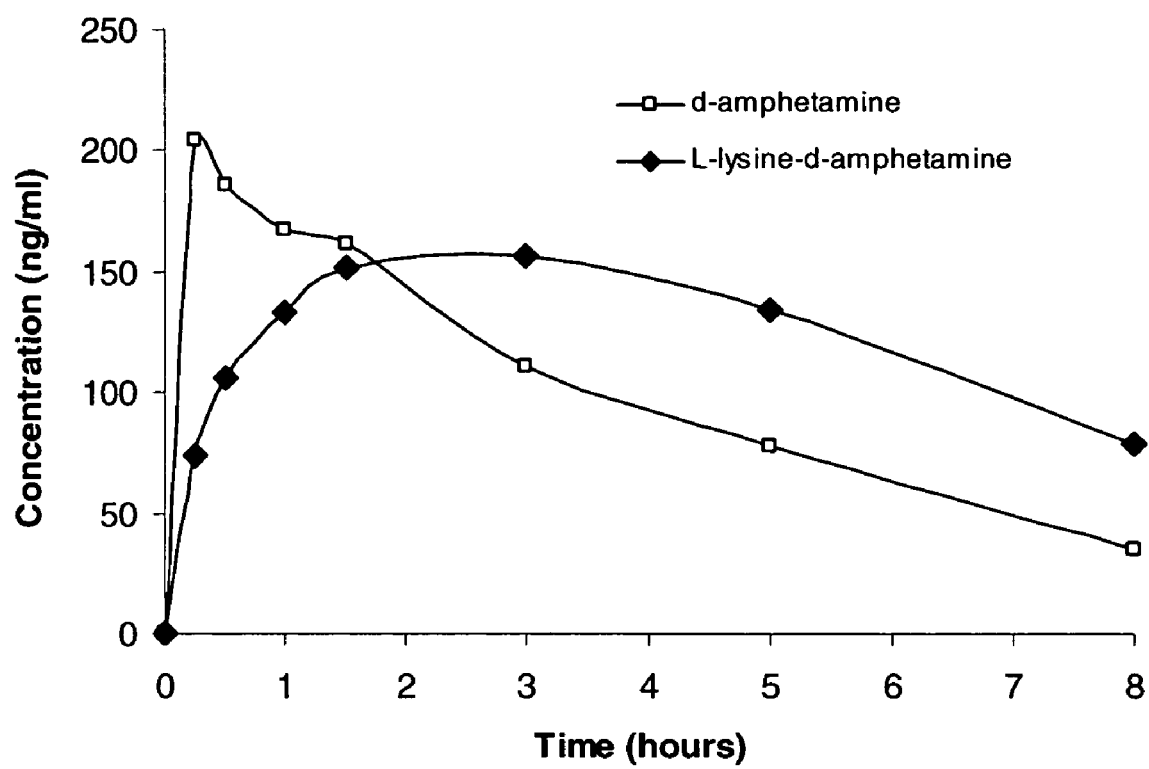
FIG. 9. Plasma concentrations of d-amphetamine following oral administration of d-amphetamine sulfate or L-lysine-d-amphetamine (6 mg/kg d-amphetamine base) to rats (ELISA analysis).
Figure 10:
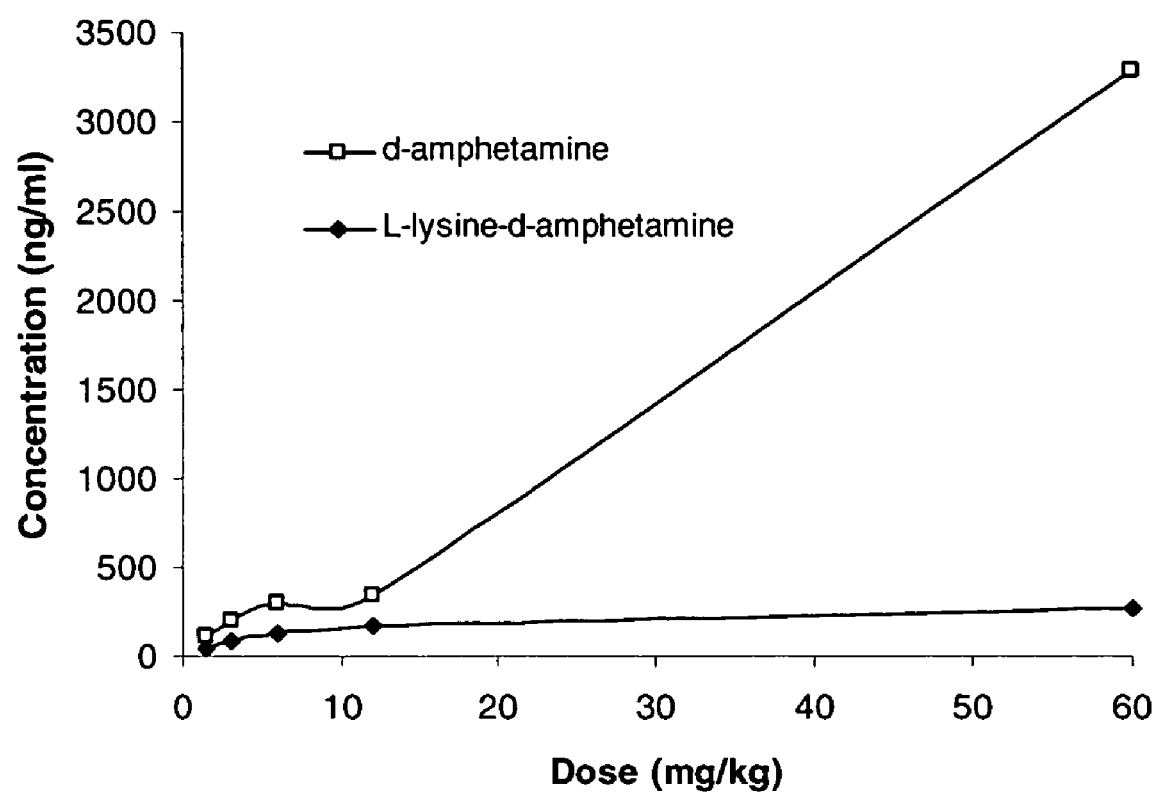
FIG. 10. Plasma concentrations of d-amphetamine at 30-minutes post-dose for escalating doses of L-lysine-d-amphetamine or d-amphetamine sulfate (ELISA analysis).

Example 7
Oral Bioavailability of L-lysine-d-amphetamine at Various Doses Approximating a Range of Therapeutic Human Doses Mean (n=4) plasma concentration curves of d-amphetamine vs. L-lysine-d-amphetamine are shown for rats orally administered 1.5, 3, and 6 mg/kg in FIGS. 7, 8 and 9, respectively. Extended release was observed at all three doses for L-lysine-d-amphetamine dosed animals. The mean plasma concentrations for 1.5, 3, and 6 mg/kg are shown in Tables 4, 5 and 6, respectively. Pharmacokinetic parameters for oral administration of d-amphetamine vs. L-lysine-d-amphetamine at the various doses are summarized in Table 7.

TABLE 4

Mean Plasma Concentrations of d-amphetamine vs. L-lysine-d-amphetamine Following Oral Admistration (1.5 mg/kg)

| | Plasma Amphetamine Concentrations (ng/ml) | | | | | |
|---|---|---|---|---|---|---|
| | d-amphetamine | | | L-lysine-d-amphetamine | | |
| Hours | Mean | +/− SD | CV | Mean | +/− SD | CV |
| 0 | 0 | 0 | 0 | 0 | 0 | 0 |
| 0.25 | 103 | 22 | 21 | 31 | 11 | 37 |
| 0.5 | 126 | 20 | 16 | 51 | 23 | 45 |
| 1 | 101 | 27 | 27 | 68 | 23 | 34 |
| 1.5 | 116 | 28 | 24 | 72 | 10 | 14 |
| 3 | 66 | 13 | 20 | 91 | 5 | 5 |
| 5 | 40 | 7 | 18 | 75 | 16 | 22 |
| 8 | 17 | 2 | 15 | 39 | 13 | 34 |

TABLE 5

Mean Plasma Concentrations of d-amphetamine vs. L-lysine-d-amphetamine Following Oral Admistration (3 mg/kg)

| | Plasma Amphetamine Concentrations (ng/ml) | | | | | |
|---|---|---|---|---|---|---|
| | d-amphetamine | | | L-lysine-d-amphetamine | | |
| Hours | Mean | +/− SD | CV | Mean | +/− SD | CV |
| 0 | 0 | | | 0 | | |
| 0.25 | 96 | 41 | 43 | 51 | 49 | 97 |
| 0.5 | 107 | 49 | 46 | 36 | 35 | 96 |
| 1 | 121 | 17 | 14 | 81 | 44 | 54 |
| 1.5 | 120 | 33 | 27 | 97 | 32 | 33 |
| 3 | 91 | 30 | 33 | 88 | 13 | 15 |
| 5 | 62 | 22 | 36 | 91 | 21 | 23 |
| 8 | 19 | 6 | 33 | 46 | 16 | 34 |

TABLE 6

Mean Plasma Concentrations of d-amphetamine vs. L-lysine-d-amphetamine Following Oral Admistration (6 mg/kg).

| | Plasma Amphetamine Concentrations (ng/ml) | | | | | |
|---|---|---|---|---|---|---|
| | d-amphetamine | | | L-lysine-d-amphetamine | | |
| Hours | Mean | +/− SD | CV | Mean | +/− SD | CV |
| 0 | 0 | | | 0 | | |
| 0.25 | 204 | 14 | 7 | 74 | 38 | 51 |
| 0.5 | 186 | 9 | 5 | 106 | 39 | 37 |
| 1 | 167 | 12 | 7 | 133 | 33 | 24 |
| 1.5 | 161 | 24 | 15 | 152 | 22 | 15 |
| 3 | 111 | 29 | 26 | 157 | 15 | 10 |
| 5 | 78 | 9 | 11 | 134 | 18 | 13 |
| 8 | 35 | 5 | 15 | 79 | 12 | 15 |

TABLE 7

Pharmacokinetic Parameters of d-amphetamine Following Oral Administration of d-amphetamine or L-lysine-d-amphetamine.

| | 1.5 mg/kg | | 3 mg/kg | | 6 mg/kg | |
|---|---|---|---|---|---|---|
| Parameter | d-amphetamine | L-lysine-d-amphetamine | d-amphetamine | L-lysine-d-amphetamine | d-amphetamine | L-lysine-d-amphetamine |
| AUC (ng/mlh) | 481 | 538 | 587 | 614 | 807 | 1005 |
| Percent | 100 | 112 | 100 | 105 | 100 | 125 |
| Cmax (ng/ml) | 133 | 93 | 587 | 614 | 807 | 1005 |

TABLE 7-continued

Pharmacokinetic Parameters of d-amphetamine Following Oral Administration of d-amphetamine or L-lysine-d-amphetamine.

| Parameter | 1.5 mg/kg | | 3 mg/kg | | 6 mg/kg | |
|---|---|---|---|---|---|---|
| | d-amphetamine | L-lysine-d-amphetamine | d-amphetamine | L-lysine-d-amphetamine | d-amphetamine | L-lysine-d-amphetamine |
| Percent | 100 | 70 | 100 | 105 | 100 | 125 |
| Tmax (hours) | 0.938 | 3.5 | 1 | 1.56 | 0.563 | 2.625 |
| Percent | 100 | 373 | 100 | 156 | 100 | 466 |

Example 8

Oral Bioavailability of L-lysine-d-amphetamine at Various Doses Approximating a Range of Therapeutic Human Doses Compared to a Suprapharmacological Male Sprague-Dawley rats were provided water ad libitum, fasted overnight and dosed by oral gavage with 1.5, 3, 6, 12, and 60 mg/kg of amphetamine sulfate or L-lysine-d-amphetamine containing the equivalent amounts of d-amphetamine. Concentrations of d-amphetamine were measured by ELISA.

It has been demonstrated that when lysine is conjugated to the active agent d-amphetamine the levels of d-amphetamine at 30 minutes past-administration are decreased by approximately 50% over a dosage range of 1.5 to 12 mg/kg. However, when a suprapharmacological dose (60 mg/kg) is given, the levels of d-amphetamine from L-lysine-d-amphetamine only reached 8% of those seen for d-amphetamine sulfate (Tables 8 and 9, FIG. 10). The substantial decrease in oral bioavailability at a high dose greatly reduces the abuse potential of L-lysine-d-amphetamine.

TABLE 8

Levels of d-amphetamine vs. Dosage at 0.5 h Post Dosing with d-amphetamine Sulfate.

| Dose mg/kg | 1.5 | 3 | 6 | 12 | 60 |
|---|---|---|---|---|---|
| ng/ml 0.5 h | 109 +/− 59 | 196 +/− 72 | 294 +/− 202 | 344 +/− 126 | 3239 +/− 73 |
| Percent | 100 | 100 | 100 | 100 | 100 |

TABLE 9

Levels of d-amphetamine vs. Dosage at 0.5 h Post Dosing with L-lysine-d-amphetamine.

| Dose mg/kg | 1.5 | 3 | 6 | 12 | 60 |
|---|---|---|---|---|---|
| ng/ml 0.5 h | 45 +/− 10 | 86 +/− 26 | 129 +/− 46 | 172 +/− 113 | 266 +/− 18 |
| Percent | 41 | 44 | 44 | 50 | 8 |

Example 9

Decreased Oral Bioavailability of L-lysine-d-amphetamine at a High Dose

Figure 11:
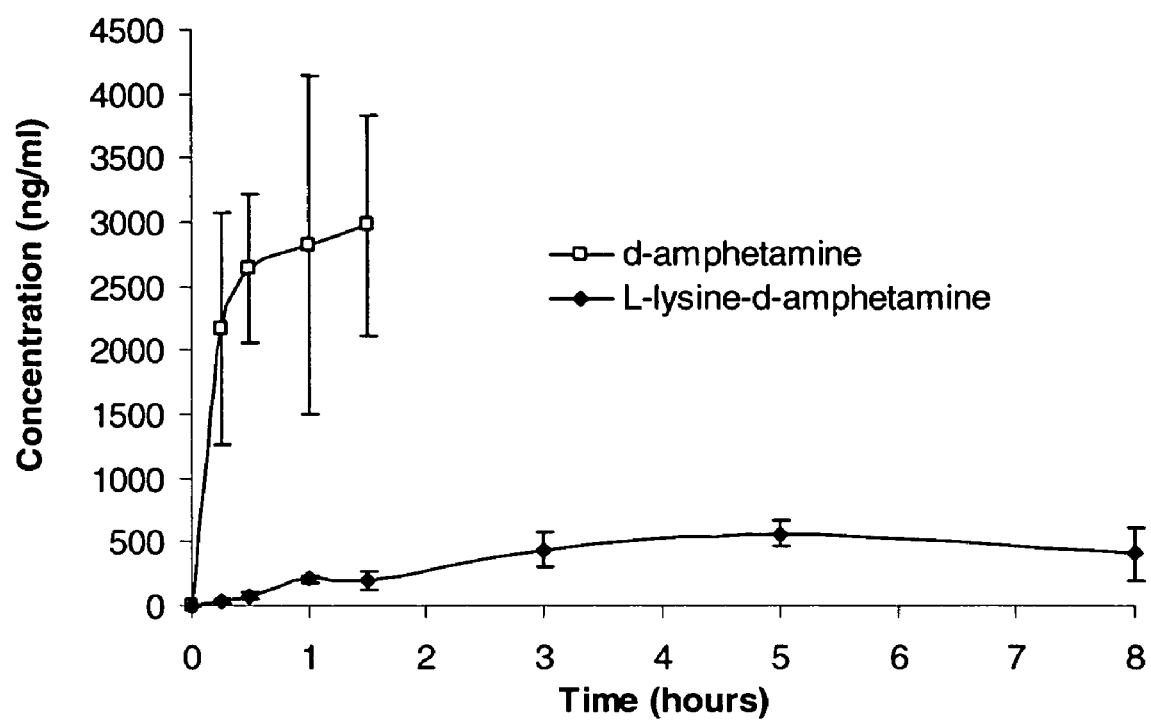
FIG. 11. Plasma concentrations of d-amphetamine following oral administration of L-lysine-d-amphetamine or d-amphetamine sulfate (60 mg/kg d-amphetamine base) to rats (ELISA analysis).

An additional oral PK study illustrated in FIG. 11 shows the d-amphetamine blood levels of a 60 mg/kg dose over an 8 h time course. In the case of d-amphetamine blood levels quickly reached a very high level and 8 of 12 animals either died or were sacrificed due to acute symptoms of toxicity. Blood levels (Tables 10–11) of animals administered L-lysine-d-amphetamine, on the other hand, did not peak until 5 hours and reached only a fraction of the levels of the animals receiving amphetamine (note: valid data past 3 h for d-amphetamine could not be determined due to death and sacrifice of animals).

TABLE 10

Mean Plasma Concentrations of d-amphetamine vs. L-lysine-d-amphetamine Following Oral Administration of a High Dose (60 mg/kg).

| | Plasma Amphetamine Concentrations (ng/ml) | | | | | |
|---|---|---|---|---|---|---|
| | d-amphetamine | | | L-lysine-d-amphetamine | | |
| Hours | Mean | +/− SD | CV | Mean | +/− SD | CV |
| 0 | NA | NA | NA | NA | NA | NA |
| 0.25 | 2174 | 907 | 42 | 35 | 17 | 48 |
| 0.5 | 2643 | 578 | 22 | 81 | 33 | 41 |
| 1 | 2828 | 1319 | 47 | 212 | 30 | 14 |
| 1.5 | 2973 | 863 | 29 | 200 | 79 | 40 |
| 3 | 2944 | 95 | 3 | 440 | 133 | 30 |
| 5 | NA | NA | NA | 565 | 100 | 18 |
| 8 | NA | NA | NA | 410 | 206 | 50 |

TABLE 11

Pharmacokinetic Parameters of d-amphetamine vs. L-lysine-d-amphetamine

| Drug | AUC ng/ml h | Percent d-amphetamine | Cmax (ng/ml) | Percent d-amphetamine | Mean Peak (ng/ml) | Percent d-amphetamine |
|---|---|---|---|---|---|---|
| d-mphetamine | 8,130 | 100 | 3623 | 100 | 2973 | 100 |
| L-lysine-d-amphetamine | 3,143 | 39 | 582 | 16 | 565 | 19 |

Example 10

Figure 14:
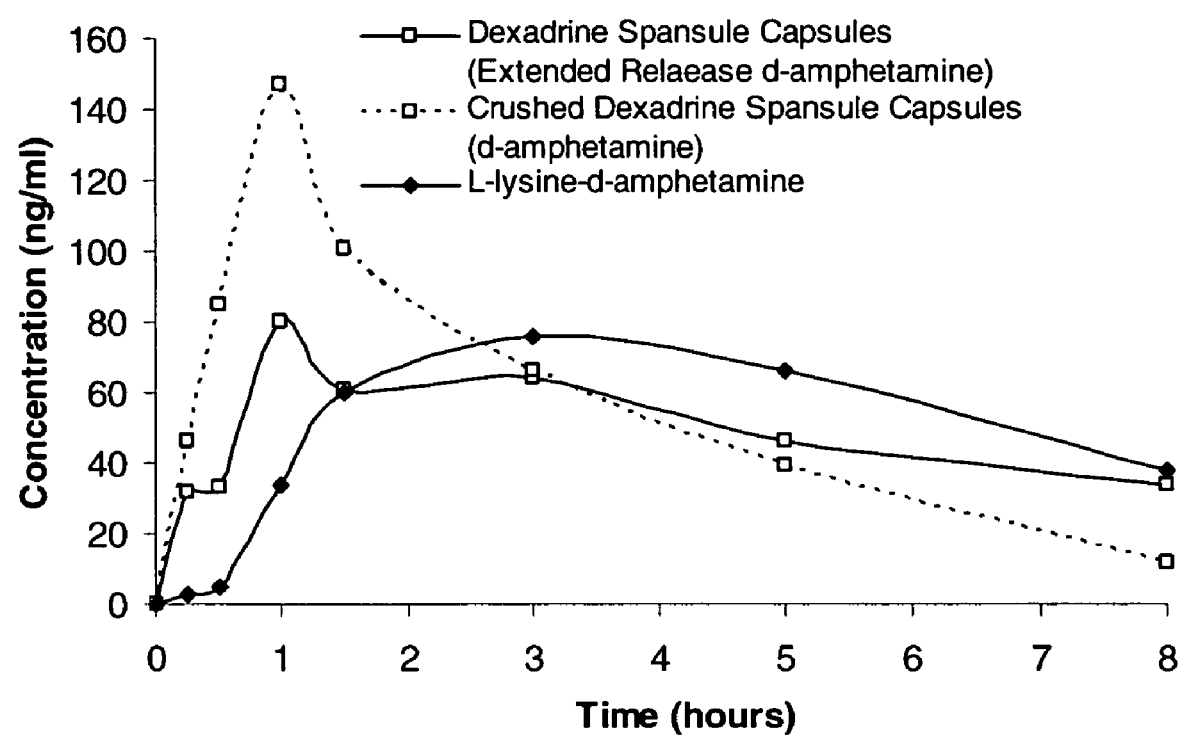
FIG. 14. Plasma concentrations of d-amphetamine levels following oral administration of Dexadrine Spansule capsules, crushed Dexadrine Spansule capsules, or L-lysine-d-amphetamine (3 mg/kg d-amphetamine base) to rats (ELISA analysis).
Figure 15A:
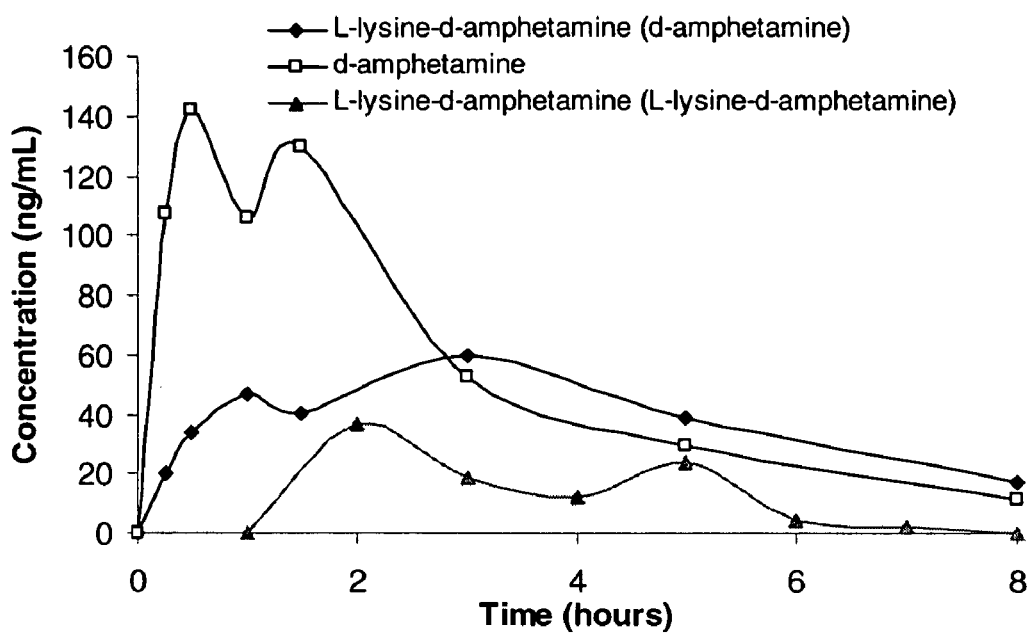
FIGS. 15A–B. Plasma concentrations of d-amphetamine in ng/mL (FIG. 15A), and in uM (FIG. 15B), following oral administration of L-lysine-d-amphetamine or d-amphetamine sulfate (1.5 mg/kg d-amphetamine base) to rats (LC/MS/MS analysis).
Figure 15B:
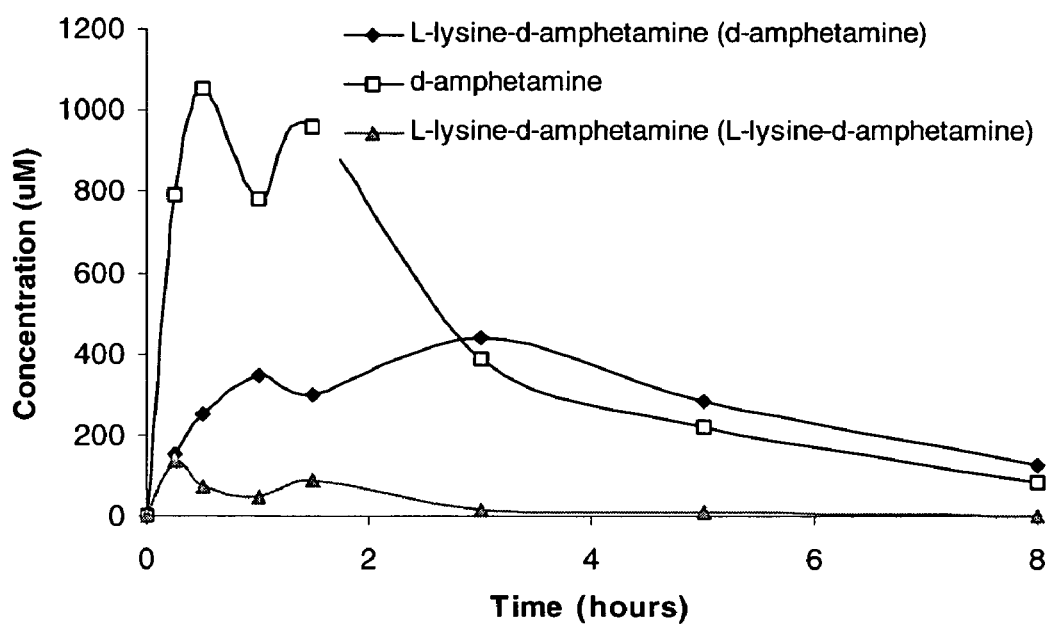
Figure 16A:
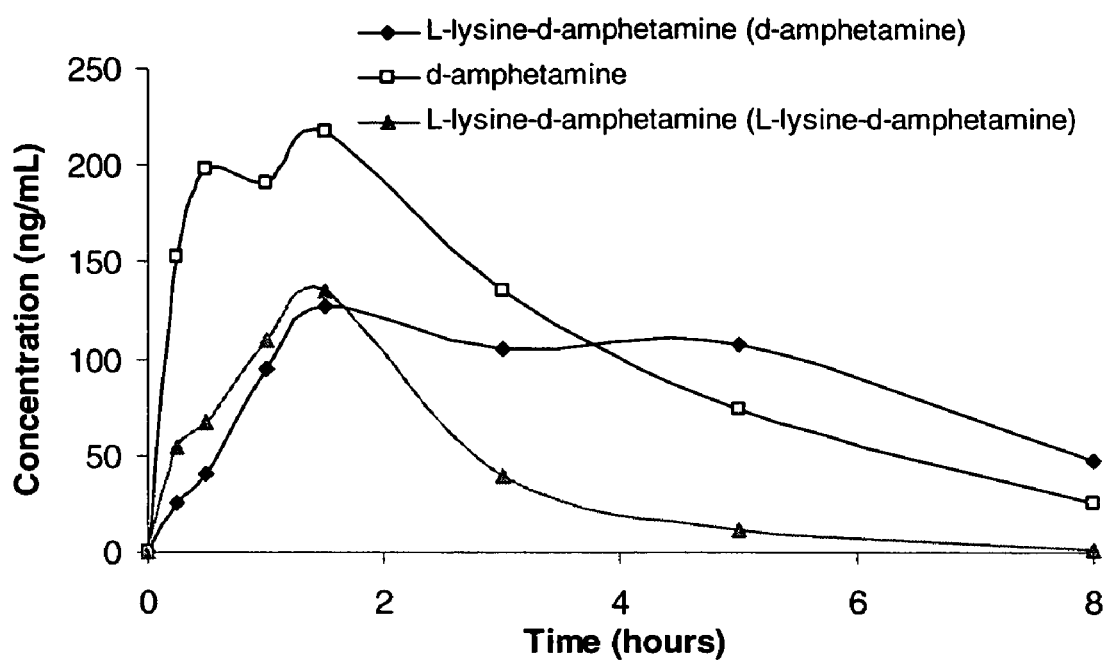
FIGS. 16A–B. Plasma concentrations of d-amphetamine in ng/mL (FIG. 16A), and in uM (FIG. 16B), following oral administration of L-lysine-d-amphetamine or d-amphetamine sulfate (3 mg/kg d-amphetamine base) to rats (LC/MS/MS analysis).
Figure 16B:
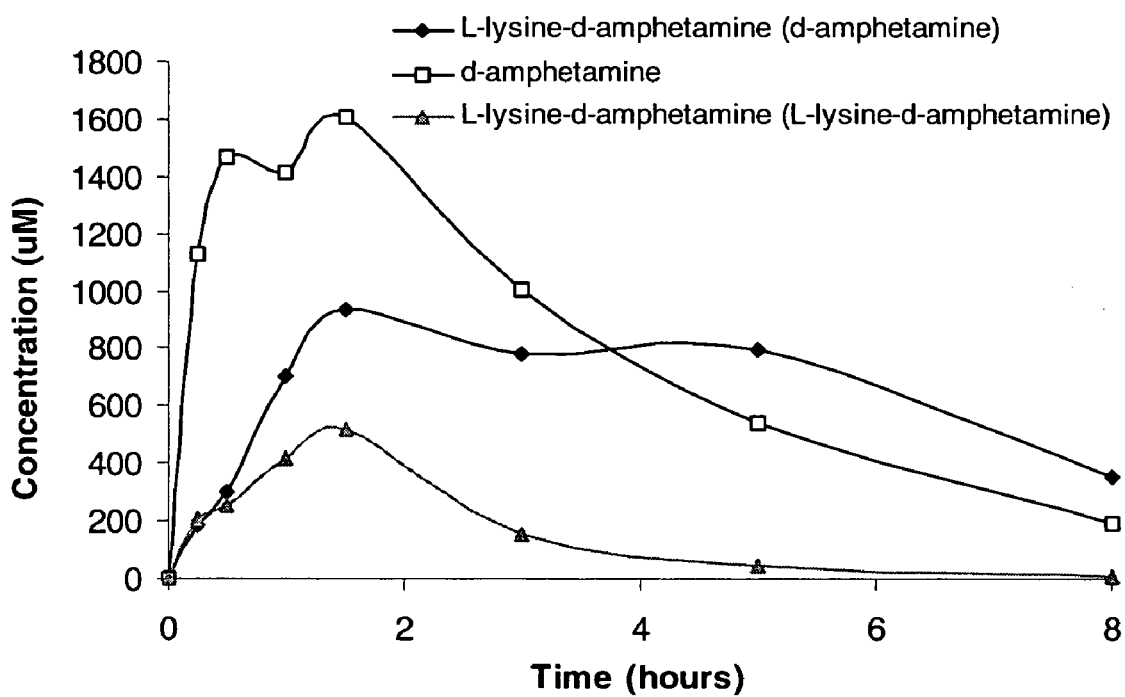
Figure 17A:
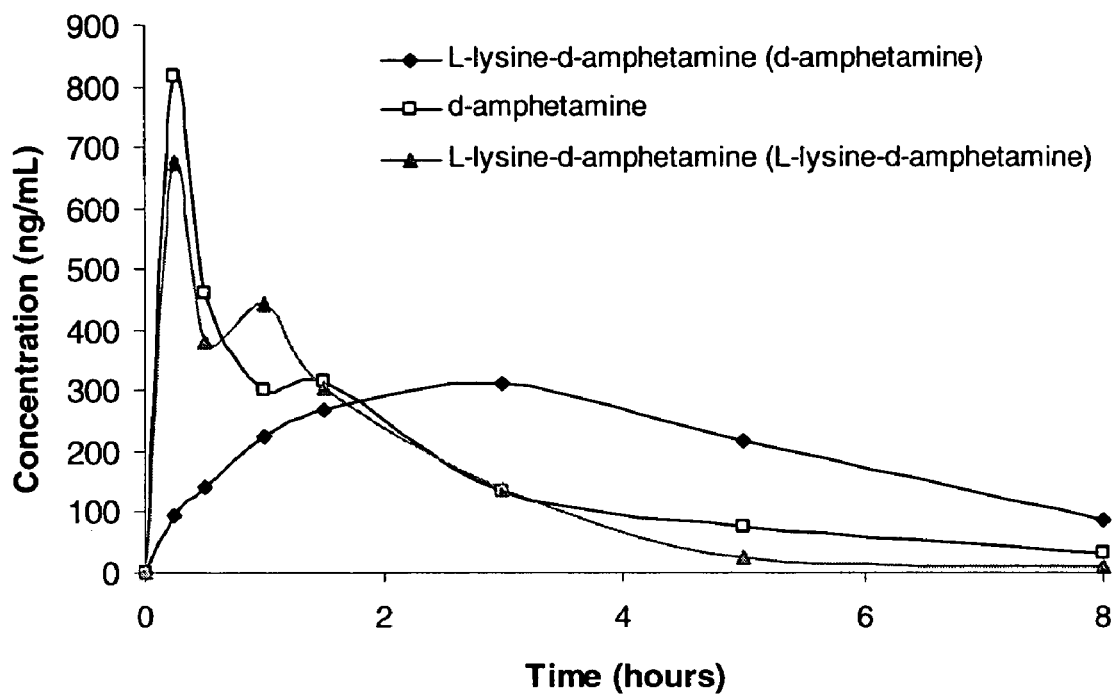
FIGS. 17A–B. Plasma concentrations of d-amphetamine in ng/mL (FIG. 17A), and in uM (FIG. 17B), following oral administration of L-lysine-d-amphetamine or d-amphetamine sulfate (6 mg/kg d-amphetamine base) to rats (LC/MS/MS analysis).
Figure 17B:
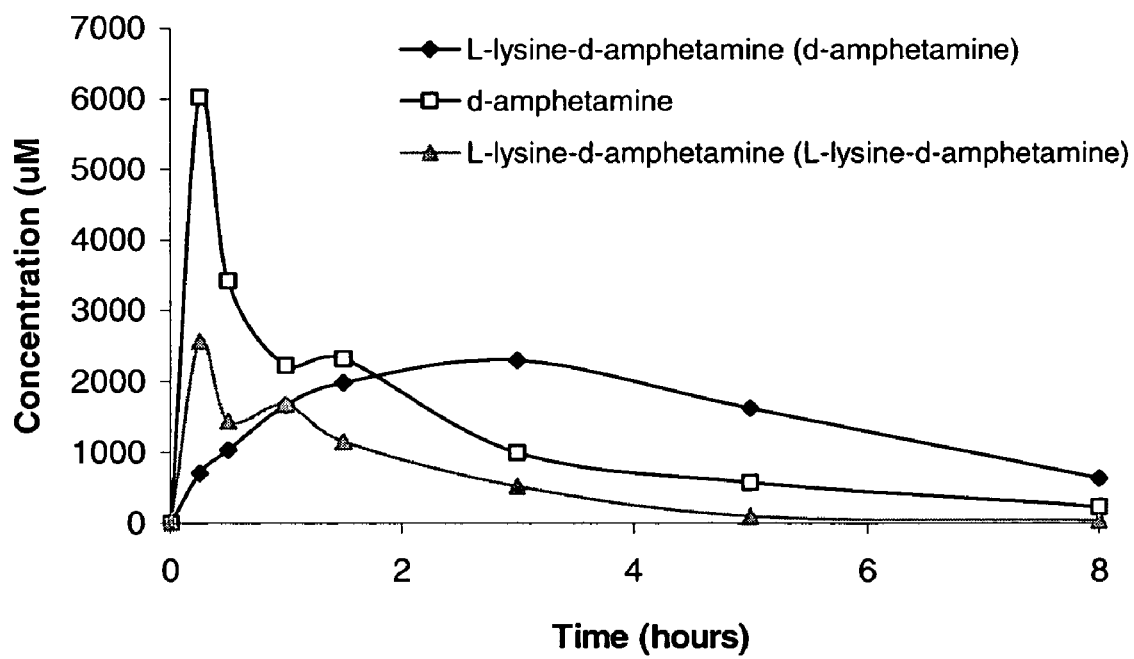
Figure 18A:
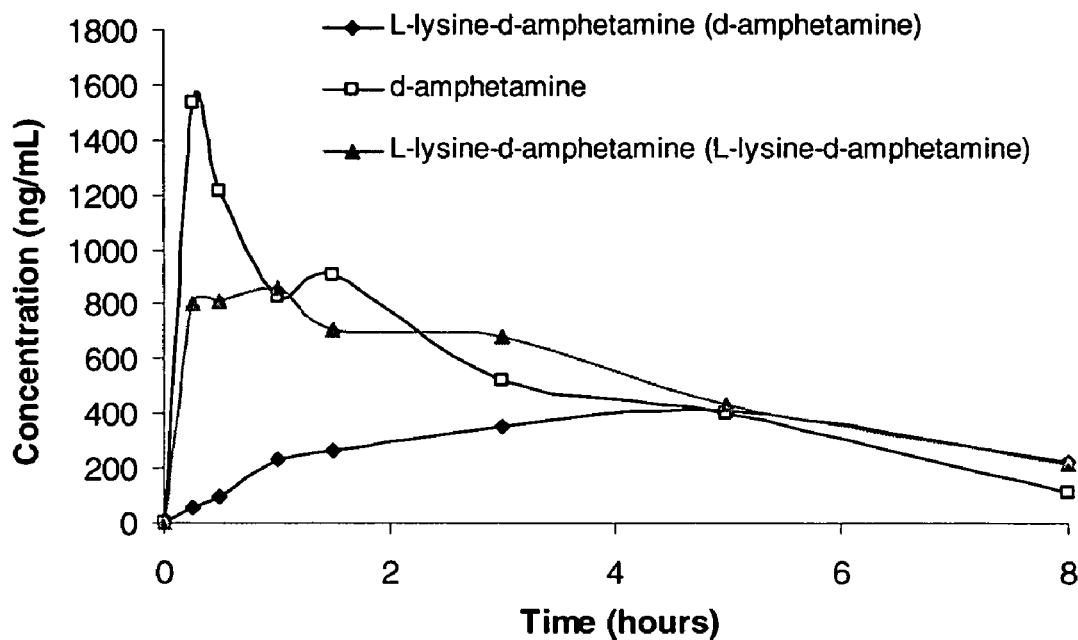
FIGS. 18A–B. Plasma concentrations of d-amphetamine in ng/mL (FIG. 18A), and in uM (FIG. 18B), following oral administration of L-lysine-d-amphetamine or d-amphetamine sulfate (12 mg/kg d-amphetamine base) to rats (LC/MS/MS analysis).
Figure 18B:
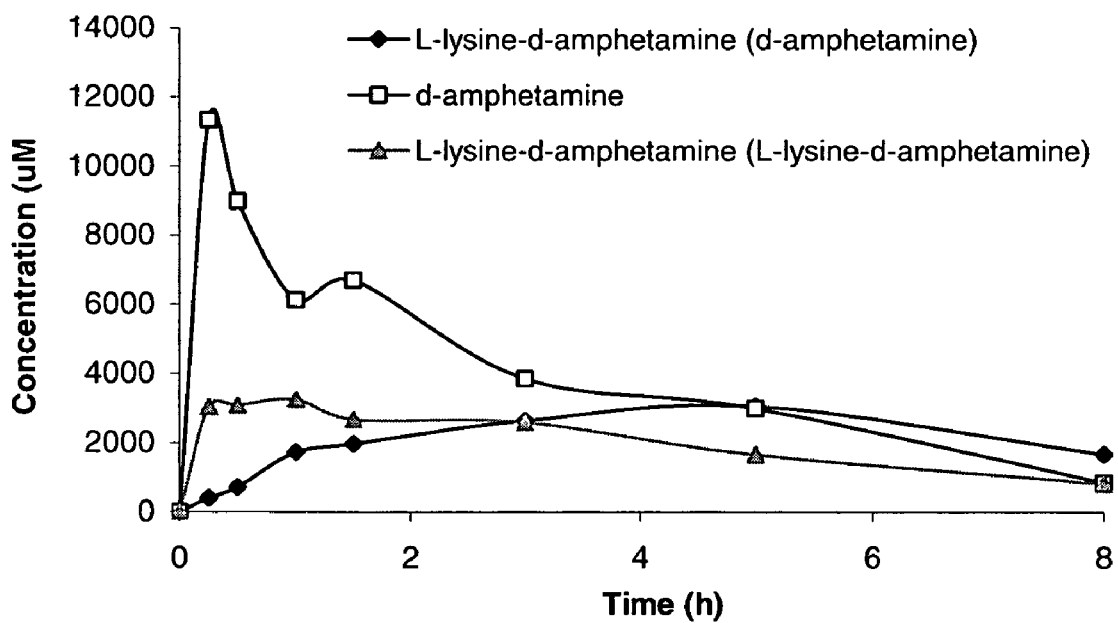
Figure 19A:
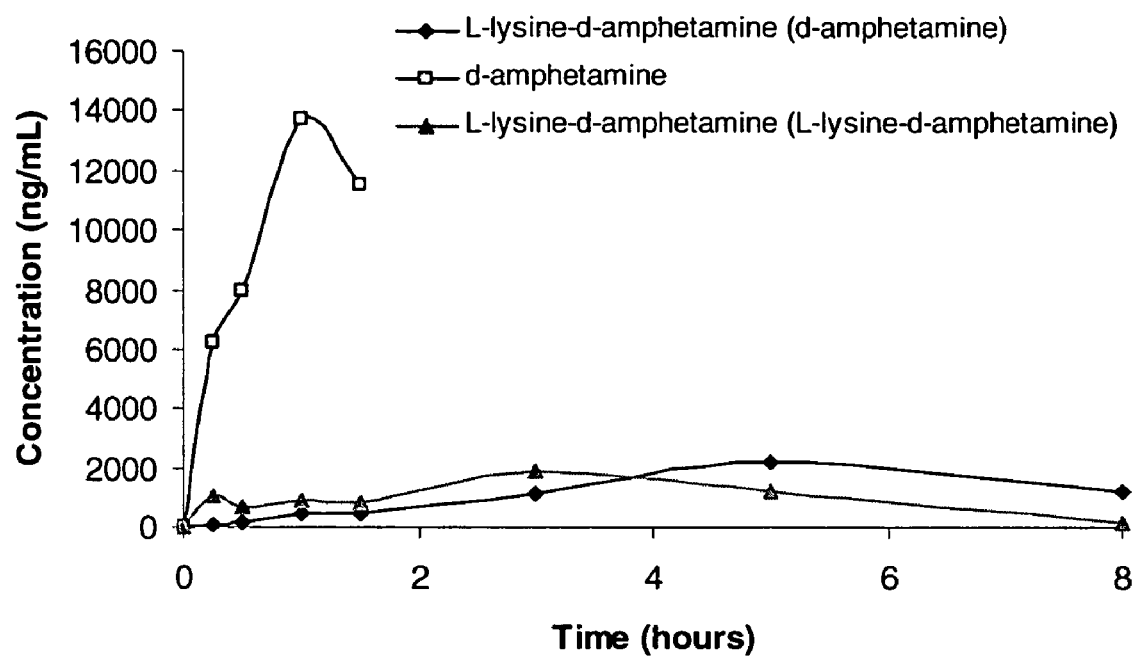
FIGS. 19A–B. Plasma concentrations of d-amphetamine in ng/mL (FIG. 19A), and in uM (FIG. 19B), following oral administration of or d-amphetamine sulfate (60 mg/kg d-amphetamine base) to rats (LC/MS/MS analysis).
Figure 19B:
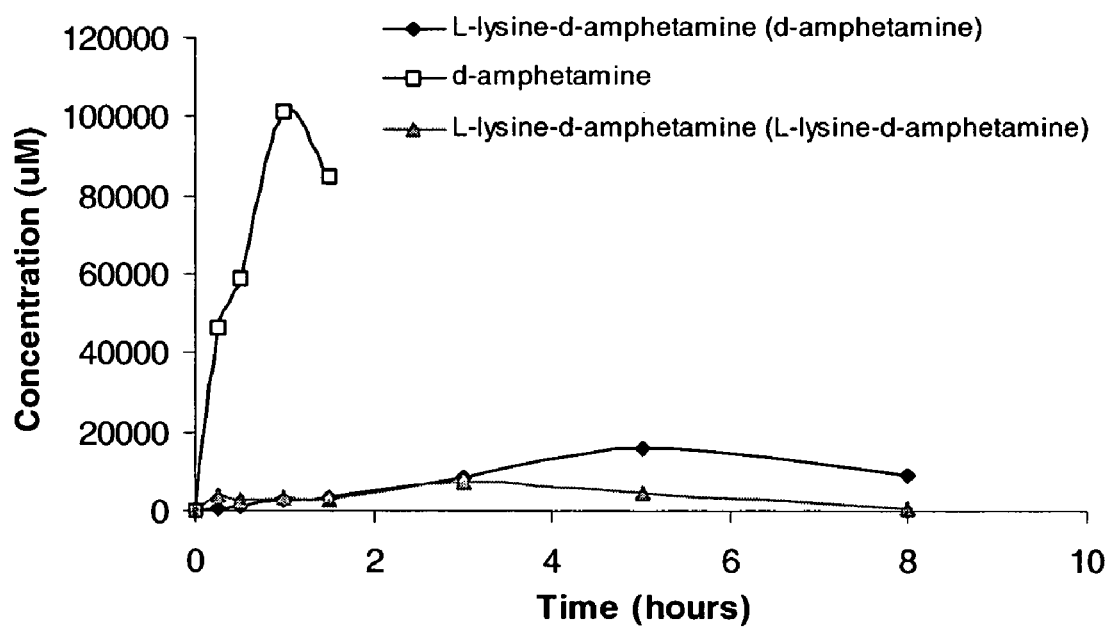

Oral Bioavailability of d-amphetamine Following Administration of an Extended Release Formulation (Intact or Crushed) or L-lysine-d-amphetamine Doses of an extended release formulation of d-amphetamine sulfate (Dexadrine Spansule® capsules) (GlaxoSmithKline) were orally administered to rats as intact capsules or as rushed capsules and compared to a dose of L-lysine-d-amphetamine containing an equivalent amount of d-amphetamine base (FIG. 14). The crushed capsules showed an increase in $C_{max}$ and $AUC_{inf}$ of 84 and 13 percent, respectively, as compared to intact capsules (Tables 12–13). In contrast, $C_{max}$ and $AUC_{inf}$ of d-amphetamine following administration of L-lysine-d-amphetamine were similar to that of the intact capsule illustrating that extended release is inherent to the compound itself and can not be circumvented by simple manipulation.

TABLE 12

Time-course Concentrations of d-amphetamine Following Oral Administration of Extended Release Dexadrine Spansule Capsules or Crushed Extended Release Dexadrine Spansule Capsules or L-lysine-d-amphetamine at Doses Containing 3 mg/kg d-Amphetamine Base.

| | Plasma Concentration (ng/ml) | | |
|---|---|---|---|
| Hours | Intact Spansule Capsule | Crushed Spansule Capsule | L-lysine-d-amphetamine |
| 0 | 0 | 0 | 0 |
| 0.25 | 32 | 46 | 3 |
| 0.5 | 33 | 85 | 5 |
| 1 | 80 | 147 | 34 |
| 1.5 | 61 | 101 | 60 |
| 3 | 64 | 66 | 76 |
| 5 | 46 | 39 | 66 |
| 8 | 34 | 12 | 38 |

TABLE 13

Time-course Concentrations of d-amphetamine Following Oral Administration of Extended Release Dexadrine Spansule Capsules or Crushed Extended Release Dexadrine Spansule Capsules or L-lysine-d-amphetamine at Doses Containing 3 mg/kg d-Amphetamine Base.

| Parameter | Intact Spansule Capsule | Crushed Spansule Capsule | L-lysine-d-amphetamine |
|---|---|---|---|
| $AUC_{0-8h}$ (ng · h/ml) | 399 | 449 | 434 |
| Percent | 100 | 113 | 109 |
| $C_{max}$ (ng/ml) | 80 | 147 | 76 |
| Percent | 100 | 184 | 95 |
| $T_{max}$ (hours) | 1 | 1 | 3 |
| Percent | 100 | 100 | 300 |

Example 10 illustrates the advantage of the invention over conventional controlled release formulations of d-amphetamine.

Example 11

Decreased Intranasal Bioavailability of L-lysine-d-amphetamine vs. Amphetamine

Figure 12:
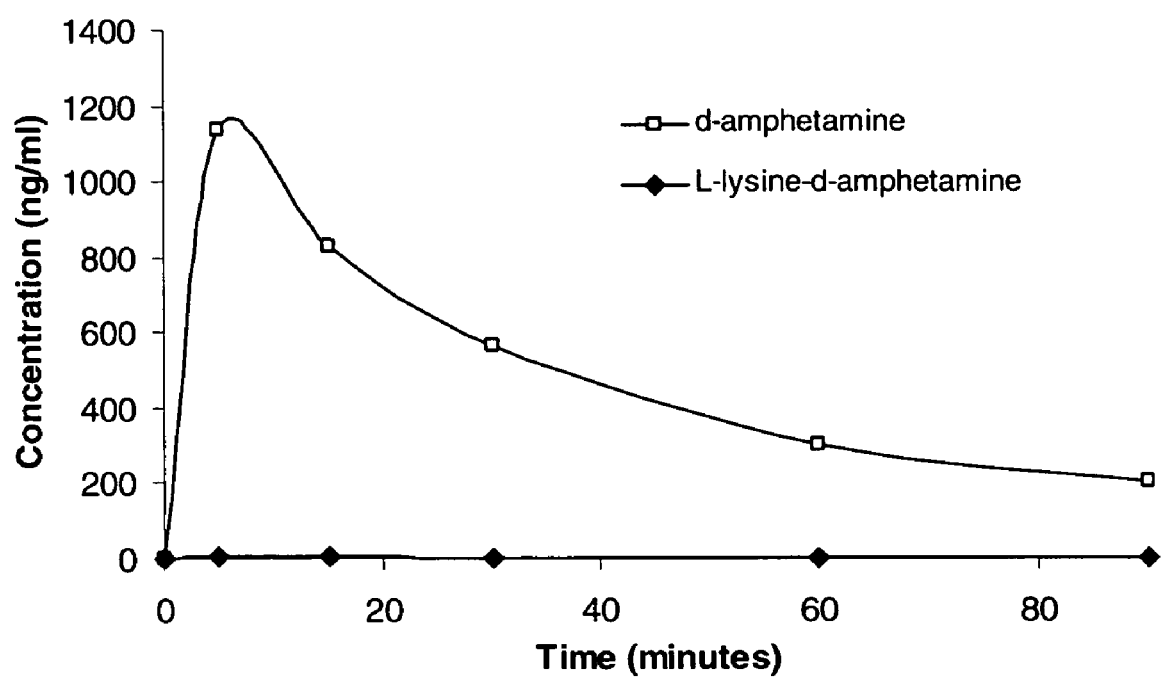
FIG. 12. Plasma concentrations of d-amphetamine following intranasal administration of L-lysine-d-amphetamine or d-amphetamine sulfate (3 mg/kg d-amphetamine base) to rats (ELISA analysis).

Male Sprague-Dawley rats were dosed by intranasal administration with 3 mg/kg of amphetamine sulfate or L-lysine-d-amphetamine hydrochloride containing the equivalent amounts of d-amphetamine. L-lysine-d-amphetamine did not release any significant amount of d-amphetamine into circulation by IN administration. Mean (n=4) plasma amphetamine concentration curves of amphetamine vs. L-lysine-d-amphetamine are shown in FIG. 12. Pharmacokinetic parameters for IN administration of L-lysine-d-amphetamine are summarized in Table 14.

TABLE 14

Pharmacokinetic Parameters of Amphetamine vs. L-lysine-d-amphetamine by IN Administration.

| Drug | AUC (0–1.5 h) ng/ml h | Percent d-amphetamine | Cmax (ng/ml) | Percent d-amphetamine |
|---|---|---|---|---|
| Amphetamine | 727 | 100 | 1,377 | 100 |
| L-lysine-d-amphetamine | 4 | 0.5 | 7 | 0.5 |

Example 11 illustrates that when lysine is conjugated to the active agent d-amphetamine the bioavailability by the intranasal route is substantially decreased thereby diminishing the ability to abuse the drug by this route.

Example 12

Intravenous Bioavailability of Amphetamine vs. L-lysine-d-amphetamine

Figure 13:
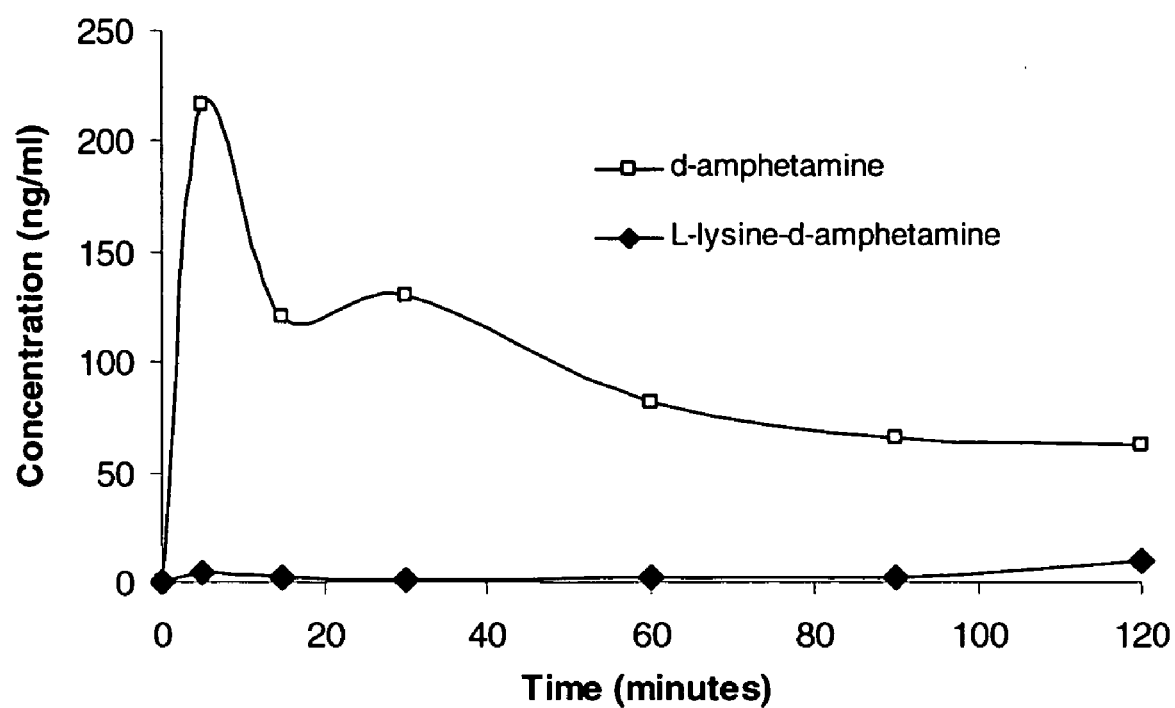
FIG. 13. Plasma concentrations of d-amphetamine following bolus intravenous administration of L-lysine-d-amphetamine or d-amphetamine sulfate (1.5 mg/kg d-amphetamine base) to rats (ELISA analysis).

Male Sprague-Dawley rats were dosed by intravenous tail vein injection with 1.5 mg/kg of d-amphetamine or L-lysine-d-amphetamine containing the equivalent amount of amphetamine. As observed with IN dosing, the conjugate did not release a significant amount of d-amphetamine. Mean (n=4) plasma concentration curves of amphetamine vs. L-lysine-d-amphetamine are shown in FIG. 13. Pharmacokinetic parameters for IV administration of L-lysine-d-amphetamine are summarized in Table 15.

TABLE 15

Pharmacokinetic Parameters of d-amphetamine vs. L-lysine-d-amphetamine by IV Administration.

| Drug | AUC (0–1.5 h) ng/ml h | % Amphetamine | Cmax (ng/ml) | % Amphetamine |
|---|---|---|---|---|
| Amphetamine | 190 | 100 | 169 | 100 |
| K-amphetamine | 6 | 3 | 5 | 3 |

Example 12 illustrates that when lysine is conjugated to the active agent amphetamine the bioavailability of amphetamine by the intravenous route is substantially decreased, thereby diminishing the ability to abuse the drug by this route.

Example 13.

Oral Bioavailability of L-lysine-d-amphetamine Compared to d-amphetamine at Escalating Doses.

As shown in FIGS. 15–19, the fraction of intact L-lysine-d-amphetamine absorbed following oral administration in rats increased non-linearly in proportion to escalating doses from 1.5 to 12 mg/kg (d-amphetamine base). The fraction absorbed at 1.5 mg/kg was only 2.6 percent whereas it increased to 24.6 percent by 12 mg/kg. The fraction absorbed fell to 9.3 percent at the high dose of 60 mg/kg. $T_{max}$ ranged from 0.25 to 3 hours and peak concentrations occurred earlier than for d-amphetamine in L-lysine-d- amphetamine dosed rats. L-lysine-d-amphetamine was cleared more rapidly than d-amphetamine with nearly undetectable concentrations by 8 hours at the lowest dose.

$T_{max}$ for d-amphetamine from L-lysine-d-amphetamine ranged from 1.5 to 5 hours as compared to 0.5 to 1.5 following administration of d-amphetamine sulfate. The difference in time to reach maximum concentration was greater at higher doses. $C_{max}$ of d-amphetamine following oral delivery of L-lysine-d-amphetamine was reduced by approximately half as compared to $C_{max}$ following d-amphetamine sulfate administration at doses of 1.5 to 6 mg/kg, approximating human equivalent doses (HEDs) in the therapeutic range (HED d-amphetamine sulfate; 19.9 to 39.9 mg). HEDs are defined as the equivalent dose for a 60 kg person in accordance to the body surface area of the animal model. The adjustment factor for rats is 6.2. The HED for a rat dose of 1.5 mg/kg of d-amphetamine, for example, is equivalent to 1.5/6.2×60=14.52 d-amphetamine base; which is equivalent to 14.52/0.7284=19.9 mg d-amphetamine sulfate, when adjusted for the salt content.

At doses above HEDs in the targeted therapeutic range (12 and 60 mg/kg; HED d-amphetamine sulfate 79.8 and 399 mg), $C_{max}$ was reduced by 73 and 84 percent, respectively, as compared to d-amphetamine sulfate. AUCs of d-amphetamine following oral administration of L-lysine-d-amphetamine were similar to those of d-amphetamine sulfate at lower doses. As observed with $C_{max}$, however, the AUCs for d-amphetamine from L-lysine-d-amphetamine were substantially decreased compared to those of d-amphetamine sulfate at higher doses with the $AUC_{inf}$ reduced by 76% at the highest dose (60 mg/kg; HED d-amphetamine sulfate 399 mg).

In summary, oral bioavailability of d-amphetamine from L-lysine-d-amphetamine decreased to some degree at higher doses in rats. However, phannacokinetics with respect to dose were nearly linear for L-lysine-d-amphetamine at doses from 1.5 to 60 mg/kg (HED d-amphetamine sulfate; 19.9 to 797.2 mg) with the fraction absorbed ranging from 52 to 81 percent (extrapolated from 1.5 mg/kg dose). Pharmacokinetics of d-amphetamine sulfate was also nearly linear at lower doses of 1.5 to 6 mg/kg (HED; 19.9 to 79.7) with the fraction absorbed ranging from 62 to 84. In contrast to L-lysine-d-amphetamine, however, parameters were disproportionately increased at higher doses for d-amphetamine sulfate with the fraction absorbed calculated as 101 and 223 percent (extrapolated fefifi from 1.5 mg/kg dose), respectively, for the suprapharmacological doses of 12 and 60 mg/kg (HED d-amphetamine sulfate; 159.4 and 797.2 mg).

Figure 20:
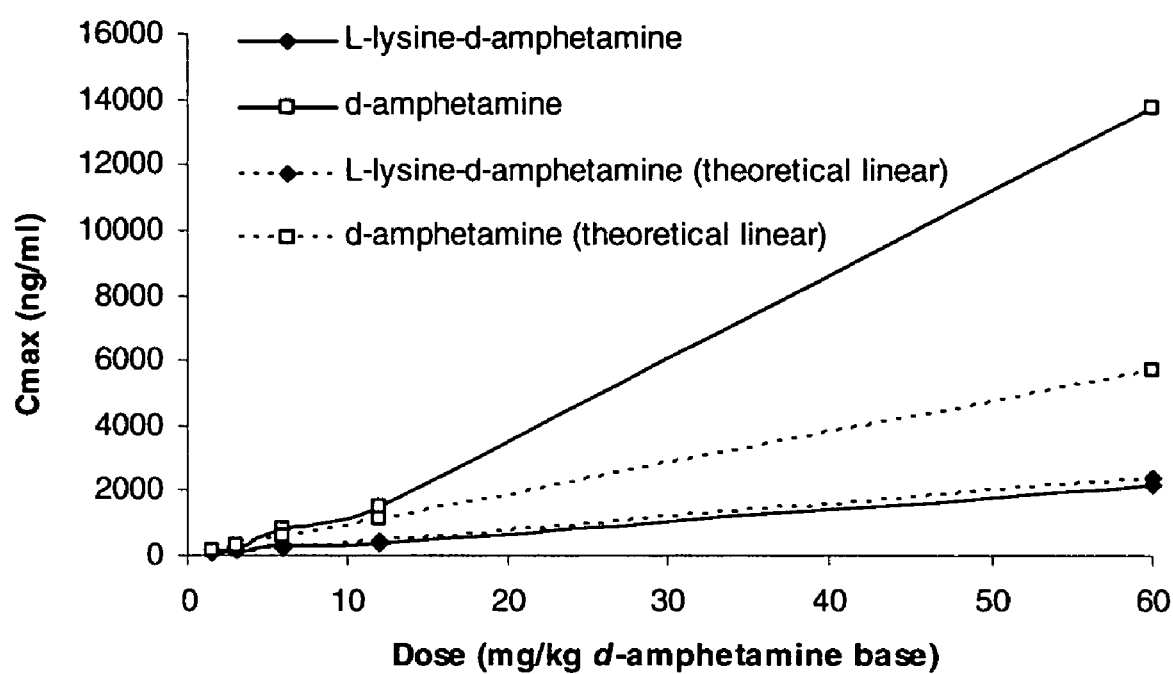
FIG. 20. Comparative bioavailability ($C_{max}$) of L-lysine-d-amphetamine and d-amphetamine in proportion to escalating human equivalent doses in rats (mg/kg d-amphetamine base).
Figure 21:
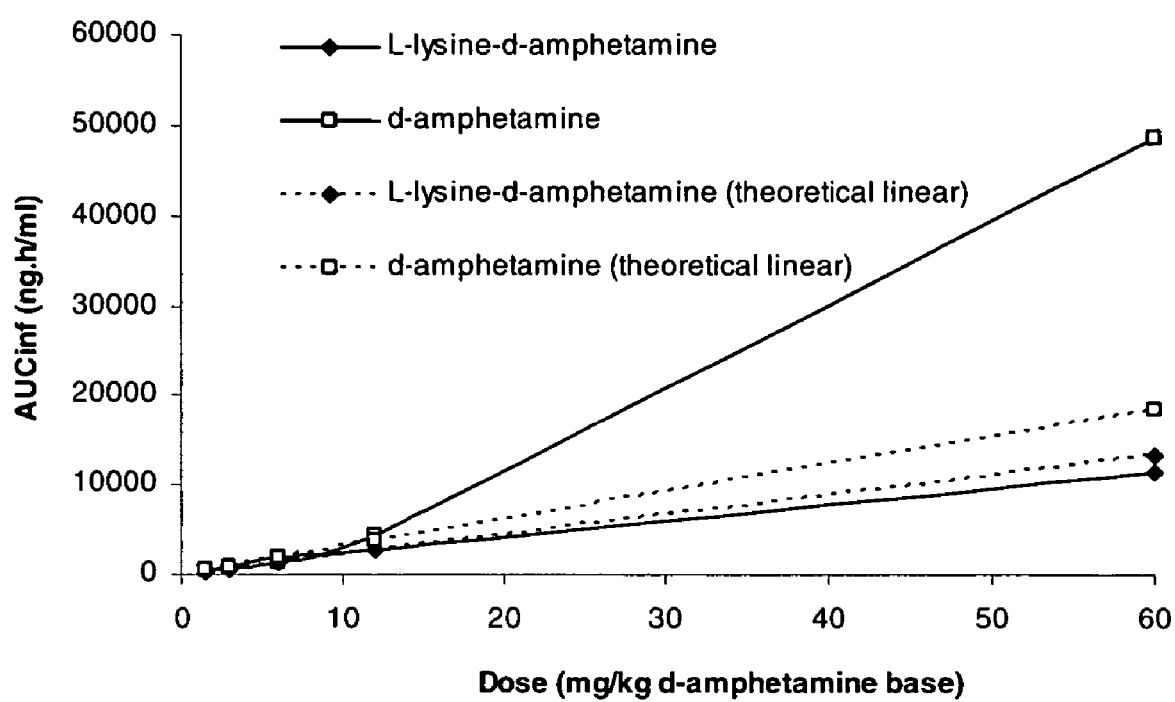
FIG. 21. Comparative bioavailability ($AUC_{inf}$) of L-lysine-d-amphetamine and d-amphetamine in proportion to escalating doses in rats (mg/kg d-amphetamine base).
Figure 22:
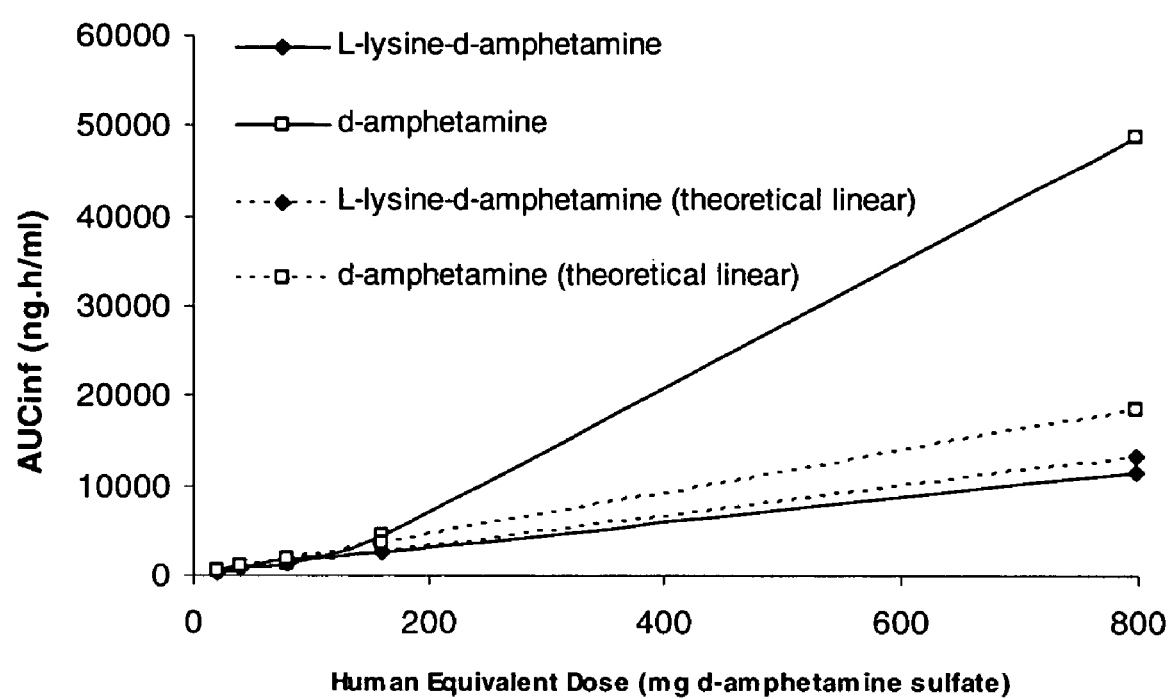
FIG. 22. Comparative bioavailability ($AUC_{inf}$) of L-lysine-d-amphetamine and d-amphetamine in proportion to escalating human equivalent doses in rats (mg/kg d-amphetamine base).

The results suggest that the capacity for clearance of d-amphetamine when delivered as the sulfate salt becomes saturated at the higher doses whereas the gradual hydrolysis of L-lysine-d-amphetamine precludes saturation of d-amphetamine elimination at higher doses. The difference in proportionality of dose to bioavailability ($C_{max}$ and AUC) for d-amphetamine and L-lysine-d-amphetamine is illustrated in FIGS. 20–22. The pharmacokinetic properties of L-lysine-d-amphetamine as compared to d-amphetamine at the higher doses decrease the ability to escalate doses. This improves the safety and reduces the abuse liability of L-lysine-d-amphetamine as a method of delivering d-amphetamine for the treatment of ADHD or other indicated conditions.

Example 14

Intranasal Bioavailability of L-lysine-d-amphetamine Compared to d-amphetamine

Figure 23:
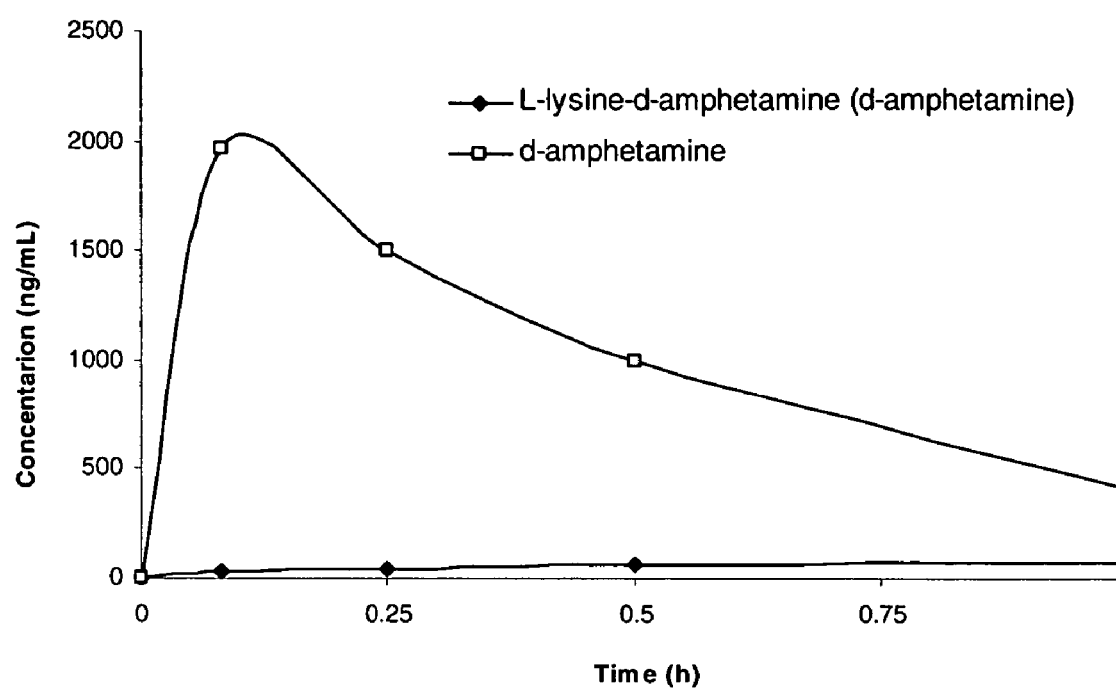
FIG. 23. Plasma concentrations of d-amphetamine following intranasal administration of L-lysine-d-amphetamine or d-amphetamine sulfate (3 mg/kg d-amphetamine base) to rats (LC/MS/MS analysis).
Figure 24A:
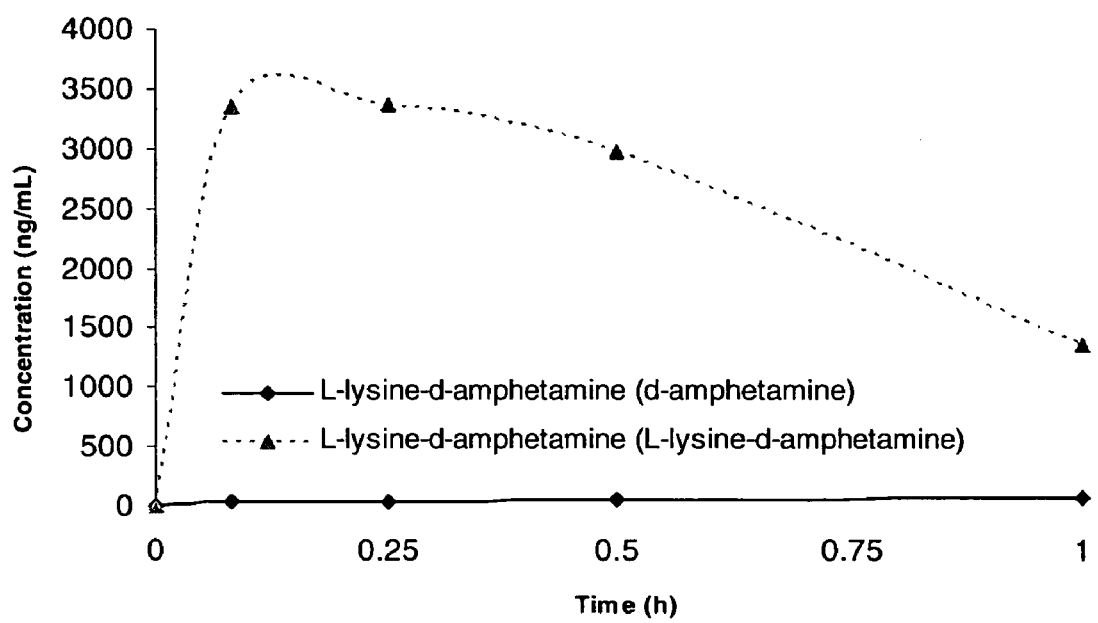
FIG. 24. Plasma concentrations of d-amphetamine and L-lysine-d-amphetamine in ng/mL (FIG. 24A), and in μM (FIG. 24B), following intranasal administration of L-lysine-d-amphetamine or d-amphetamine sulfate (3 mg/kg d-amphetamine base) to rats (LC/MS/MS analysis).
Figure 24B:
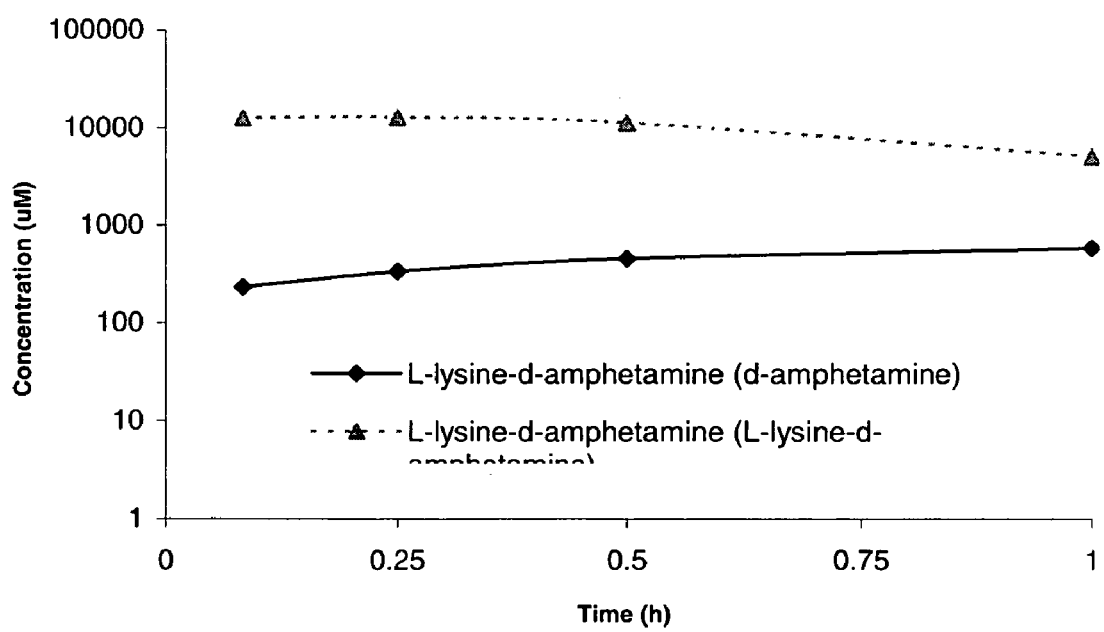

As shown in FIGS. 23–24, bioavailability of d-amphetamine following bolus intranasal administration of L-lysine-d-amphetamine was approximately 5 percent of that of the equivalent d-amphetamine sulfate dose with $AUC_{inf}$ values of 56 and 1032, respectively. $C_{max}$ of d-amphetamine following L-lysine-d-amphetamine administration by the intranasal route was also about 5 percent of that of the equivalent amount of d-amphetamine sulfate with values of 78.6 ng/mL and 1962.9 ng/mL, respectively. As with intravenous administration, $T_{max}$ of d-amphetamine concentration was delayed substantially for L-lysine-d-amphetamine (60 minutes) as compared to $T_{max}$ of d-amphetamine sulfate (5 minutes), again reflecting the gradual hydrolysis of L-lysine-d-amphetamine. A high concentration of intact L-lysine-d-amphetamine was detected following intranasal dosing suggesting that the large decrease in bioavailability of d-amphetamine was due to minimal hydrolysis of L-lysine-d-amphetamine when delivered by this route. It appears that only minimal amounts of d-amphetamine can be delivered by intranasal administration of L-lysine-d-amphetamine.

Example 15.

Intravenous Bioavailability of L-lysine-d-amphetamine Compared to d-amphetamine at Escalating Doses.

Figure 25:
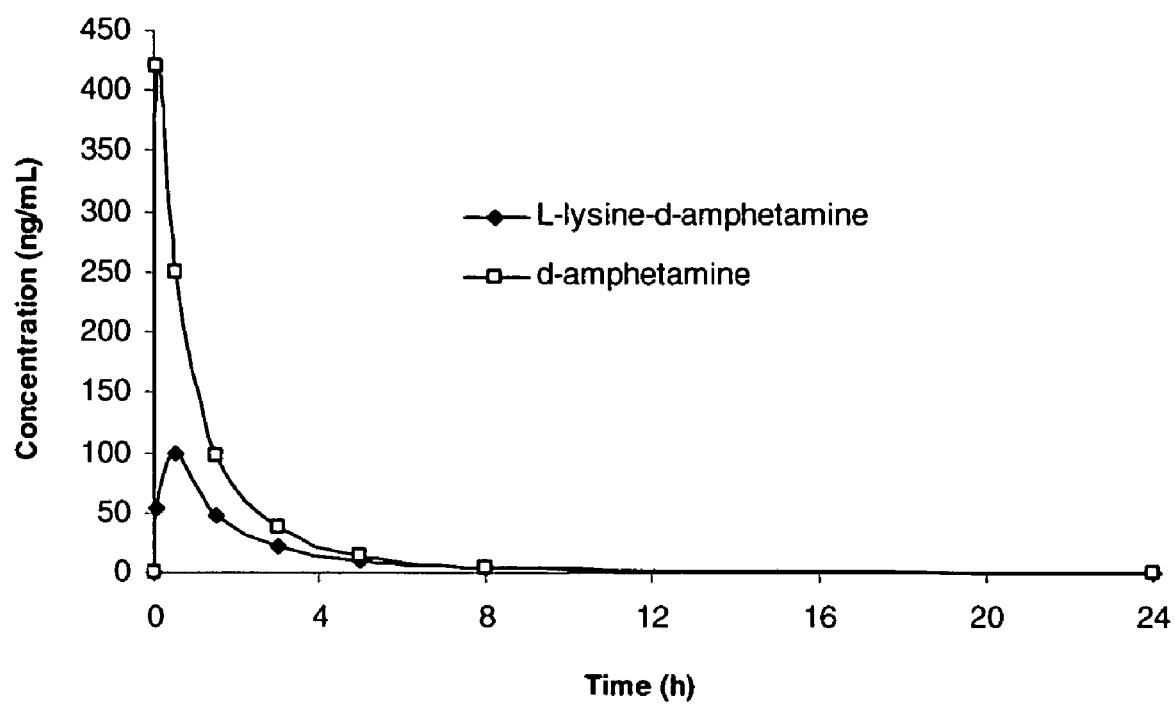
FIG. 25. Plasma concentrations of d-amphetamine following bolus intravenous administration of L-lysine-d-amphetamine or d-amphetamine sulfate (1.5 mg/kg d-amphetamine base) to rats (LC/MS/MS analysis).
Figure 26A:
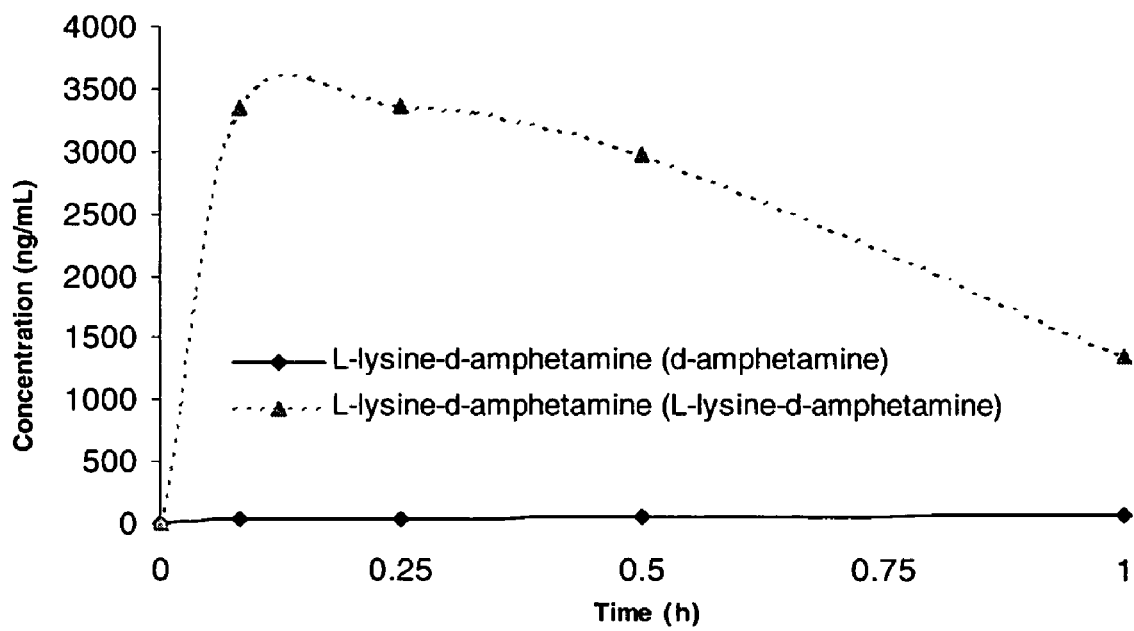
FIGS. 26A–B. Plasma concentrations of d-amphetamine in ng/mL (FIG. 26A), and in μM (FIG. 26B), following intranasal administration of L-lysine-d-amphetamine or d-amphetamine sulfate (3 mg/kg d-amphetamine base) to rats (LC/MS/MS analysis).
Figure 26B:
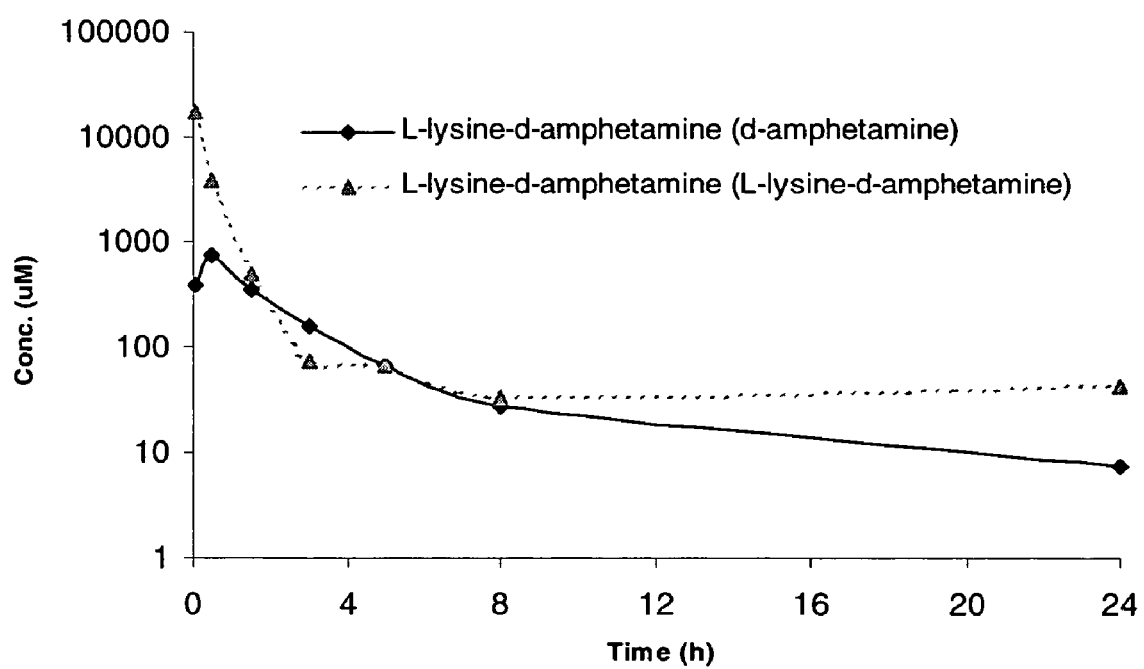

As shown in FIGS. 25–26, bioavailability of d-amphetamine following bolus intravenous administration of L-lysine-d-amphetamine was approximately one-half that of the equivalent d-amphetamine sulfate dose with $AUC_{inf}$ values of 237.8 and 420.2, respectively. $C_{max}$ of d-amphetamine following L-lysine-d-amphetamine administration was only about one-fourth that of the equivalent amount of d-amphetamine with values of 99.5 and 420.2, respectively. $T_{max}$ of d-amphetamine concentration was delayed substantially for L-lysine-d-amphetamine (30 minutes) as compared to $T_{max}$ of d-amphetamine sulfate (5 minutes), reflecting the gradual hydrolysis of L-lysine-d-amphetamine. In conclusion, the bioavailability of d-amphetamine by the intravenous route is substantially decreased and delayed when given as L-lysine-d-amphetamine. Moreover, bioavailability is less than that obtained by oral administration of the equivalent dose of L-lysine-d-amphetamine.

Summary of LC/MS/MS Bioavailability Data in Rats

The following tables summarize the bioavailability data collected in the experiments discussed in examples 13–15. Tables 15–17 summarize the pharmacokinetic parameters of d-amphetamine following oral, intransal, or bolus intravenous administration of d-amphetamine or L-lysine-d-amphetamine.

TABLE 15

Pharmacokinetic Parameters of d-amphetamine Following Oral Administration of L-lysine-d-amphetamine or d-amphetamine at Escalating Doses.

| Route | Drug | Dose (mg/kg) | Cmax (ng/mL) | Tmax (h) | AUC(0–8) (ng · mL/h) | AUC(inf) (ng · mL/h) | F (%) | AUC/Dose (ng · h · kg/mL/mg) | Cmax/Dose ng · kg/mL/mg |
|---|---|---|---|---|---|---|---|---|---|
| Oral | L-lysine-d-amphetamine | 1.5 | 59.6 | 3 | 308 | 331 | 61 | 220.7 | 39.7 |

TABLE 15-continued

Pharmacokinetic Parameters of d-amphetamine Following Oral Administration of L-lysine-d-amphetamine or d-amphetamine at Escalating Doses.

| Route | Drug | Dose (mg/kg) | Cmax (ng/mL) | Tmax (h) | AUC(0–8) (ng · mL/h) | AUC(inf) (ng · mL/h) | F (%) | AUC/Dose (ng · h · kg/mL/mg) | Cmax/Dose ng · kg/mL/mg |
|---|---|---|---|---|---|---|---|---|---|
| Oral | d-amphetamine | 1.5 | 142.2 | 0.5 | 446 | 461 | 84 | 307.3 | 94.8 |
| Oral | L-lysine-d-amphetamine | 3 | 126.9 | 1.5 | 721 | 784 | 72 | 261.3 | 42.3 |
| Oral | d-amphetamine | 3 | 217.2 | 1.5 | 885 | 921 | 84 | 307.0 | 72.4 |
| Oral | L-lysine-d-amphetamine | 6 | 310.8 | 3 | 1,680 | 1,797 | 82 | 299.5 | 51.8 |
| Oral | d-amphetamine | 6 | 815.3 | 0.25 | 1,319 | 1,362 | 62 | 227.0 | 135.9 |
| Oral | L-lysine-d-amphetamine | 12 | 412.6 | 5 | 2,426 | 2,701 | 62 | 225.1 | 34.4 |
| Oral | d-amphetamine | 12 | 1,533.1 | 0.25 | 4,252 | 4,428 | 101 | 369.0 | 127.8 |
| Oral | L-lysine-d-amphetamine | 60 | 2,164.3 | 5 | 9995.1 | 11,478 | 52 | 191.3 | 36.1 |
| Oral | d-amphetamine | 60 | 13,735 | 1 | 32,323 | 48,707 | 223 | 811.8 | 228.9 |

TABLE 16

Pharmacokinetic Parameters of d-amphetamine Following Bolus Intravenous Administration of L-lysine-d-amphetamine.

| Route | Drug | Dose (mg/kg) | Cmax (ng/mL) | Tmax (h) | AUC(0–24) (ng · mL/h) | AUC(inf) (ng · mL/h) |
|---|---|---|---|---|---|---|
| IV | L-lysine-d-amphetamine | 1.5 | 99.5 | 0.5 | 237.8 | 237.9 |
| IV | d-amphetamine | 1.5 | 420.2 | 0.083 | 546.7 | 546.9 |

TABLE 17

Pharmacokinetic Parameters of d-amphetamine Following Intranasal Administration of L-lysine-d-amphetamine.

| Route | Drug | Dose (mg/kg) | Cmax (ng/mL) | Tmax (h) | AUC(0–1) (ng · mL/h) | AUC(inf) (ng · mL/h) |
|---|---|---|---|---|---|---|
| IN | L-lysine-d-amphetamine | 10.16 | 78.6 | 1 | 56 | 91 |
| IN | d-amphetamine | 4.12 | 1962.9 | 0.083 | 1032 | 7291 |

Example 16.

Table 18–20 summarize the pharmacokinetic parameters of L-lysine-d-amphetamine following oral, bolus intravenous, or intranasal administration of L-lysine-d-amphetamine.

TABLE 18

Pharmacokinetic Parameters of L-lysine-d-amphetamine Following Oral Administration of L-lysine-d-amphetamine at Escalating Doses.

| Dose | Drug | Dose (mg/kg) | Cmax (ng/ml) | Tmax (ng/ml) | AUC(0–8) (ng · ml/h) | AUC(inf) (ng · ml/h) | F (%) |
|---|---|---|---|---|---|---|---|
| Oral | L-lysine-d-amphetamine | 1.5 | 36.5 | 0.25 | 59.4 | 60 | 2.6 |
| Oral | L-lysine-d-amphetamine | 3 | 135.4 | 1.5 | 329.7 | 332.1 | 7.2 |
| Oral | L-lysine-d-amphetamine | 6 | 676.8 | 0.25 | 1156.8 | 1170.8 | 12.8 |
| Oral | L-lysine-d-amphetamine | 12 | 855.9 | 1 | 4238.6 | 4510.4 | 24.6 |

TABLE 18-continued

Pharmacokinetic Parameters of L-lysine-d-amphetamine Following Oral Administration of L-lysine-d-amphetamine at Escalating Doses.

| Dose | Drug | Dose (mg/kg) | Cmax (ng/ml) | Tmax (ng/ml) | AUC(0–8) (ng · ml/h) | AUC(inf) (ng · ml/h) | F (%) |
|---|---|---|---|---|---|---|---|
| Oral | L-lysine-d-amphetamine | 60 | 1870.3 | 3 | 8234.3 | 8499.9 | 9.3 |

TABLE 19

Pharmacokinetic Parameters of L-lysine-d-amphetamine Following Bolus Intravenous Administration of L-lysine-d-amphetamine.

| Route | Drug | Dose (mg/kg) | Cmax (ng/mL) | Tmax (h) | AUC(0–24) (ng · mL/h) | AUC(inf) (ng · mL/h) |
|---|---|---|---|---|---|---|
| IV | L-lysine-d-amphetamine | 1.5 | 4513.1 | 0.083 | 2,282 | 2,293 |

TABLE 20

Pharmacokinetic Parameters of L-lysine-d-amphetamine Following Intranasal Administration of L-lysine-d-amphetamine.

| Route | Drug | Dose (mg/kg) | Cmax (ng/mL) | Tmax (h) | AUC(0–1) (ng · mL/h) | AUC(inf) (ng · mL/h) |
|---|---|---|---|---|---|---|
| IN | L-lysine-d-amphetamine | 3 | 3345.1 | 0.25 | 2,580 | 9,139 |

Example 17.

Tables 21 and 22 summarize the percent bioavailability of d-amphetamine following, oral, intranasal, or intravenous administration of L-lysine-d-amphetamine as compared to d-amphetamine sulfate.

TABLE 21

Percent Bioavailability ($AUC_{inf}$) of d-amphetamine Following Administration of L-lysine-d-amphetamine by Various Routes as Compared to Bioavailability Following Administration of d-amphetamine Sulfate.

| Dose (mg/kg) d-amphetamine base | 1.5 | 3 | 6 | 12 | 60 |
|---|---|---|---|---|---|
| HED | 19.9 | 39.9 | 79.7 | 159.4 | 797.2 |
| Oral | 72 | 85 | 132 | 61 | 24 |
| IV | 43 | NA | NA | NA | NA |
| IN | NA | 1 | NA | NA | NA |

TABLE 22

Percent Bioavailability ($C_{max}$) of d-amphetamine Following Administration of L-lysine-d-amphetamine by Various Routes as Compared to Bioavailability Following Administration of d-amphetamine Sulfate.

| Dose (mg/kg) d-amphetamine base | 1.5 | 3 | 6 | 12 | 60 |
|---|---|---|---|---|---|
| HED | 19.9 | 39.9 | 79.7 | 159.4 | 797.2 |
| Oral | 42 | 58 | 38 | 27 | 16 |
| IV | 24 | NA | NA | NA | NA |
| IN | NA | 4 | NA | NA | NA |

Example 18.

Tables 23 and 28 summarize the time-course concentrations of d-amphetamine and L-lysine-d-amphetamine following, oral, intranasal, or intravenous administration of either d-amphetamine or L-lysine-d-amphetamine.

TABLE 23

Time-course Concentrations of d-amphetamine Following Bolus Intravenous Administration of L-lysine-d-amphetamine or d-amphetamine Sulfate at Doses Containing 1.5 mg/kg d-amphetamine Base.

| | Concentration (ng/ml) | |
|---|---|---|
| Time (hours) | L-lysine-d-amphetamine | d-amphetamine sulfate |
| 0 | 0 | 0 |
| 0.083 | 52.8 | 420.2 |
| 0.5 | 99.5 | 249.5 |
| 1.5 | 47.1 | 97.9 |
| 3 | 21.0 | 38.3 |
| 5 | 9.0 | 13.2 |
| 8 | 3.7 | 4.3 |
| 24 | 0.1 | 0.2 |

TABLE 24

Time-course Concentrations of L-lysine-d-amphetamine Following Bolus Intravenous Administration of L-lysine-d-amphetamine at a Dose Containing 1.5 mg/kg d-amphetamine Base.

| Time (hours) | Concentration (ng/ml) L-lysine-d-amphetamine |
|---|---|
| 0 | 0 |
| 0.083 | 4513.1 |
| 0.5 | 1038.7 |
| 1.5 | 131.4 |
| 3 | 19.3 |
| 5 | 17.9 |
| 8 | 8.7 |
| 24 | 11.5 |

TABLE 25

Time-course Concentrations of d-amphetamine Following Oral Administration of L-lysine-d-amphetamine at Various Doses (mg/kg d-amphetamine base).

| Time (hours) | Concentration (ng/ml) | | | | |
|---|---|---|---|---|---|
| | 1.5 mg/kg | 3 mg/kg | 6 mg/kg | 12 mg/kg | 60 mg/kg |
| 0 | 0 | 0 | 0 | 0 | 0 |
| 0.25 | 20.5 | 25.3 | 96 | 54.3 | 90.9 |
| 0.5 | 34 | 40.9 | 140.2 | 96 | 175.1 |
| 1 | 46.7 | 95.1 | 225.9 | 233.3 | 418.8 |
| 1.5 | 40.7 | 126.9 | 268.4 | 266 | 440.7 |
| 3 | 59.6 | 105 | 310.8 | 356.8 | 1145.5 |
| 5 | 38.6 | 107.6 | 219.5 | 412.6 | 2164.3 |
| 8 | 17.1 | 48 | 86 | 225.1 | 1227.5 |

TABLE 26

Time-course Concentrations of d-amphetamine Following Oral Administration of d-amphetamine Sulfate at Various Doses (mg/kg d-amphetamine Base).

| Time (hours) | Concentration (ng/ml) | | | | |
|---|---|---|---|---|---|
| | 1.5 mg/kg | 3 mg/kg | 6 mg/kg | 12 mg/kg | 60 mg/kg |
| 0 | 0 | 0 | 0 | 0 | 0 |
| 0.25 | 107.1 | 152.6 | 815.3 | 1533.1 | 6243.6 |
| 0.5 | 142.2 | 198.4 | 462.7 | 1216 | 7931.6 |
| 1 | 105.7 | 191.3 | 301.3 | 828.8 | 13735.2 |
| 1.5 | 129.5 | 217.2 | 314 | 904.8 | 11514.9 |
| 3 | 52.6 | 135.3 | 134.6 | 519.9 | NA |
| 5 | 29.5 | 73.5 | 77.4 | 404.3 | NA |
| 8 | 11.5 | 25.7 | 31.8 | 115.4 | NA |

TABLE 27

Time-course Concentrations of d-amphetamine Following Intranasal Administration of L-lysine-d-amphetamine or d-amphetamine Sulfate at Doses Containing 3 mg/kg d-amphetamine Base.

| Time (hours) | Concentration (ng/ml) | |
|---|---|---|
| | L-lysine-d-amphetamine | d-amphetamine sulfate |
| 0 | 0 | 0 |
| 0.083 | 31.2 | 1962.9 |
| 0.25 | 45.3 | 1497.3 |
| 0.5 | 61.3 | 996.2 |
| 1 | 78.6 | 404.6 |
| AUC | 56 | 1032.3 |

TABLE 28

Time-course Concentrations of L-lysine-d-amphetamine Following Intranasal Administration of L-lysine-d-amphetamine at a Dose Containing 3 mg/kg d-amphetamine Base.

| Time (h) | Conc. (ng/ml) L-lysine-d-amphetamine |
|---|---|
| 0 | 0 |
| 0.083 | 3345.1 |
| 0.25 | 3369.7 |
| 0.5 | 2985.8 |
| 1 | 1359.3 |

Example 19

LC/MS/MS Analysis of Bioavailability in Dogs

Example Experimental Design:

This was a non-randomized, two-treatment crossover study. All animals were maintained on their normal diet and were fasted overnight prior to each dose administration. L-lysine-d-amphetamine dose was based on the body weight measured on the morning of each dosing day. The actual dose delivered was based on syringe weight before and after dosing. Serial blood samples were obtained from each animal by direct venipuncture of a jugular vein using vacutainer tubes containing sodium heparin as the anticoagulant. Derived plasma samples were stored frozen until shipment to the Quest Pharmaceutical Services, Inc. (Newark, Del.). Pharmacokinetic analysis of the plasma assay results was conducted by Calvert. Animals were treated as follows:

| # of Dog/Sex | Route of Administration | Treatment | Dose Conc. (mg/mL) | Dose Vol. (mL/kg) | Dose Level (mg/kg) |
|---|---|---|---|---|---|
| 3 M | PO | 1 | 0.2 | 10 | 2 |
| 3 M | IV | 2 | 1 | 2 | 2 |

The mg units in the dose concentration and dose level refer to the free base form of test article.

Administration of the Test Article:

Oral: The test article was administered to each animal via a single oral gavage. On Day 1, animals received the oral dose by gavage using an esophageal tube attached to a syringe. Dosing tubes were flushed with approximately 20 mL tap water to ensure the required dosing solution was delivered.

Intravenous: On Day 8, animals received L-lysine-d-amphetamine as a single 30-minute intravenous infusion into a cephalic vein.

Sample Collection:

Dosing Formulations: Post-dosing, remaining dosing formulation was saved and stored frozen.

Blood: Serial blood samples (2 mL) were collected using venipuncture tubes containing sodium heparin. Blood samples were taken at 0, 0.25, 0.5, 1, 2, 4, 8, 12, 24, 48, and 72 hours post-oral dosing. Blood samples were collected at 0, 0.167, 0.33, 0.49 (prior to stop of infusion), 0.583, 0.667, 0.75, 1, 2, 3, 4, 8, 12, and 23 hours post-intravenous infusion start. Collected blood samples were chilled immediately.

Plasma: Plasma samples were obtained by centrifugation of blood samples. Duplicate plasma samples (about 0.2 mL each) were transferred into prelabeled plastic vials and stored frozen at approximately −70° C.

Sample Assay:

Plasma samples were analyzed for L-lysine-d-amphetamine and d-amphetamine using a validated LC-MS/MS method with an LLOQ of 1 ng/mL for both analytes.

Microsoft Excel (Version 6, Microsoft Corp., Redmond, Wash.) was used for calculation of mean plasma concentration and graphing of the plasma concentration-time data. Pharmacokinetic analysis (non-compartmental) was performed using the WinNonlin® software program (Version 4.1, Pharsight, Inc. Mountain View, Calif.). The maximum concentration, $C_{max}$, and the time to $C_{max}$, $T_{max}$, were observed values. The area under the plasma concentration-time curve (AUC) was determined using linear-log trapezoidal rules. The apparent terminal rate constant (λz) was derived using linear least-squares regression with visual inspection of the data to determine the appropriate number of points (minimum of 3 data points) for calculating λz. The AUC(0-inf) was calculated as the sum of AUC(0-t) and Cpred/λz, where Cpred was the predicted concentration at the time of the last quantifiable concentration. The plasma clearance (CL/F) was determined as the ratio of Dose/AUC (0-inf). The mean residence time (MRT) was calculated as the ratio of AUMC(0-inf)/AUC (0-inf), where AUMC(0-inf) was the area under the first moment curve from the time zero to infinity. The volume of distribution at steady state ($V_{ss}$) was estimated as CL*MRT. Half-life was calculated as ln2/λz. The oral bioavailability (F) was calculated as the ratio of AUC(0-inf) following oral dosing to AUC(0-inf) following intravenous dosing. Descriptive statistics (mean and standard deviation) of the pharmacokinetic parameters were calculated using Microsoft Excel.

Figure 27:
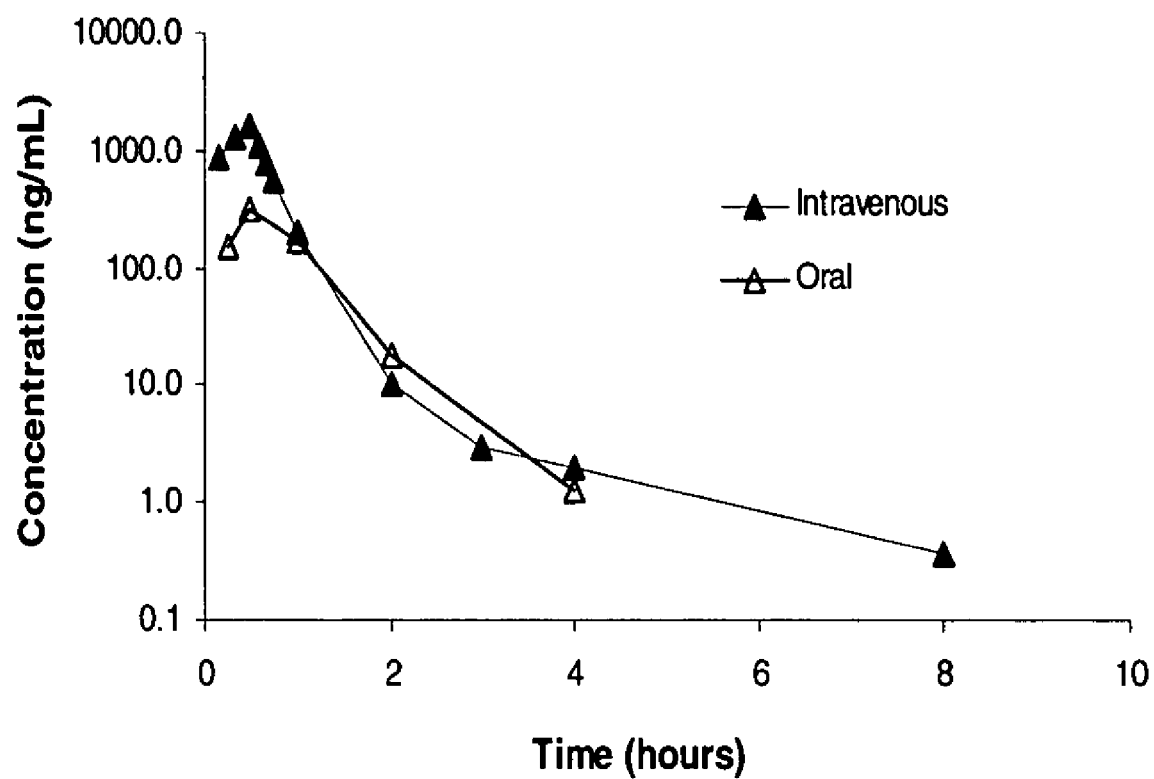
FIG. 27. Mean plasma concentration time profile of L-lysine-d-amphetamine following 30-min intravenous infusion (2 mg/kg) or oral administration of L-lysine-d-amphetamine (2 mg/kg) in conscious male beagle dogs (n=3).

The objectives of this study were to characterize the pharmacokinetics of L-lysine-d-amphetamine and d-amphetamine following administration of L-lysine-d-amphetamine in male beagle dogs. As shown in FIG. 27, in a cross-over design, L-lysine-d-amphetamine was administered to 3 male beagle dogs orally (2 mg/kg) and intravenously (2 mg/kg, 30-minute infusion). Blood samples were collected up to 24 and 72 hours after the intravenous and oral doses, respectively. Plasma samples were analyzed using a LC/MS/MS assay which provided an LLOQ of 1 ng/mL for both analytes.

Figure 28:
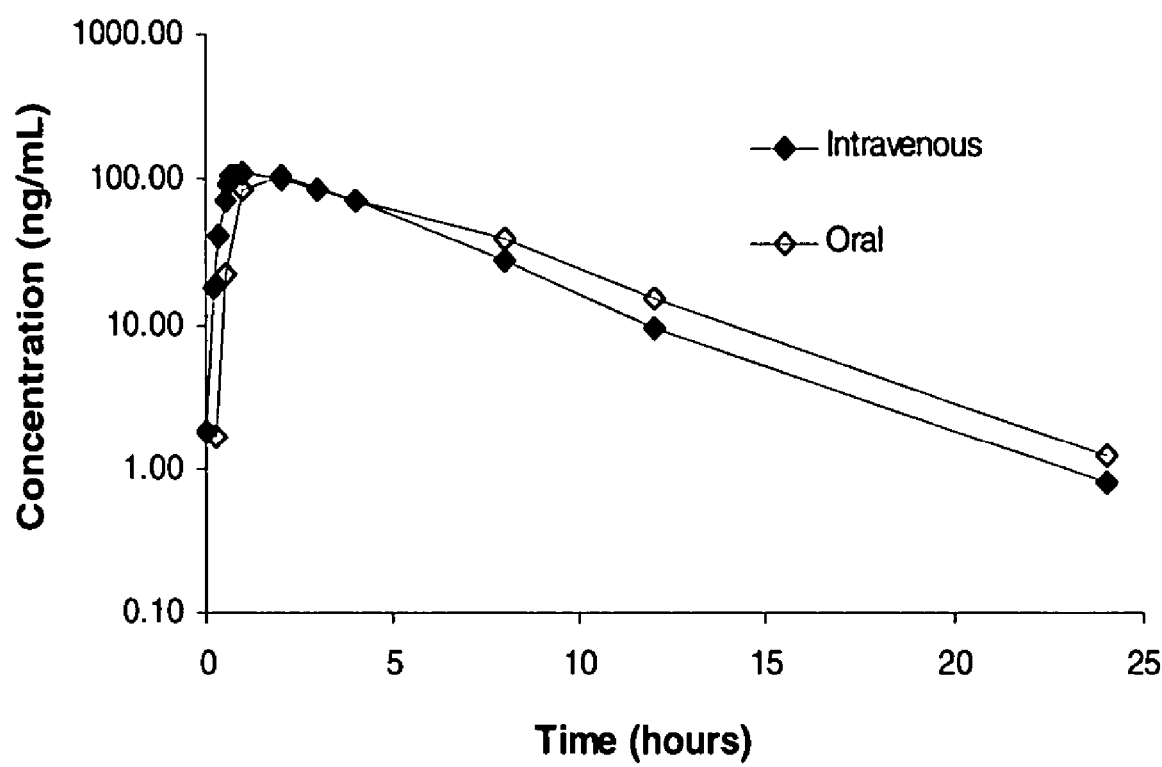
FIG. 28. Plasma concentration time profile of d-amphetamine following 30-min intravenous infusion or oral administration of L-lysine-d-amphetamine (2 mg/kg) in conscious male beagle dogs (n=3).
Figure 29A:
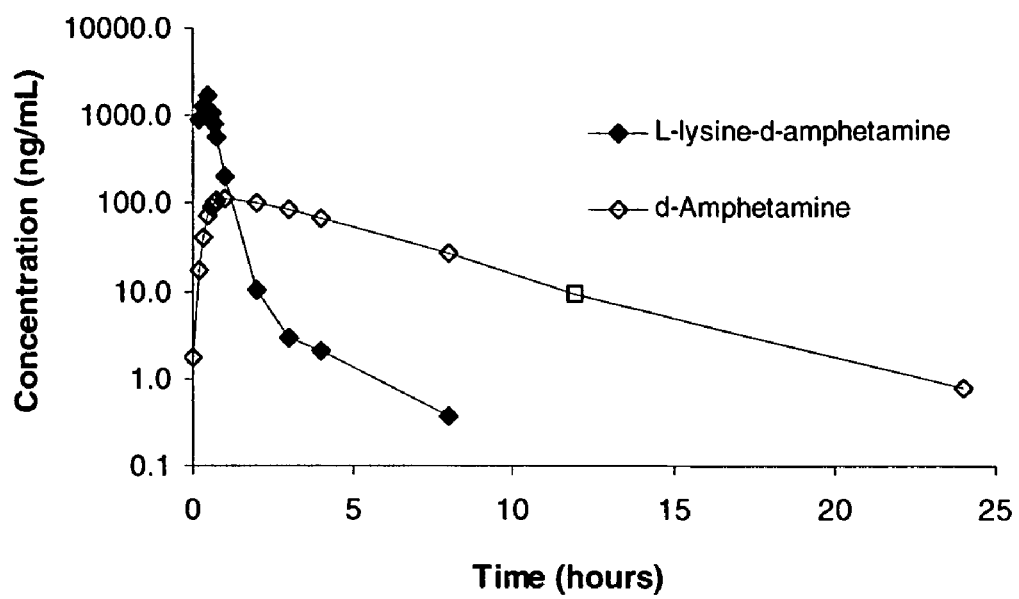
FIGS. 29A–B. Mean plasma concentration time profile of L-lysine-d-amphetamine and d-amphetamine levels in ng/ml (FIG. 29A), and in uM (FIG. 29B), following 30-min intravenous infusion (2 mg/kg) in conscious male beagle dogs (n=3).
Figure 29B:
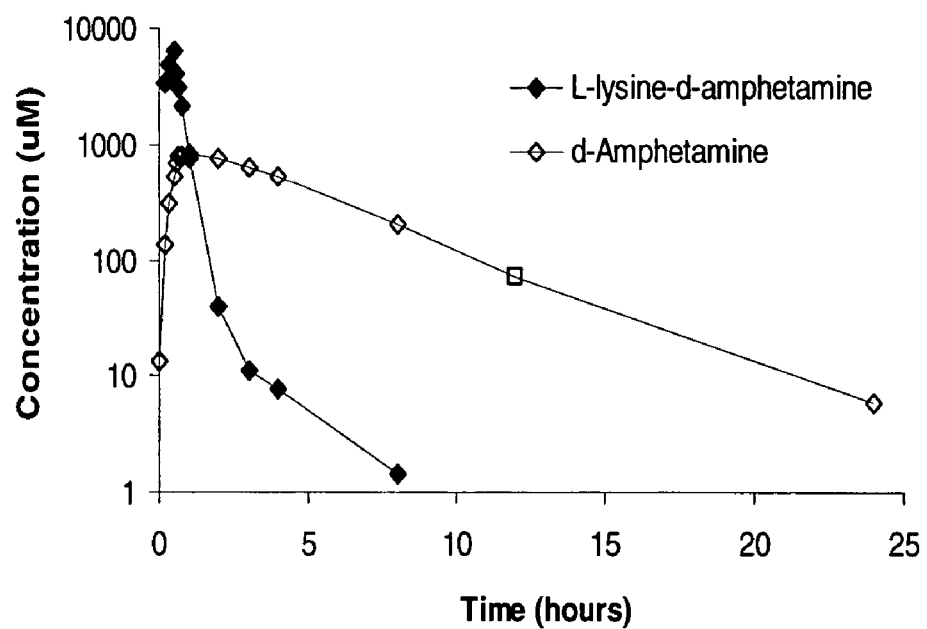
Figure 30A:
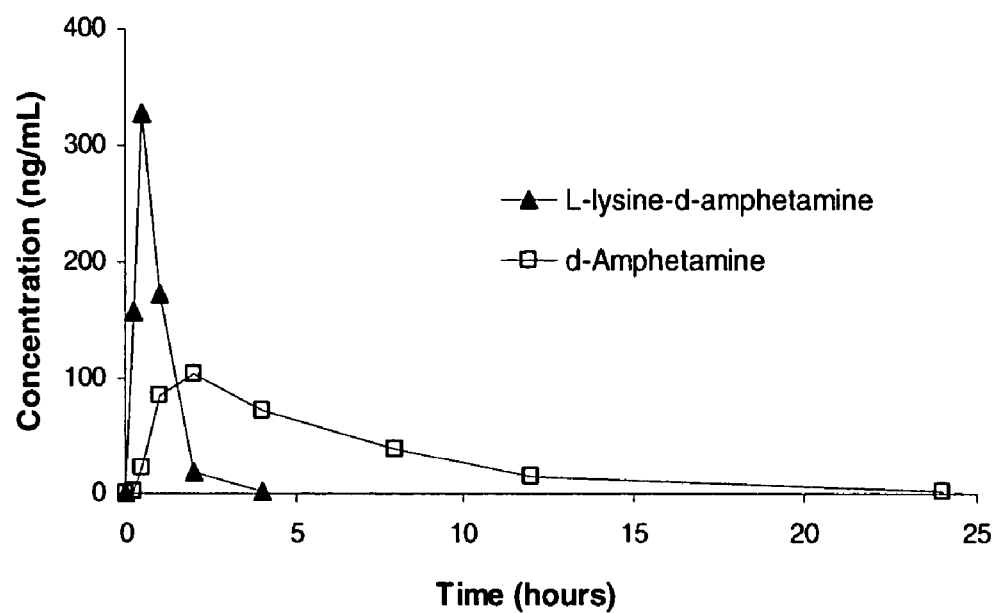
FIGS. 30A–B. Mean plasma concentration time profile of L-lysine-d-amphetamine and d-amphetamine levels in ng/ml (FIG. 30A), and in nM (FIG. 30B), following oral administration of L-lysine-d-amphetamine (2 mg/kg) in conscious male beagle dogs (n=3).
Figure 30B:
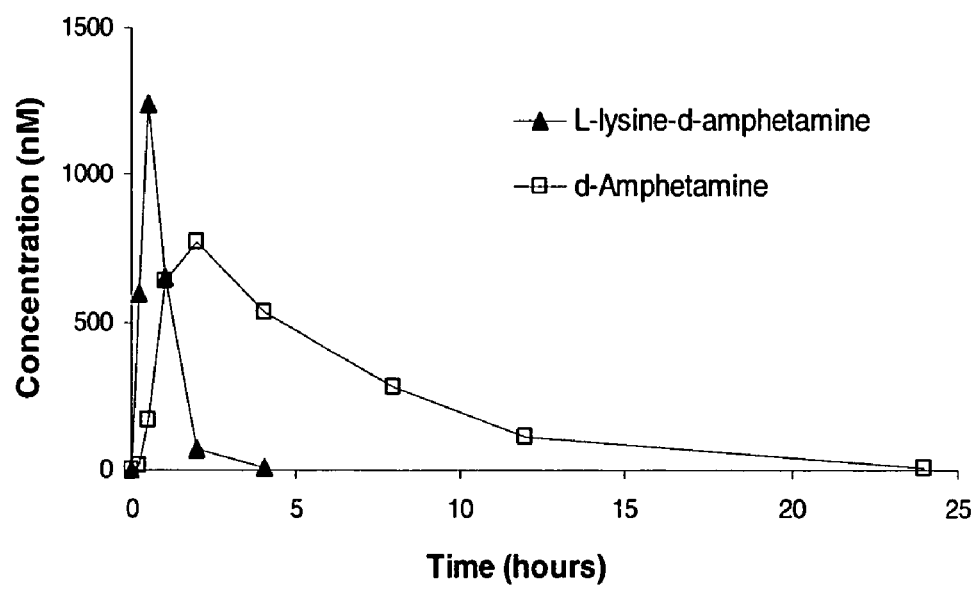
Figure 31A:
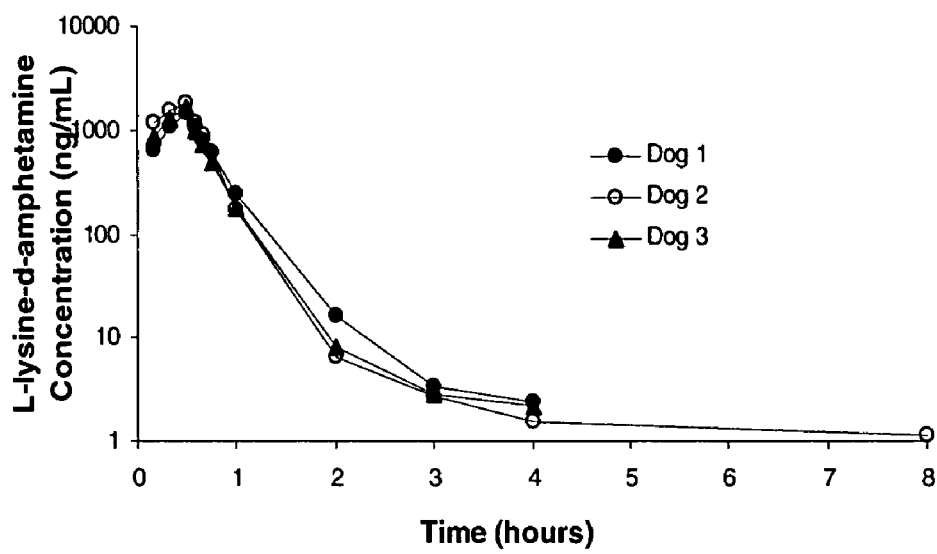
FIGS. 31A–B. Individual plasma concentration time profile of L-lysine-d-amphetamine following intravenous administration (FIG. 31A) or oral administration (FIG. 31B) of L-lysine-d-amphetamine in conscious male beagle dogs. The oral formulation used comprises solution and 0.2 mg/mL in water.
Figure 31B:
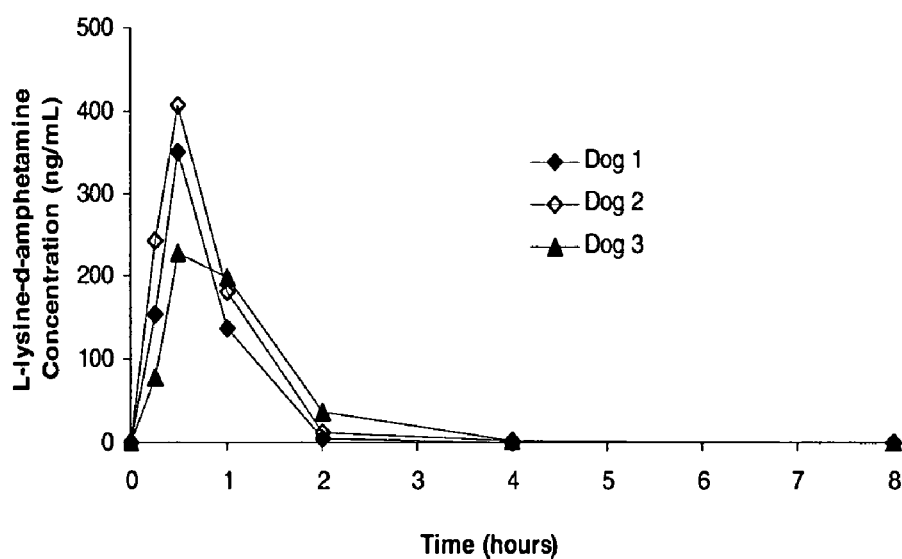
Figure 32A:
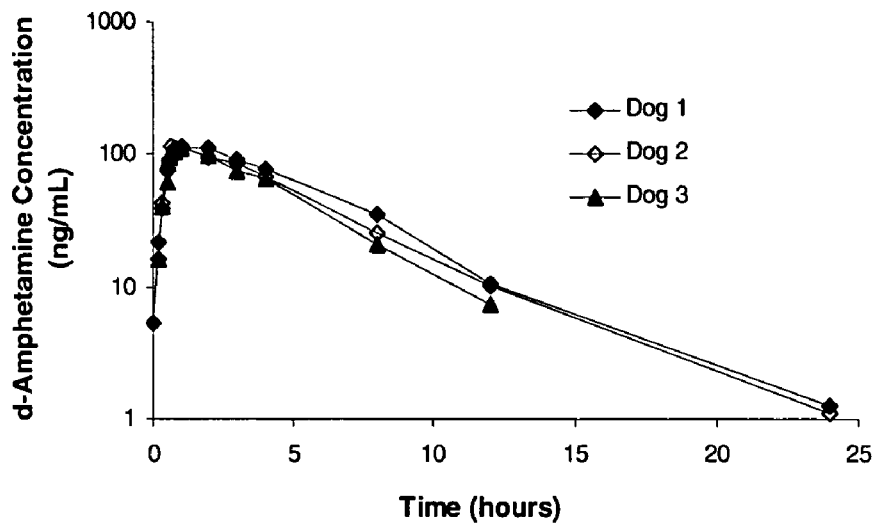
FIGS. 32A–B. Individual plasma concentration time profile of d-amphetamine following intravenous administration (FIG. 32A) or oral administration (FIG. 32B) of L-lysine-d-amphetamine in conscious male beagle dogs.
Figure 32B:
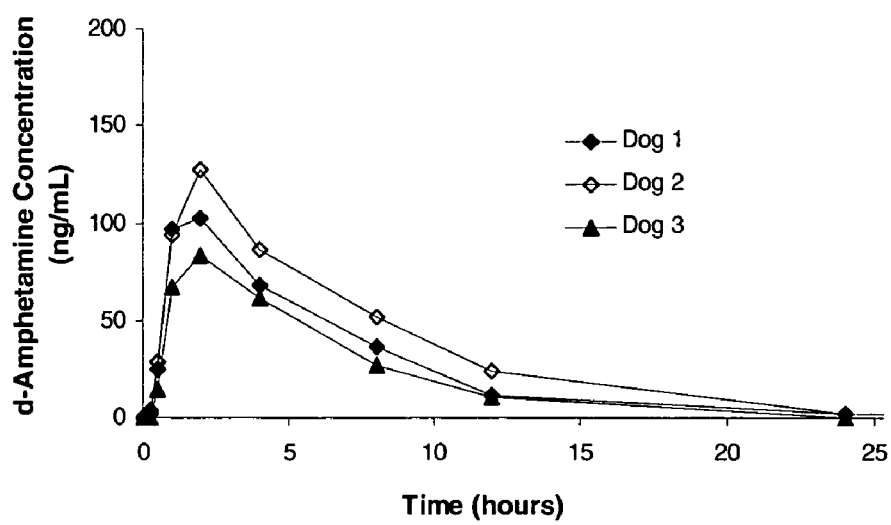
Figure 33:
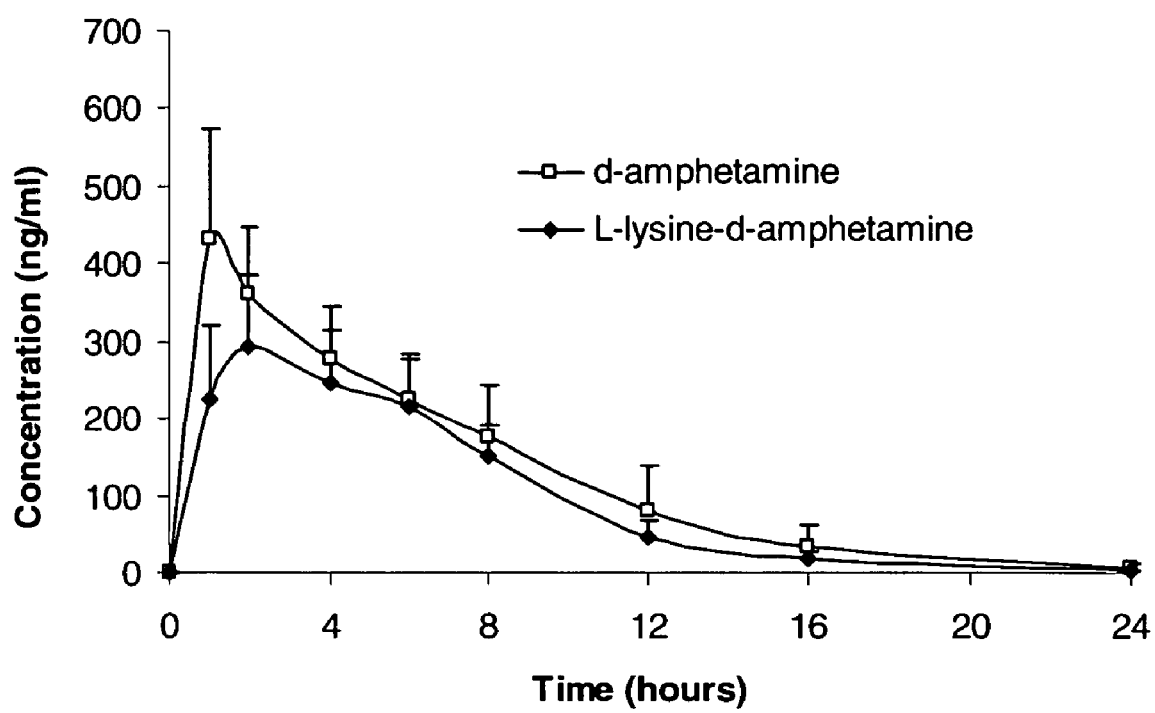
FIG. 33. Plasma concentrations of d-amphetamine following oral administration of L-lysine-d-amphetamine or d-amphetamine sulfate (1.8 mg/kg d-amphetamine base) to male dogs.
Figure 34:
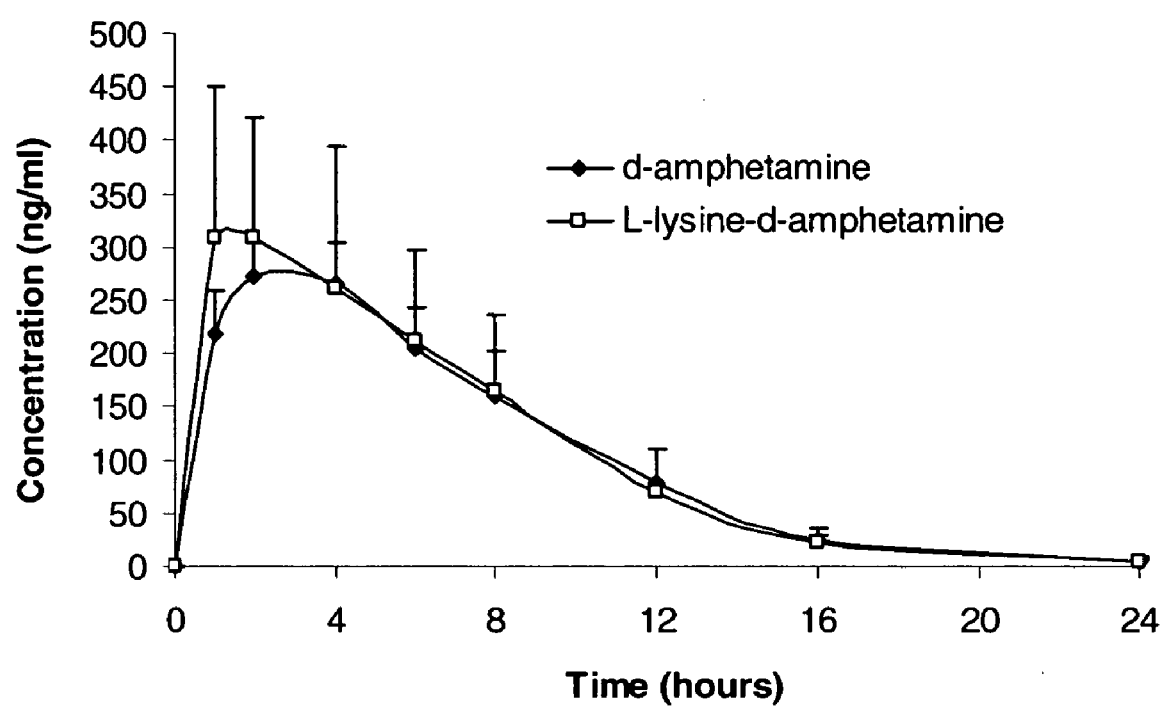
FIG. 34. Plasma concentrations of d-amphetamine following oral administration of L-lysine-d-amphetamine or d-amphetamine sulfate (1.8 mg/kg d-amphetamine base) to female dogs.
Figure 35:
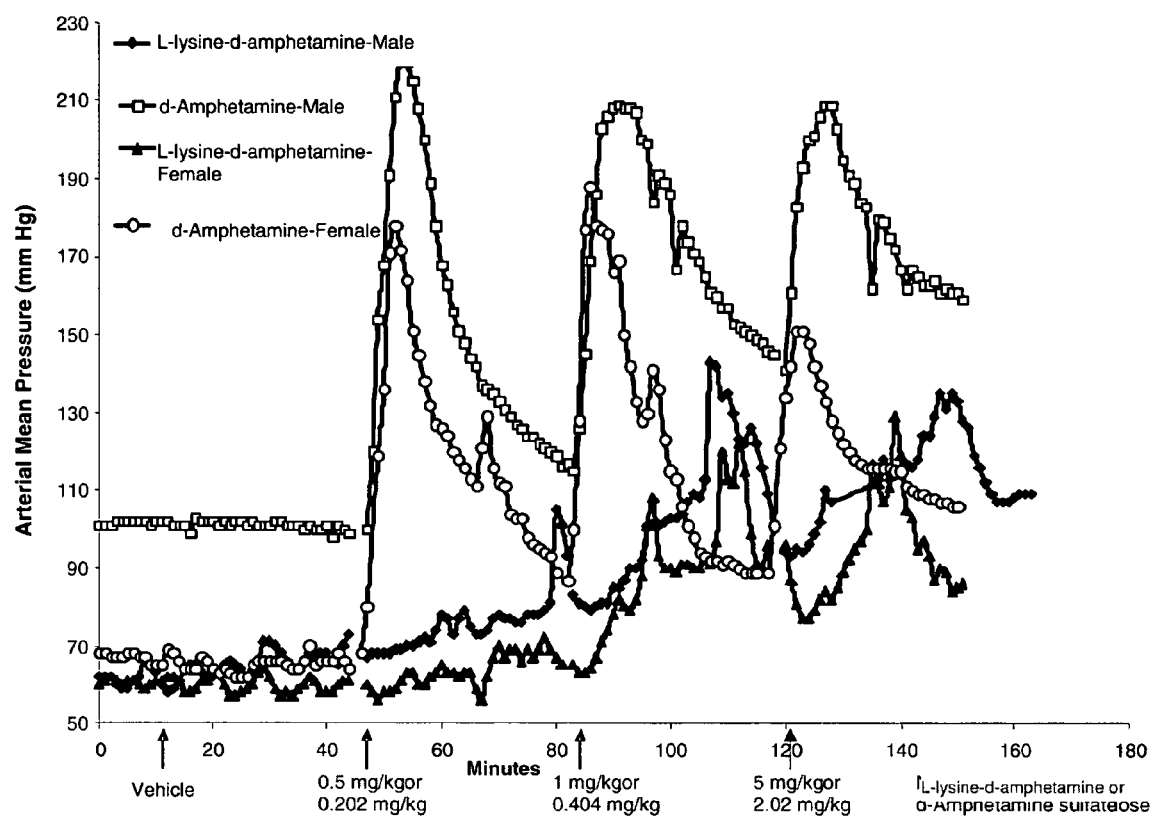
FIG. 35. Mean blood pressure following intravenous bolus injection of increasing amounts of L-lysine-d-amphetamine or d-amphetamine in male and female dogs.

The mean L-lysine-d-amphetamine and d-amphetamine plasma concentration-time profiles following an intravenous or oral dose of L-lysine-d-amphetamine are presented in FIGS. 29 and 30, respectively. Comparative profiles of L-lysine-d-amphetamine to d-amphetamine following both routes are depicted in FIGS. 27–28. Individual plots are depicted in FIGS. 31–32. The pharmacokinetic parameters are summarized in Tables 29–37.

Following a 30-minute intravenous infusion of L-lysine-d-amphetamine, the plasma concentration reached a peak at the end of the infusion. Post-infusion L-lysine-d-amphetamine concentration declined very rapidly in a biexponential manner, and fell below the quantifiable limit (1 ng/mL) by approximately 8 hours post-dose. Results of non-compartmental pharmacokinetic analysis indicate that L-lysine-d-amphetamine is a high clearance compound with a moderate volume of distribution (Vss) approximating total body water (0.7 L/kg). The mean clearance value was 2087 mL/h●kg (34.8 mL/min●kg) and was similar to the hepatic blood flow in the dog (40 mL/min●kg). Consequently, L-lysine-d-amphetamine is a moderate to high hepatic extraction compound with significant first pass effects (including the conversion to d-amphetamine) following oral administration.

L-lysine-d-amphetamine was rapidly absorbed after oral administration with $T_{max}$ at 0.5 hours in all three dogs. Mean absolute oral bioavailability was 33%. Since significant first pass effects are expected for L-lysine-d-amphetamine, a 33% bioavailability suggests that L-lysine-d-amphetamine is very well absorbed in the dog. The apparent terminal half-life was 0.39 hours, indicating rapid elimination, as observed following intravenous administration.

Plasma concentration-time profiles of d-amphetamine following intravenous or oral administration of L-lysine-d-amphetamine were very similar, With $C_{max}$, $T_{max}$ and AUC values for both routes essentially the same. At a 2 mg/kg oral dose of L-lysine-d-amphetamine, the mean $C_{max}$ of d-amphetamine was 104.3 ng/mL. The half-life of d-amphetamine was 3.1 to 3.5 hours, much longer when compared to L-lysine-d-amphetamine.

In this study, L-lysine-d-amphetamine was infused over a 30 minute time period. Due to rapid clearance of L-lysine-d-amphetamine it is likely that bioavailability of d-amphetamine from L-lysine-d-amphetamine would decrease if a similar dose were given by intravenous bolus injection. Even when given as an infusion the bioavailability of d-amphetamine from L-lysine-d-amphetamine did not exceed that of a similar dose given orally and the time to peak concentration was substantially delayed. This data further supports that L-lysine-d-amphetamine affords a decrease in the abuse liability of d-amphetamine by intravenous injection.

TABLE 29

Pharmacokinetic Parameters of L-lysine-d-amphetamine in Male Beagle Dogs Following Oral or Intravenous Administration of L-lysine-d-amphetamine (1 mg/kg d-amphetamine base).

| Route | Dose (mg/kg) | $C_{max}$ (ng/mL) | $T_{max}$[a] (h) | AUC(inf) (ng · h/mL) | $t_{1/2}$ (h) | MRT (h) | CL/F (mL/h · kg) | $V_{ss}$ (mL/kg) | F (%) |
|---|---|---|---|---|---|---|---|---|---|
| IV | 1 | 1650 | 0.49 | 964 | 0.88 | 0.33 | 2087 | 689 | NA |
|  | (0.00) | (178) | (0.49–0.49) | (97.1) | (0.2) | (0.03) | (199) | (105.9) |  |

TABLE 29-continued

Pharmacokinetic Parameters of L-lysine-d-amphetamine in Male Beagle Dogs Following Oral or Intravenous Administration of L-lysine-d-amphetamine (1 mg/kg d-amphetamine base).

| Route | Dose (mg/kg) | $C_{max}$ (ng/mL) | $T_{max}{}^a$ (h) | AUC(inf) (ng · h/mL) | $t_{1/2}$ (h) | MRT (h) | CL/F (mL/h · kg) | $V_{ss}$ (mL/kg) | F (%) |
|---|---|---|---|---|---|---|---|---|---|
| Oral | 1 (0.00) | 328.2 (91.9) | 0.5 (0.5–0.5) | 319 (46.3) | 0.39 (0.1) | 0.81 (0.19) | 6351 (898.3) | NA | 33 (1.9) |

[a]median (range)

TABLE 30

Pharmacokinetic Parameters of d-amphetamine in Male Beagle Dogs Following Oral or Intravenous Administration of L-lysine-d-amphetamine (1 mg/kg d-amphetamine base).

| Route | Dose(mg/kg) | $C_{max}$ (ng/mL) | $T_{max}{}^a$ (h) | AUC(inf) (ng · h/mL) | $t_{1/2}$ (h) |
|---|---|---|---|---|---|
| IV | 2 (0.00) | 113.2 (3.2) | 1.0 (0.67–2.0) | 672.5 (85.7) | 3.14 (0.4) |
| Oral | 2 (0.00) | 104.3 (21.8) | 2.0 (2–2) | 728.0 (204.9) | 3.48 (0.4) |

[a]median (range)

TABLE 31

Pharmacokinetics of L-lysine-d-amphetamine in Male Beagle Dogs Following Intravenous Administration of L-lysine-d-amphetamine (1 mg/kg d-amphetamine base).
Dose Route: 30-min iv Infusion
Dose: 2 mg/kg/h (free form)

| Dog ID | $C_{max}$ (ng/mL) | $T_{max}{}^a$ (h) | AUC(0–t) (ng · h/mL) | AUC(inf) (ng · h/mL) | $t_{1/2}$ (h) | CL (mL/h/kg) | Vss (mL/kg) | MRT (h) |
|---|---|---|---|---|---|---|---|---|
| 1 | 1470.3 | 0.49 | 898.2 | 900.2 | 0.72 | 2222 | 807.4 | 0.36 |
| 2 | 1826.4 | 0.49 | 1072.3 | 1076.1 | ND[b] | 1859 | 603.4 | 0.32 |
| 3 | 1654.2 | 0.49 | 914.1 | 916.9 | 1.05 | 2181 | 656.0 | 0.30 |
| Mean | 1650 | 0.49 | 961.5 | 964.4 | 0.88 | 2087 | 689.0 | 0.33 |
| SD | 178 | 0.49–0.49 | 96.0 | 97.1 | 0.2 | 199 | 105.9 | 0.03 |

[a]median (range);
[b]not determined

Abbreviations of pharmacokinetic parameters are as follows:

$C_{max}$, maximum observed plasma concentration;

AUC(0–t), total area under the plasma concentration versus time curve from 0 to the last data point;

AUC(0–inf), total area under the plasma concentration versus time curve;

$t_{1/2}$, apparent terminal half-life;

CL, clearance following iv administration;

MRT, mean residence time;

Vss, volume of distribution at steady state.

TABLE 32

Pharmacokinetic Parameters of L-lysine-d-amphetamine in Male Beagle Dogs Following Oral Administration of L-lysine-d-amphetamine (1 mg/kg d-amphetamine base).
Dose Route: Oral
Dose: 2 mg/kg (free form)

| Dog ID | $C_{max}$ (ng/mL) | $T_{max}^a$ (h) | AUC(0–t) (ng · h/mL) | AUC(inf) (ng · h/mL) | $t_{1/2}$ (h) | CL/F (mL/h/kg) | MRT (h) | F (%) |
|---|---|---|---|---|---|---|---|---|
| 1 | 350.2 | 0.5 | 275.3 | 277.1 | 0.24 | 7218 | 0.68 | 30.8 |
| 2 | 407.2 | 0.5 | 367.8 | 368.7 | 0.48 | 5424 | 0.74 | 34.3 |
| 3 | 227.4 | 0.5 | 310.8 | 312.0 | 0.45 | 6410 | 1.03 | 34.0 |
| Mean | 328.2 | 0.5 | 318.0 | 319.3 | 0.39 | 6351 | 0.81 | 33.0 |
| SD | 91.9 | 0.0 | 46.7 | 46.3 | 0.1 | 898.3 | 0.19 | 1.9 |

$^a$median (range)
Abbreviations of pharmacokinetic parameters are as follows:
$C_{max}$, maximum observed plasma concentration;
$T_{max}$, time when $C_{max}$ observed;
AUC(0–t), total area under the plasma concentration versus time curve from 0 to the last data point;
AUC(0–inf), total area under the plasma concentration versus time curve;
$t_{1/2}$, apparent terminal half-life;
CL/F, oral clearance;
MRT, mean residence time;
F, bioavailability.

TABLE 33

Pharmacokinetics of L-lysine-d-amphetamine in Male Beagle Dogs Following Intravenous Administration of L-lysine-d-amphetamine (1 mg/kg d-amphetamine base).
Dose Route: 30-min iv Infusion
Dose: 2 mg/kg of L-lysine-d-amphetamine (free form)

| Dog ID | $C_{max}$ (ng/mL) | $T_{max}^a$ (h) | AUC(0–t) (ng · h/mL) | AUC(inf) (ng · h/mL) | $t_{1/2}$ (h) |
|---|---|---|---|---|---|
| 1 | 111.2 | 2.0 | 751.9 | 757.6 | 3.35 |
| 2 | 116.8 | 0.67 | 668.5 | 673.7 | 3.43 |
| 3 | 111.4 | 1.0 | 557.8 | 586.1 | 2.65 |
| Mean | 113.2 | 1.00 | 659.4 | 672.5 | 3.14 |
| SD | 3.2 | 0.67–2.0 | 97 | 85.7 | 0.4 |

$^a$median (range)
Abbreviations of pharmacokinetic parameters are as follows:
$C_{max}$, maximum observed plasma concentration;
$T_{max}$, time when $C_{max}$ observed;
AUC(0–t), total area under the plasma concentration versus time curve from 0 to the last data point;
AUC(0–inf), total area under the plasma concentration versus time curve;
$t_{1/2}$, apparent terminal half-life;
CL/F, oral clearance;
MRT, mean residence time;
F, bioavailability.

TABLE 34

Pharmacokinetics of L-lysine-d-amphetamine in Male Beagle Dogs Following Oral Administration of L-lysine-d-amphetamine (1 mg/kg d-amphetamine base).
Dose Route: Oral
Dose: 2 mg/kg of L-lysine-d-amphetamine (free form)

| Dog ID | $C_{max}$ (ng/mL) | $T_{max}^a$ (h) | AUC(0–t) (ng · h/mL) | AUC(inf) (ng · h/mL) | $t_{1/2}$ (h) |
|---|---|---|---|---|---|
| 1 | 102.1 | 2.0 | 686.34 | 696.89 | 3.93 |
| 2 | 127.2 | 2.0 | 937.57 | 946.62 | 3.44 |
| 3 | 83.7 | 2.0 | 494.61 | 540.38 | 3.06 |
| Mean | 104.3 | 2.0 | 706.2 | 728.0 | 3.48 |
| SD | 21.8 | 2.0–2.0 | 222.1 | 204.9 | 0.4 |

$^a$median (range)
Abbreviations of pharmacokinetic parameters are as follows:
$C_{max}$, maximum observed plasma concentration;
$T_{max}$, time when $C_{max}$ observed;
AUC(0–t), total area under the plasma concentration versus time curve from 0 to the last data point;
AUC(0–inf), total area under the plasma concentration versus time curve;
$t_{1/2}$, apparent terminal half-life;
CL/F, oral clearance;
MRT, mean residence time;
F, bioavailability.

TABLE 35

Pharmacokinetics of d-amphetamine in Male Beagle Dogs Following Oral Administration of L-lysine-d-amphetamine or d-amphetamine sulfate (1.8 mg/kg d-amphetamine base).

| | Mean Plasma Concentration | | Standard Deviation (SD) | | Coefficient of Variation (CV) | |
|---|---|---|---|---|---|---|
| Time (hours) | d-amphetamine | L-lysine-d-amphetamine | d-amphetamine | L-lysine-d-amphetamine | d-amphetamine | L-lysine-d-amphetamine |
| 0 | 0 | 0 | 0 | 0 | 0 | 0 |
| 1 | 431.4 | 223.7 | 140.7 | 95.9 | 32.6 | 42.9 |
| 2 | 360 | 291.8 | 87.6 | 93.6 | 24.3 | 32.1 |
| 4 | 277.7 | 247.5 | 68.1 | 66 | 24.5 | 26.7 |
| 6 | 224.1 | 214.7 | 59.3 | 62.1 | 26.5 | 28.9 |
| 8 | 175.4 | 150 | 66.7 | 40.1 | 38.0 | 26.7 |
| 12 | 81.4 | 47.6 | 58.7 | 19 | 72.1 | 39.9 |
| 16 | 33 | 19.6 | 28.1 | 9 | 85.2 | 45.9 |
| 24 | 7.2 | 4.5 | 4.5 | 1.7 | 62.5 | 37.8 |

TABLE 36

Pharmacokinetics of d-amphetamine in Female Beagle Dogs Following Oral Administration of L-lysine-d-amphetamine or d-amphetamine sulfate (1.8 mg/kg d-amphetamine base).

| | Mean Plasma Concentration | | Standard Deviation (SD) | | Coefficient of Variation (CV) | |
|---|---|---|---|---|---|---|
| Time (hours) | d-amphetamine | L-lysine-d-amphetamine | d-amphetamine | L-lysine-d-amphetamine | d-amphetamine | L-lysine-d-amphetamine |
| 0 | 0 | 0 | 0 | 0 | 0 | 0 |
| 1 | 217.8 | 308.8 | 141.7 | 40.7 | 65.1 | 13.2 |
| 2 | 273.5 | 308 | 113.7 | 29.6 | 41.6 | 9.6 |
| 4 | 266 | 260.9 | 132.7 | 37.3 | 49.9 | 14.3 |
| 6 | 204.7 | 212.1 | 84.5 | 38.7 | 41.3 | 18.2 |
| 8 | 160.1 | 164.3 | 72.7 | 43.5 | 45.4 | 26.5 |
| 12 | 79.4 | 68.7 | 41.3 | 31 | 52.0 | 45.1 |
| 16 | 25.5 | 22.3 | 13.4 | 4.7 | 52.5 | 21.1 |
| 24 | 5.6 | 5.4 | 4.1 | 1.9 | 73.2 | 35.2 |

TABLE 37

Pharmacokinetic Parameters of d-amphetamine in Male and Female Beagle Dogs Following Oral Administration of L-lysine-d-amphetamine or d-amphetamine sulfate (1.8 mg/kg d-amphetamine base).

| | Males Compound | | Females Compound | |
|---|---|---|---|---|
| Parameter | d-amphetamine | L-lysine-d-amphetamine | d-amphetamine | L-lysine-d-amphetamine |
| AUCinf | 3088.9 | 2382.2 | 2664.5 | 2569.9 |
| Percent | 100 | 77 | 100 | 96 |
| Cmax | 431.4 | 291.8 | 308.8 | 273.5 |
| Percent | 100 | 67 | 100 | 89 |
| Tmax(hours) | 1 | 2 | 1 | 2 |
| Percent | 100 | 200 | 100 | 200 |

Example 20

Delayed Cardiovascular Effects of L-lysine-d-amphetamine as Compared to d-amphetamine Following Intravenous Infusion.

Systolic and diastolic blood pressure (BP) are increased by d-amphetamine even at therapeutic doses. Since L-lysine-d-amphetamine is expected to release d-amphetamine (albeit slowly) as a result of systemic metabolism, a preliminary study was done using equimolar doses of d-amphetamine or L-lysine-d-amphetamine to 4 dogs (2 male and 2 female). The results suggest that the amide prodrug is inactive and that slow release of some d-amphetamine, occurs beginning 20 minutes after the first dose. Relative to d-amphetamine, however, the effects are less robust. For example, the mean blood pressure is graphed in FIG. 35. Consistent with previously published data (Kohli and Goldberg, 1982), small doses of d-amphetamine were observed to have rapid effects on blood pressure. The lowest dose (0.202 mg/kg, equimolar to 0.5 mg/kg of L-lysine-d-amphetamine) produced an acute doubling of the mean BP followed by a slow recovery over 30 minutes.

Figure 36:
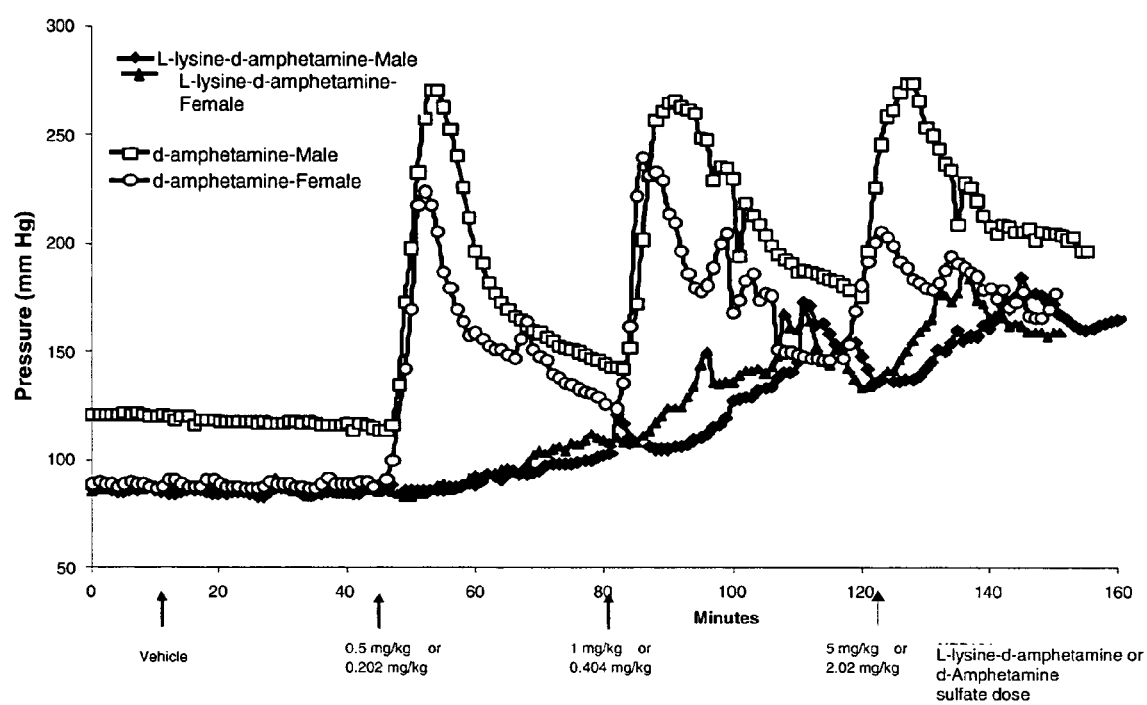
FIG. 36. Left ventricular blood pressure following intravenous bolus injection of increasing amounts of L-lysine-d-amphetamine or d-amphetamine in male and female dogs.

By contrast, L-lysine-d-amphetamine produced very little change in mean BP until approximately 30 minutes after injection. At that time, pressure increased by about 20–50%. Continuous release of d-amphetamine is probably responsible for the slow and steady increase in blood pressure over the remaining course of the experiment. Upon subsequent injections, d-amphetamine is seen to repeat its effect in a non-dose dependent fashion. That is, increasing dose 10-fold from the first injection produced a rise to the same maximum pressure. This may reflect the state of catecholamine levels in nerve terminals upon successive stimulation of d-amphetamine bolus injections. Note that the rise in mean blood pressure seen after successive doses of L-lysine-d-amphetamine (FIG. 35) produces a more gradual and less intense effect. Similar results were observed for left ventricular pressure (FIG. 36). These results further substantiate the significant decrease in d-amphetamine bioavailability by the intravenous route when given as L-lysine-d-amphetamine. As a result the rapid onset of the pharmacological effect of d-amphetamine that is sought by persons injecting the drug is eliminated.

TABLE 38

Effects of L-lysine-d-amphetamine on Cardiovascular Parameters in the Anesthetized Dog - Mean Values (n = 2)

| TREATMENT | TIME | SAP | % Change | DAP | % Change | MAP | % Change | LVP | % Change |
|---|---|---|---|---|---|---|---|---|---|
| 0.9% Saline | 0 | 81 | 0 | 48 | 0 | 61 | 0 | 87 | 0 |
| 1 ml/kg | 30 | 87 | 7 | 54 | 11 | 67 | 10 | 87 | 0 |
| L-lysine-d-amphetamine | 0 | 84 | 0 | 51 | 0 | 64 | 0 | 86 | 0 |
| 0.5 mg/kg | 5 | 87 | 4 | 52 | 3 | 66 | 3 | 87 | 2 |
|  | 15 | 93 | 11 | 51 | 1 | 67 | 5 | 95 | 11 |
|  | 25 | 104 | 25 | 55 | 8 | 73 | 15 | 105 | 22 |
|  | 30 | 107 | 28 | 58 | 14 | 77 | 21 | 108 | 26 |
| L-lysine-d-amphetamine | 0 | 105 | 0 | 55 | 0 | 74 | 0 | 108 | 0 |
| 1.0 mg/kg | 5 | 121 | 15 | 63 | 15 | 85 | 15 | 120 | 11 |
|  | 15 | 142 | 35 | 73 | 33 | 100 | 35 | 140 | 29 |
|  | 25 | 163 | 55 | 97 | 75 | 124 | 68 | 162 | 50 |
|  | 30 | 134 | 28 | 73 | 32 | 98 | 32 | 144 | 33 |
| L-lysine-d-amphetamine | 0 | 132 | 0 | 71 | 0 | 95 | 0 | 144 | 0 |
| 5.0 mg/kg | 5 | 142 | 7 | 71 | 0 | 99 | 4 | 151 | 5 |
|  | 15 | 176 | 33 | 98 | 39 | 130 | 37 | 184 | 28 |
|  | 25 | 126 | −5 | 69 | −3 | 96 | 1 | 160 | 11 |
|  | 30 | 132 | 0 | 70 | −1 | 99 | 4 | 163 | 13 |

SAP—systolic arterial pressure (mmHg)
MAP—mean arterial pressure (mmHg)
DAP—diastolic arterial pressure (mmHg)
LVP—left ventricular pressure (mmHg)
% Change- percent change from respective Time 0.

TABLE 39

Effects of d-Amphetamine on Cardiovascular Parameters in the Anesthetized Dog - Mean Values (n = 2)

| TREATMENT | TIME | SAP | % Change | DAP | % Change | MAP | % Change | LVP | % Change |
|---|---|---|---|---|---|---|---|---|---|
| 0.9% Saline | 0 | 110 | 0 | 67 | 0 | 84 | 0 | 105 | 0 |
| 1 ml/kg | 30 | 108 | −2 | 65 | −3 | 82 | −2 | 101 | −3 |
| d-amphetamine | 0 | 111 | 0 | 67 | 0 | 84 | 0 | 104 | 0 |
| 0.202 mg/kg | 5 | 218 | 97 | 145 | 117 | 176 | 109 | 214 | 107 |
|  | 15 | 168 | 52 | 97 | 45 | 125 | 49 | 157 | 52 |
|  | 25 | 148 | 34 | 87 | 30 | 110 | 31 | 142 | 37 |
|  | 30 | 140 | 26 | 80 | 20 | 103 | 23 | 135 | 30 |
| d-amphetamine | 0 | 139 | 0 | 78 | 0 | 101 | 0 | 133 | 0 |
| 0.404 mg/kg | 5 | 240 | 73 | 147 | 88 | 187 | 85 | 238 | 79 |
|  | 15 | 193 | 39 | 112 | 44 | 145 | 43 | 191 | 43 |
|  | 25 | 166 | 19 | 92 | 17 | 122 | 20 | 168 | 26 |
|  | 30 | 160 | 16 | 87 | 11 | 117 | 16 | 163 | 22 |
| d-amphetamine | 0 | 158 | 0 | 87 | 0 | 115 | 0 | 162 | 0 |
| 2.02 mg/kg | 5 | 228 | 44 | 128 | 48 | 169 | 47 | 227 | 40 |
|  | 15 | 196 | 24 | 107 | 23 | 142 | 23 | 200 | 24 |
|  | 25 | 189 | 20 | 102 | 17 | 135 | 17 | 192 | 19 |
|  | 30 | 183 | 16 | 98 | 13 | 129 | 12 | 187 | 16 |

SAP—systolic arterial pressure (mmHg)
MAP—mean arterial pressure (mmHg)
DAP—diastolic arterial pressure (mmHg)
LVP—left ventricular pressure (mmHg)
% Change- percent change from respective Time 0.

Example 21

Figure 37:
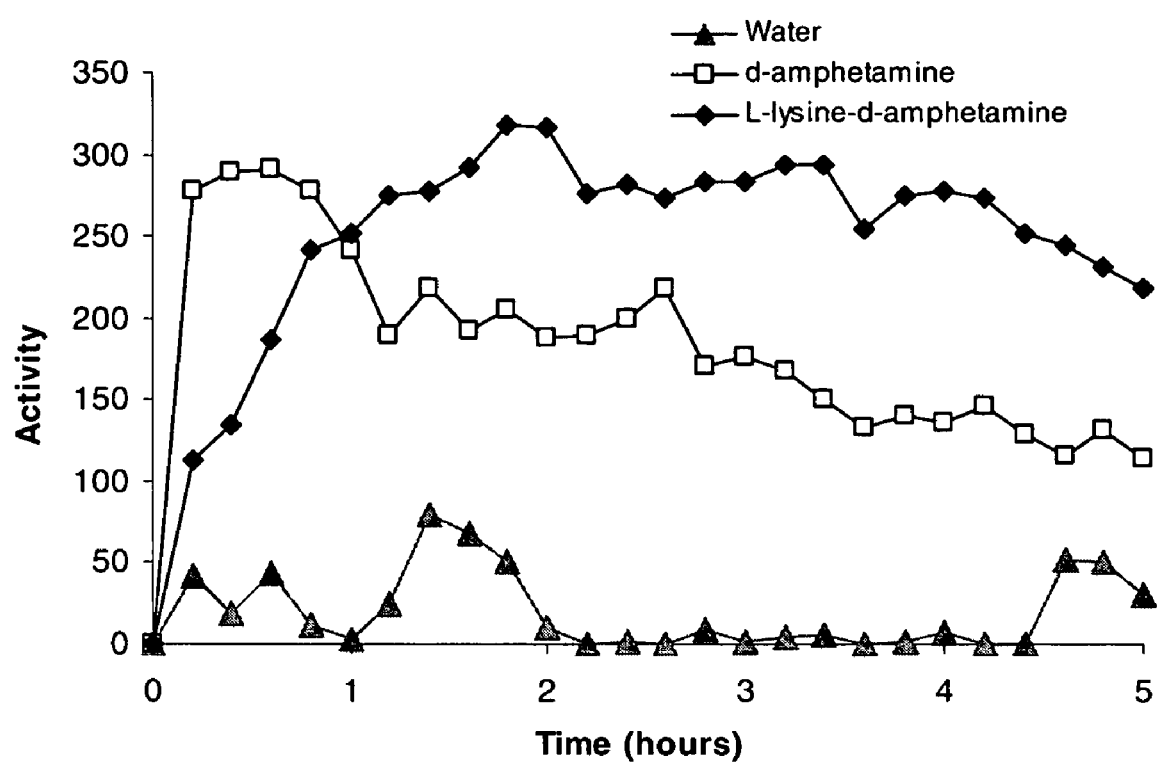
FIG. 37. Locomotor activity of rats following oral administration of L-lysine-d-amphetamine or d-amphetamine (5 hour time-course).
Figure 38:
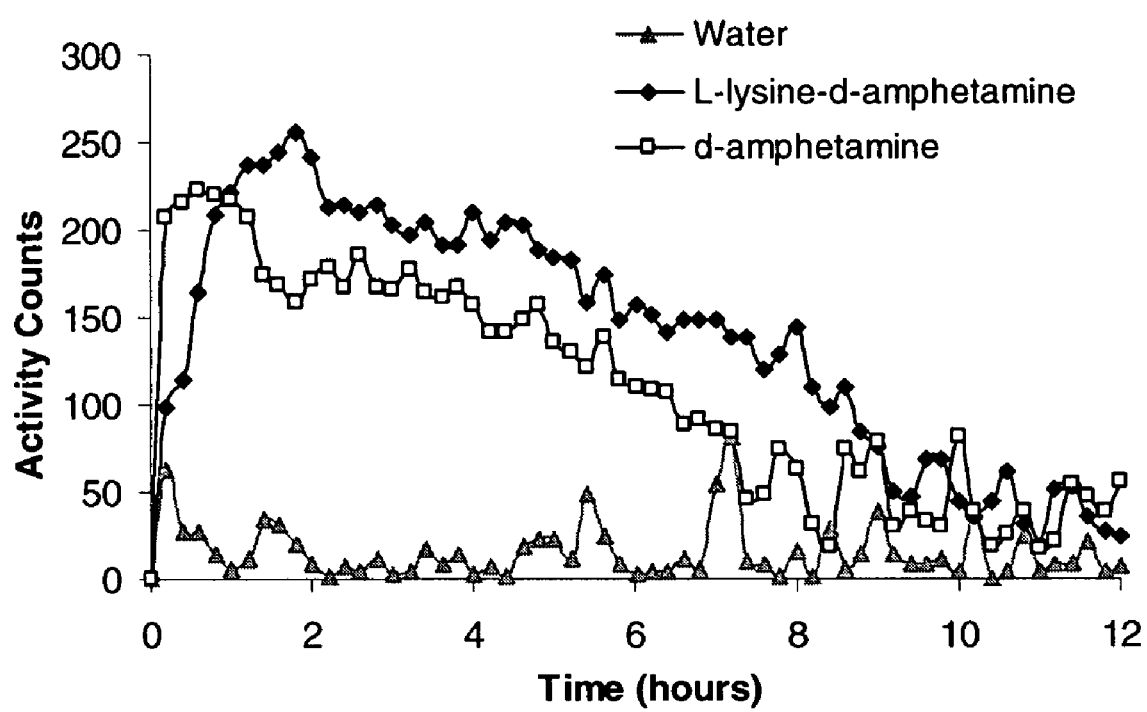
FIG. 38. Locomotor activity of rats following oral administration of L-lysine-d-amphetamine or d-amphetamine (12 hour time-course).

Pharmacodynamic (Locomotor) Response to Amphetamine vs. L-lysine-d-amphetamine by Oral Administration Male Sprague-Dawley rats were provided water ad libitum, fasted overnight and dosed by oral gavage with 6 mg/kg of amphetamine or L-lysine-d-amphetamine containing the equivalent amount of d-amphetamine. Horizontal locomotor activity (HLA) was recorded during the light cycle using photocell activity chambers (San Diego Instruments). Total counts were recorded every 12 minutes for the duration of the test. Rats were monitored in three separate experiments for 5, 8, and 12 hours, respectively. Time vs. HLA counts for d-amphetamine vs. L-lysine-d-amphetamine is shown in FIGS. 37–38. In each experiment the time until peak activity was delayed and the pharmacodynamic effect was evident for an extended period of time for L-lysine-d-amphetamine as compared to d-amphetamine. The total activity counts for HLA of Lys-Amp dosed rats were increased (11–41%) over those induced by d-amphetamine in all three experiments (Tables 40 and 41).

TABLE 40

Locomotor Activity of Rats Orally Administered d-amphetamine vs. L-lysine-d-amphetamine (5 Hours)

| Test Material | Total Activity Counts | Total Activity Counts Above Baseline | Peak of activity (Counts per 0.2 h) | Time of Peak (Counts per 0.2 h) | Time of Last Count Above 200 per 0.2 h |
|---|---|---|---|---|---|
| Vehicle | 4689 | 4174 | 80 | 1.4 | — |
| L-lysine-d-amphetamine | 6417 | 5902 | 318 | 1.8 | 5 h |
| d-amphetamine | 515 | 0 | 291 | 0.6 | 2.6 h |

TABLE 41

Locomotor Activity of Rats Orally Administered Amphetamine vs. L-lysine-d-amphetamine (12 Hours)

| Test Material | Total Activity Counts | Total Activity Counts Above Baseline | Peak of activity (Counts per 0.2 h) | Time of Peak (Counts per 0.2 h) | Time of Last Count Above 100 per 0.2 h |
|---|---|---|---|---|---|
| Vehicle | 936 | 0 | 81 | 7.2 | — |
| L-lysine-d-amphetamine | 8423 | 7487 | 256 | 1.8 | 8.6 h |
| d-amphetamine | 6622 | 5686 | 223 | 0.6 | 6.4 h |

Example 22

Figure 39:
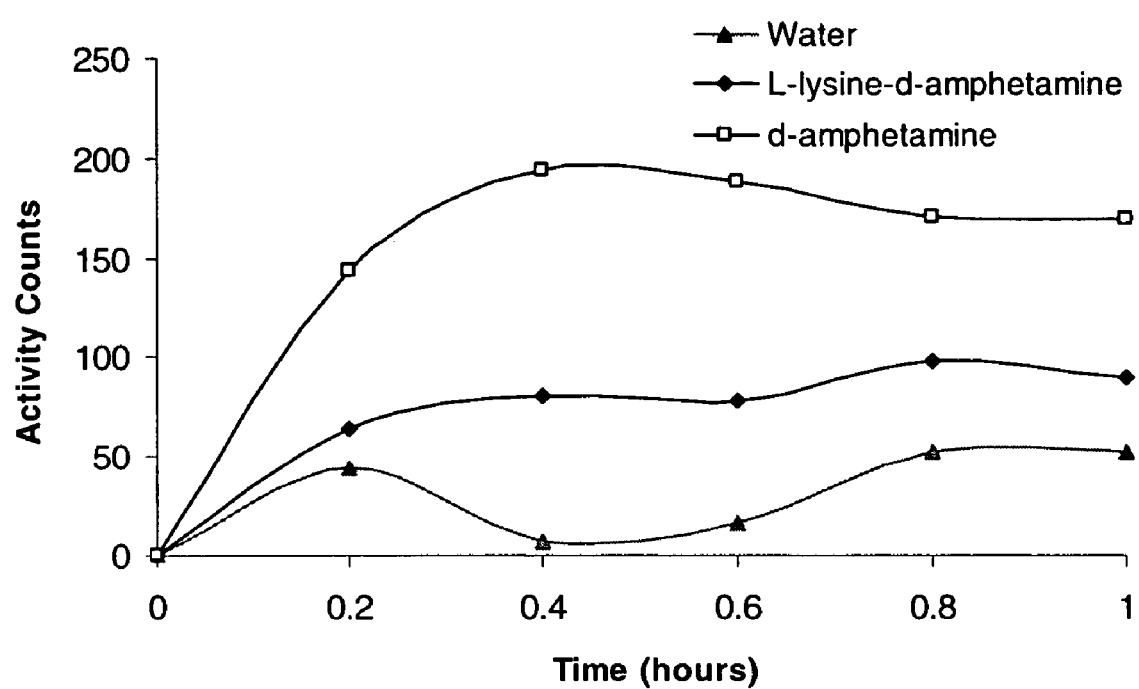
FIG. 39. Locomotor activity of rats following intranasal administration of L-lysine-d-amphetamine or d-amphetamine (1 hour time-course).
Figure 40:
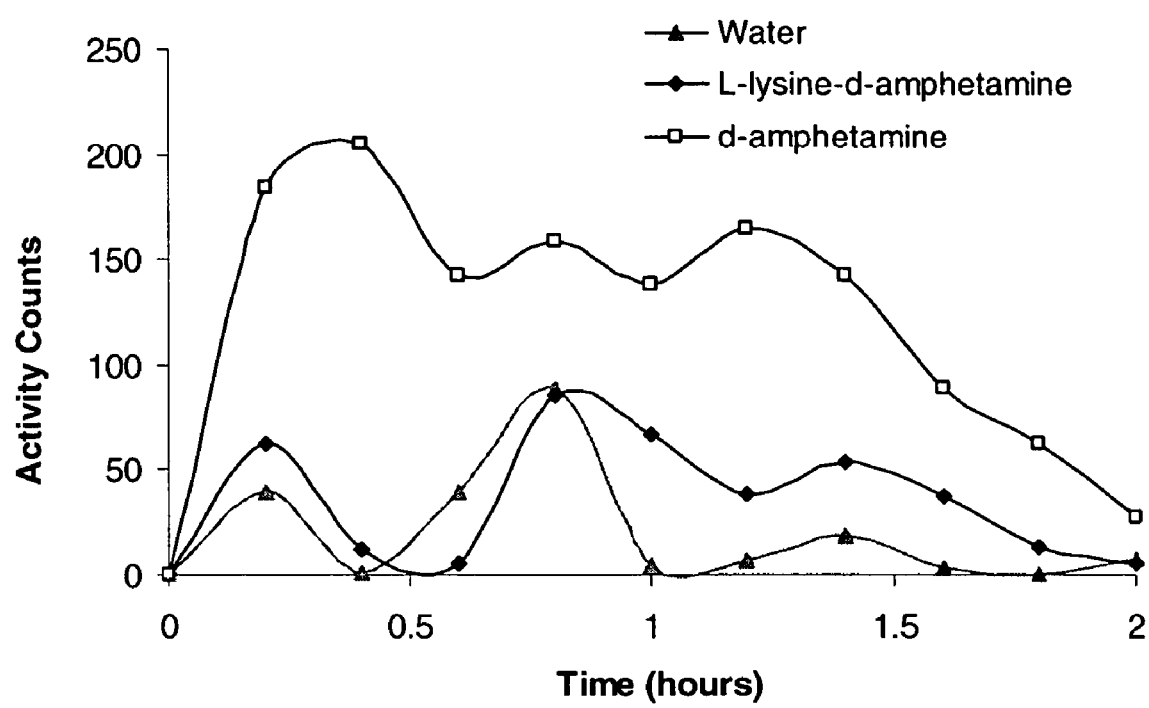
FIG. 40. Locomotor activity of rats following intranasal administration (with carboxymethylcellulose) of L-lysine-d-amphetamine or d-amphetamine (2 hour time-course).

Pharmacodynamic Response to Amphetamine vs. L-lysine-d-amphetamine by Intranasal Administration Male Sprague-Dawley rats were dosed by intranasal administration with 1.0 mg/kg of amphetamine or L-lysine-d-amphetamine containing the equivalent amount of d-amphetamine. In a second set of similarly dosed animals carboxymethyl cellulose (CMC) was added to the drug solutions at a concentration of 62.6 mg/mil (approximately 2-fold higher than the concentration of L-lysine-d-amphetamine and 5-fold higher than the d-amphetamine content). The CMC drug mixtures were suspended thoroughly before each dose was delivered. Locomotor activity was monitored using the procedure described in the section titled example 7. As shown in FIGS. 39–40, the activity vs. time (1 hour or 2 hours) is shown for amphetamine/CMC vs. L-lysine-d-amphetamine and compared to that of amphetamine vs. L-lysine-d-amphetamine CMC. As seen in FIG. 39, addition of CMC to L-lysine-d-amphetamine decreased the activity response of IN dosed rats to levels similar to the water/CMC control, whereas no effect was seen on amphetamine activity by the addition of CMC. The increase in activity over baseline of L-lysine-d-amphetamine with CMC was only 9% compared to 34% for Lys-Amp without CMC when compared to activity observed for d-amphetamine dosed animals (Table 42). CMC had no observable affect on d-amphetamine activity induced by IN administration.

TABLE 42

Locomotor Activity of Intranasal d-amphetamine vs. L-lysine-d-amphetamine with and without CMC

| Drug | n | Total Activity Counts (1 h) | Total Activity Counts Above Baseline | Percent d-amphetamine |
|---|---|---|---|---|
| d-amphetamine | 3 | 858 | 686 | 100 |
| d-amphetamine CMC | 3 | 829 | 657 | 100 |
| L-lysine-d-amphetamine | 4 | 408 | 237 | 35 |

TABLE 42-continued

Locomotor Activity of Intranasal d-amphetamine vs. L-lysine-d-amphetamine with and without CMC

| Drug | n | Total Activity Counts (1 h) | Total Activity Counts Above Baseline | Percent d-amphetamine |
|---|---|---|---|---|
| L-lysine-d-amphetamine CMC | 4 | 232 | 60 | 9 |
| Water | 1 | 172 | 0 | 0 |
| Water CMC | 1 | 172 | 0 | 0 |

Example 23

Figure 41:
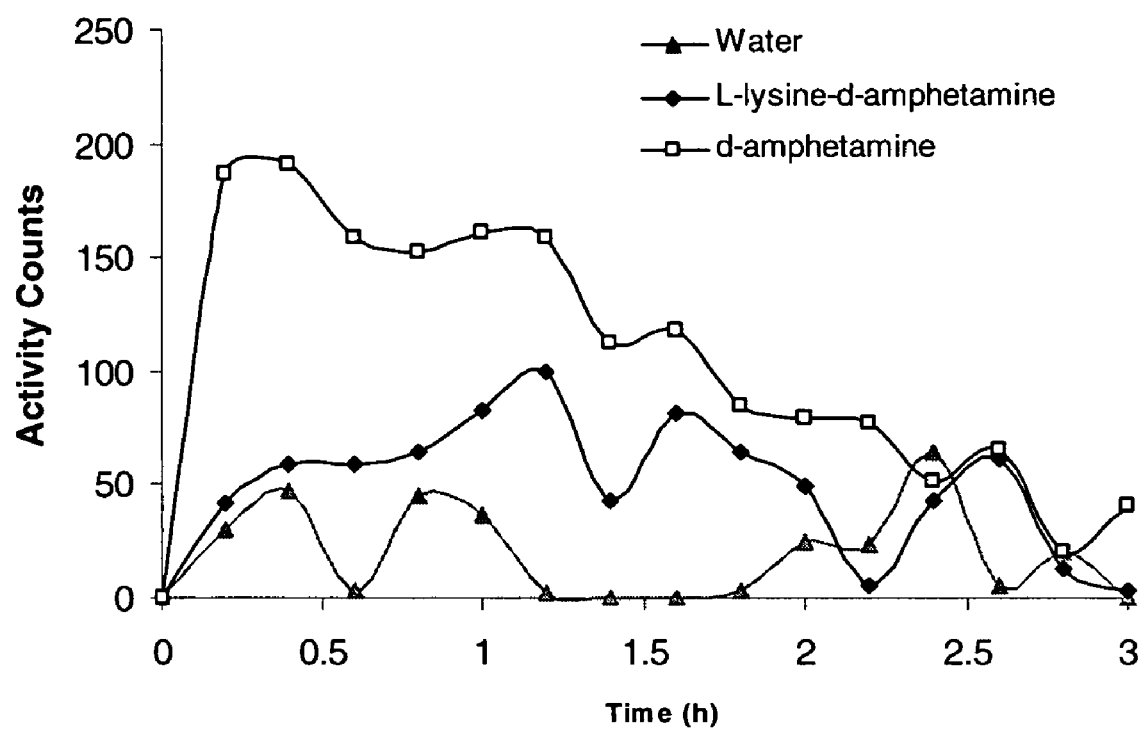
FIG. 41. Locomotor activity of rats following intravenous administration of L-lysine-d-amphetamine or d-amphetamine (3 hour time-course).
Figure 42:
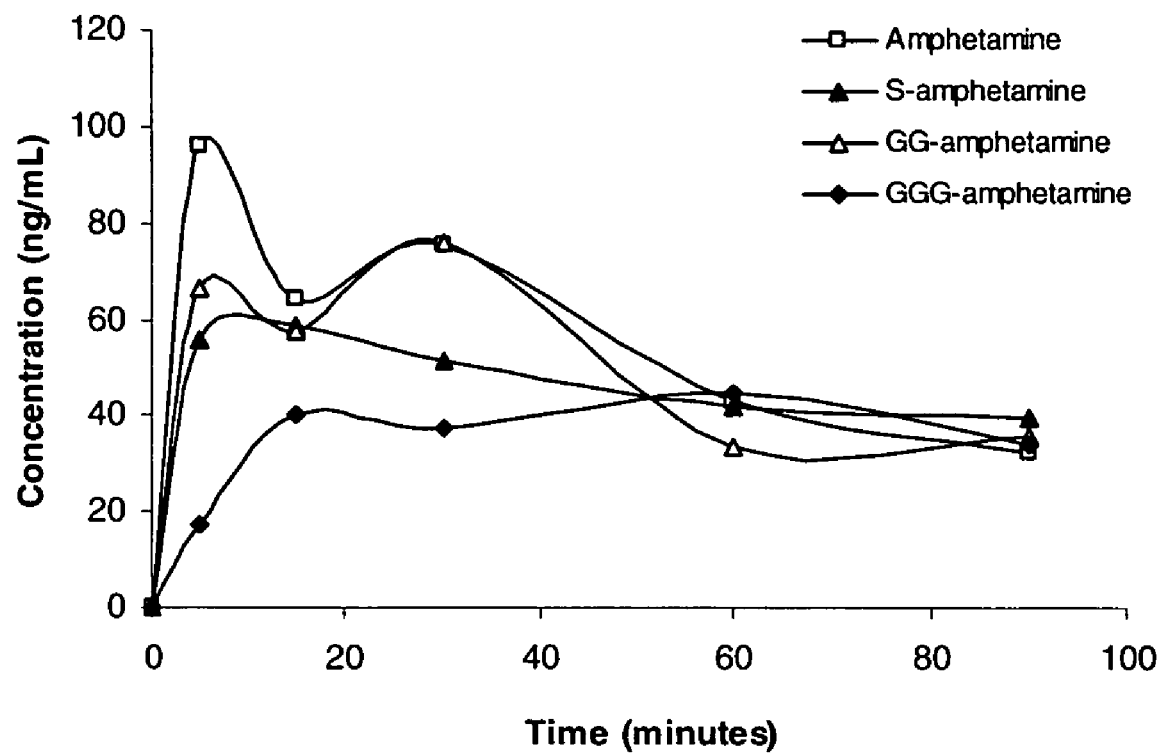
FIG. 42. Intranasal bioavailability of abuse-resistant amphetamine amino acid-, di-, and tri-peptide conjugates (ELISA analysis).
Figure 43:
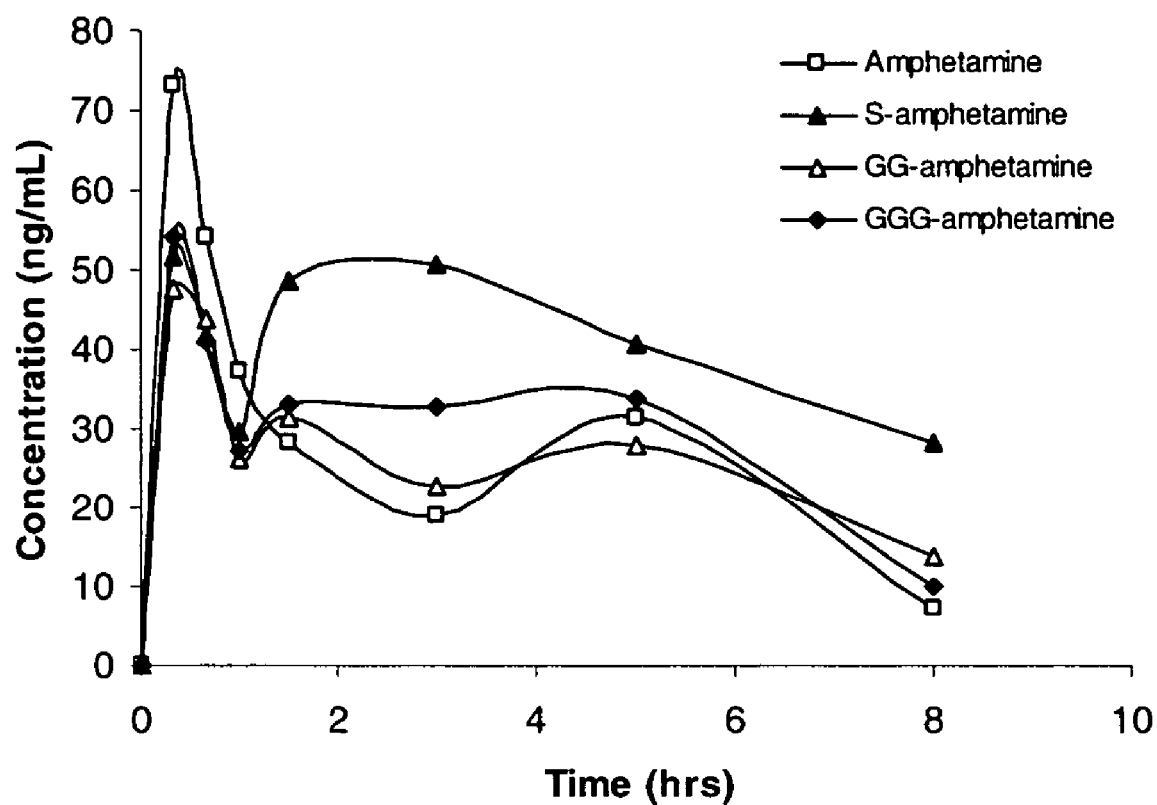
FIG. 43. Oral bioavailability of abuse-resistant amphetamine amino acid-, di-, and tri-peptide conjugates (ELISA analysis).
Figure 44:
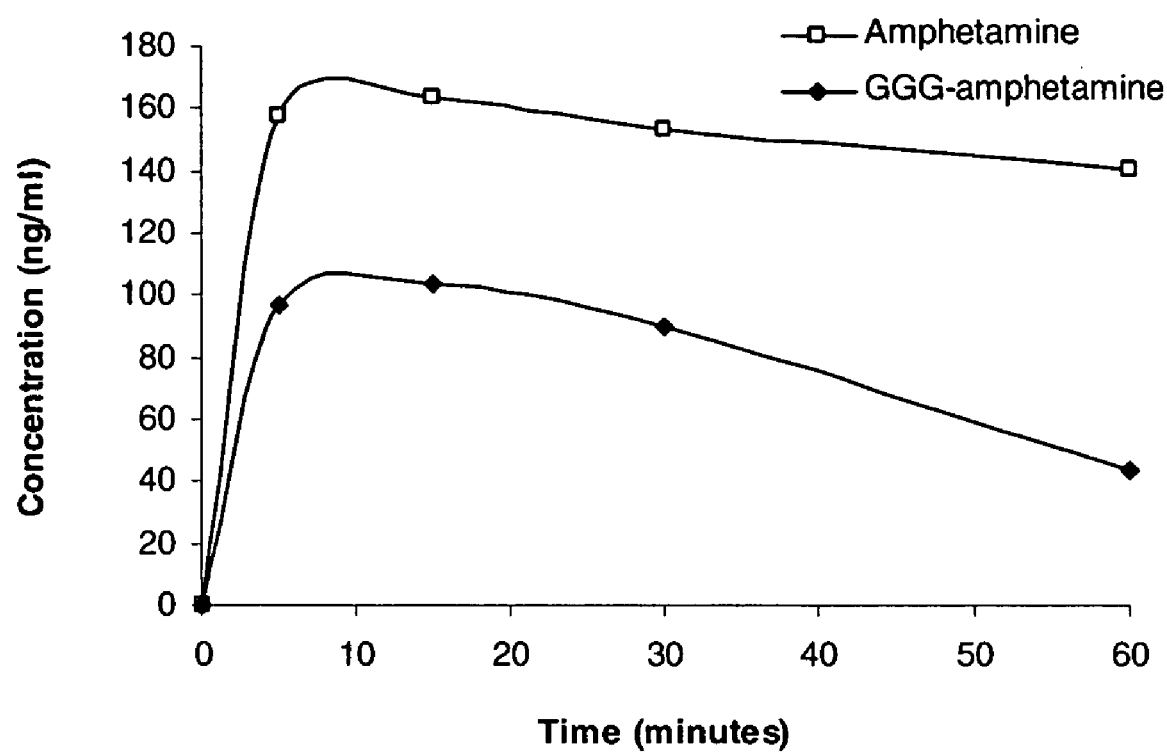
FIG. 44. Intravenous bioavailability of an abuse-resistant amphetamine tri-peptide conjugate (ELISA analysis).
Figure 45:
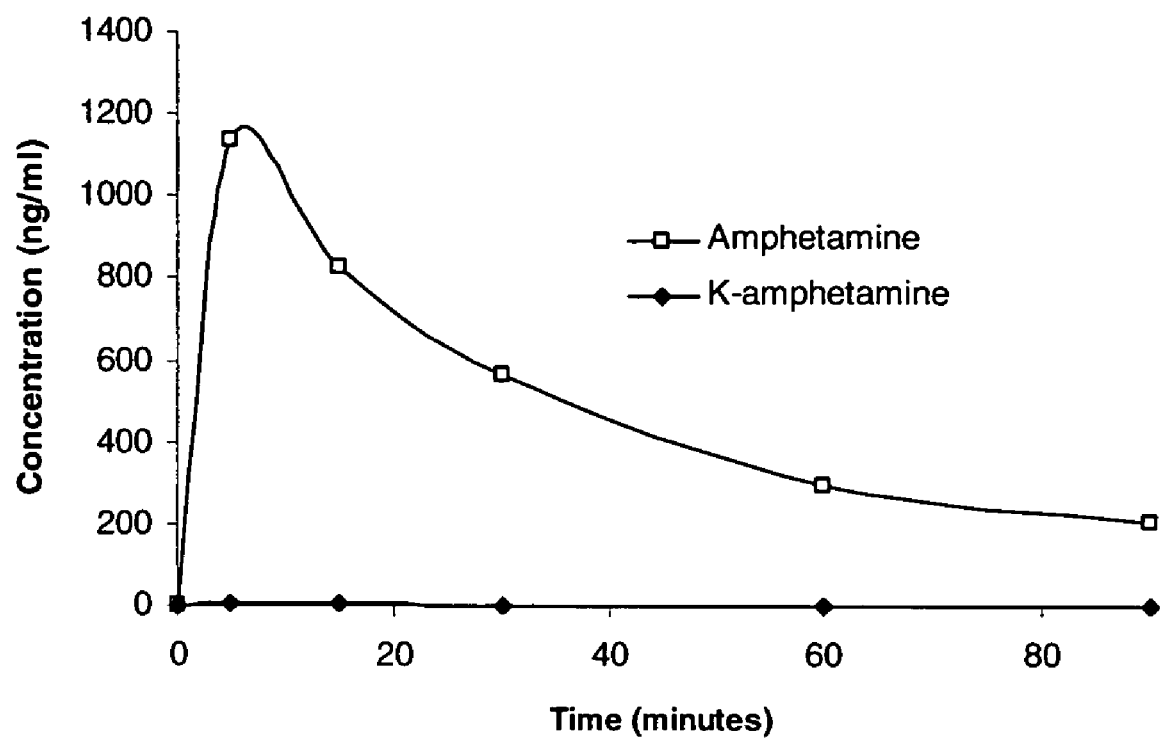
FIG. 45. Intranasal bioavailability of an abuse-resistant amphetamine amino acid conjugate (ELISA analysis).
Figure 46:
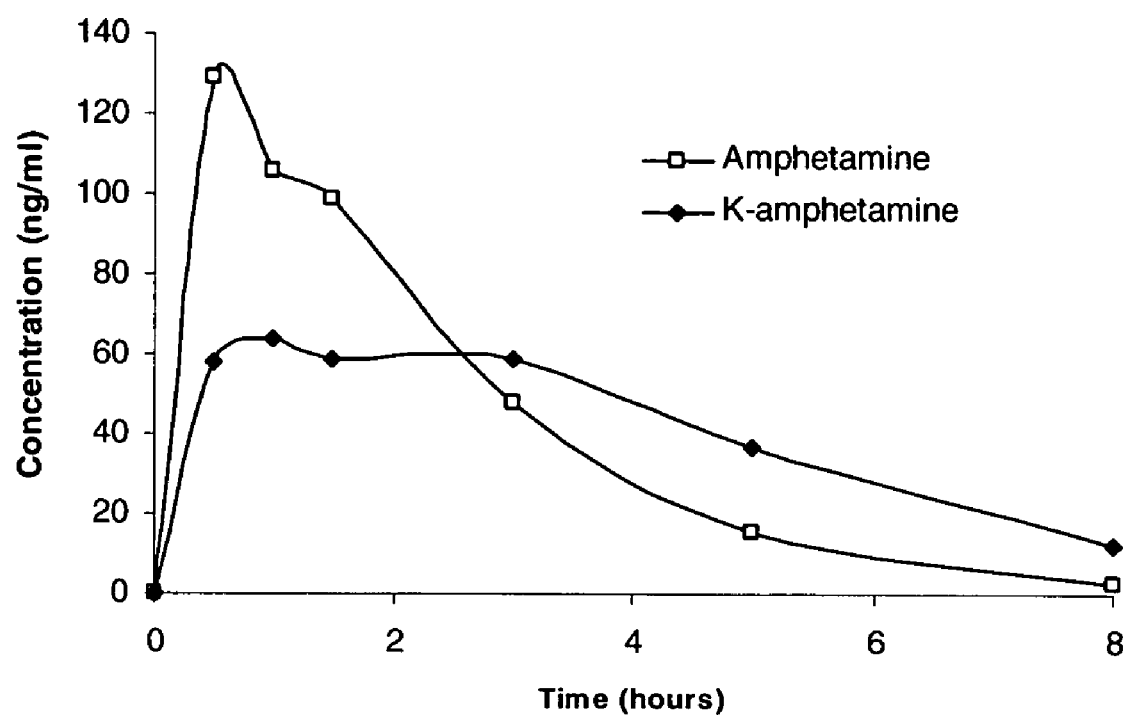
FIG. 46. Oral bioavailability of an abuse-resistant amphetamine amino acid conjugate (ELISA analysis).
Figure 47:
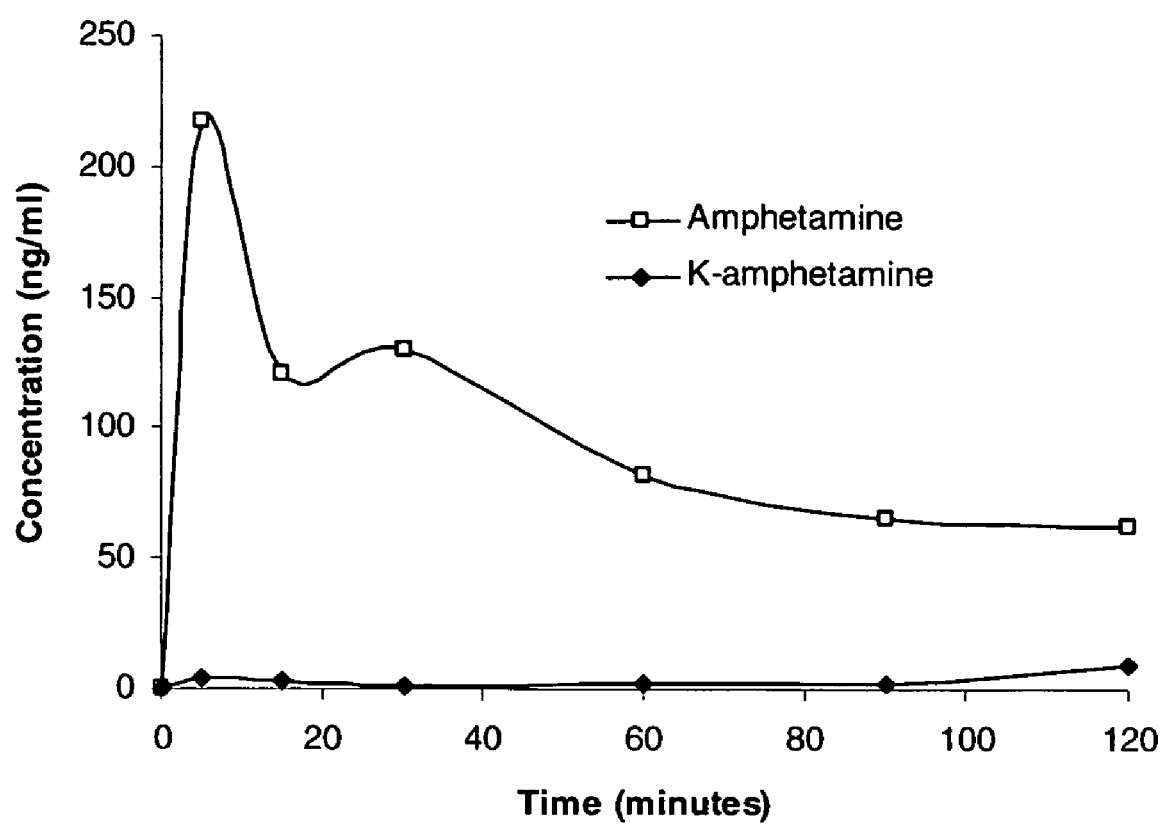
FIG. 47. Intravenous bioavailability of abuse-resistant amphetamine amino acid-, di-, and tri-peptide conjugates (ELISA analysis).
Figure 48:
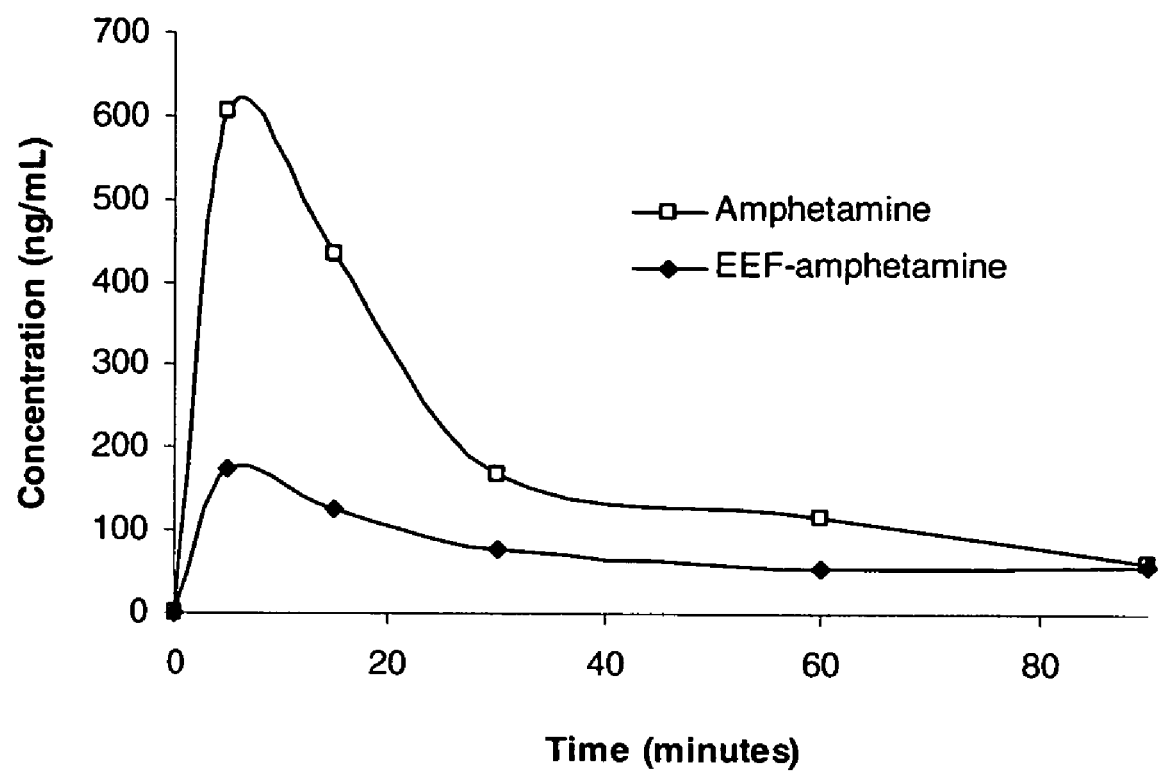
FIG. 48. Intranasal bioavailability of an abuse-resistant amphetamine amino tri-peptide conjugate (ELISA analysis).
Figure 49:
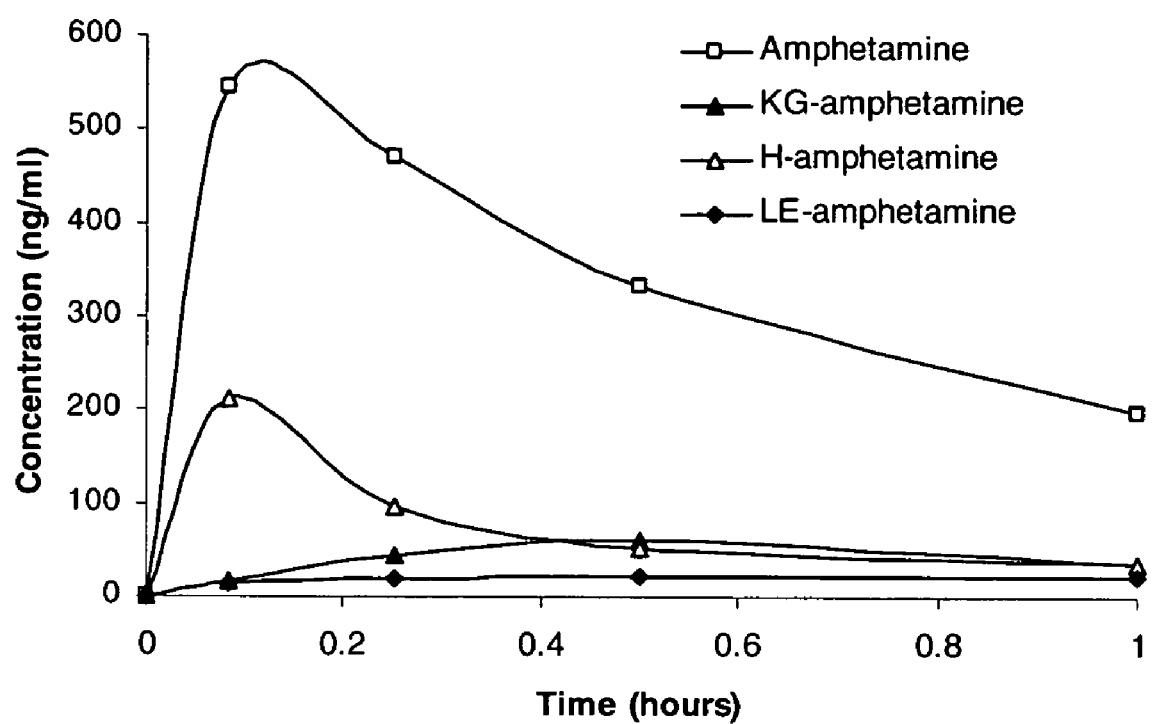
FIG. 49. Intranasal bioavailability of abuse-resistant amphetamine amino acid-, and di-peptide conjugates (ELISA analysis).
Figure 50:
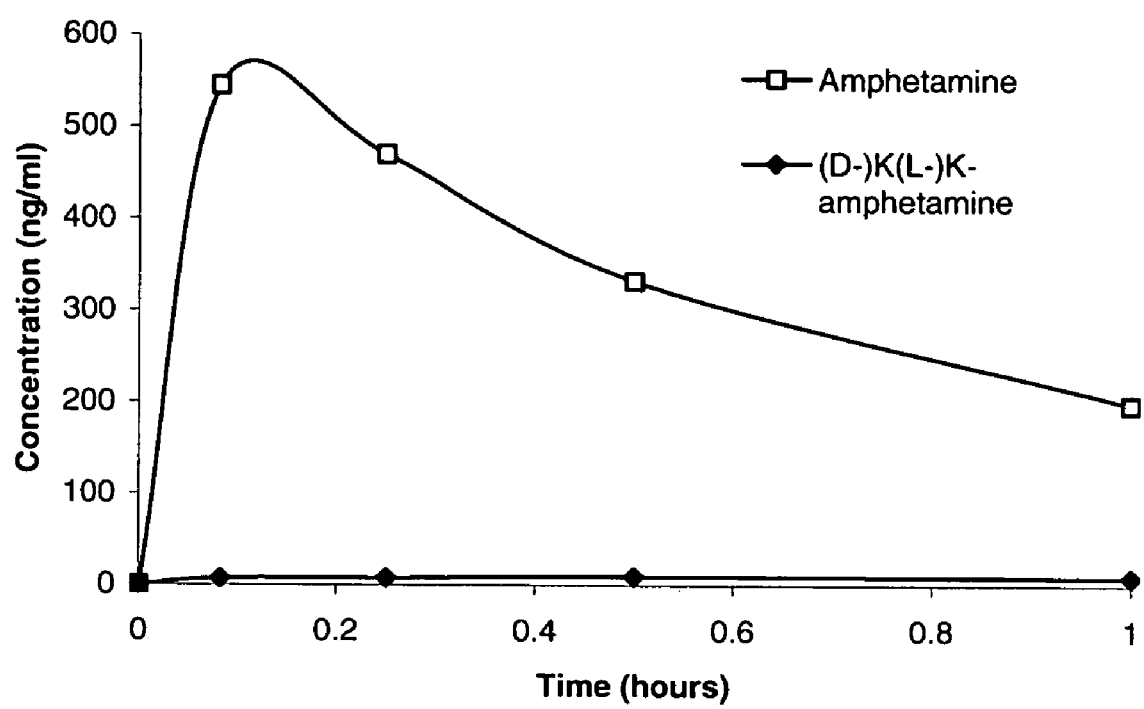
FIG. 50. Intranasal bioavailability of an abuse-resistant amphetamine di-peptide conjugate containing D-and L-amino acid isomers (ELISA analysis).

Pharmacodynamic Response to Amphetamine vs. L-lysine-d-amphetamine by Intravenous (IV) Administration Male Sprague-Dawley rats were dosed by intravenous administration with 1.0 mg/kg of d-amphetamine or L-lysine-d-amphetamine containing the equivalent amount of amphetamine. The activity vs. time (3 hours) is shown for d-amphetamine vs. L-lysine-d-amphetamine (FIG. 41). The activity induced by L-lysine-d-amphetamine was substantially decreased and time to peak activity was delayed. The activity expressed as total activity counts over a three hour period of time is shown in FIG. 41. The increase in activity over baseline of L-lysine-d-amphetamine was 34% for L-lysine-d-amphetamine when compared to activity observed for d-amphetamine dosed animals (Table 43).

TABLE 43

Total activity counts after d-amphetamine vs. L-lysine-d-amphetamine Following Intravenous (IV) Administration.

| Drug | n | Total Activity Counts 3 h | Above Baseline | Percent d-amphetamine |
|---|---|---|---|---|
| d-amphetamine | 3 | 1659 | 1355 | 100 |
| L-lysine-d-amphetamine | 4 | 767 | 463 | 34 |
| Water | 1 | 304 | 0 | 0 |

Example 24

Decrease in Toxicity of Orally Administered L-lysine-d-amphetamine

Three male and three female Sprague Dawley rats per group were given a single oral administration of L-lysine-d-amphetamine at 0.1, 1.0, 10, 60, 100 or 1000 mg/kg (Table 44). Each animal was observed for signs of toxicity and death on Days 1–7 (with Day 1 being the day of the dose) and one rat/sex/group was necropsied upon death (scheduled or unscheduled).

TABLE 44

Dosing Chart Oral Administration of L-lysine-d-amphetamine Toxicity Testing.

| Groups | No. of Animals M | F | Test Article | Dosages (mg/kg) | Concentrations (mg/mL) |
|---|---|---|---|---|---|
| 1 | 3 | 3 | L-lysine-d-amphetamine | 0.1 | 0.01 |
| 2 | 3 | 3 | L-lysine-d-amphetamine | 1.0 | 0.1 |
| 3 | 3 | 3 | L-lysine-d-amphetamine | 10 | 1.0 |
| 4 | 3 | 3 | L-lysine-d-amphetamine | 60 | 6.0 |
| 5 | 3 | 3 | L-lysine-d-amphetamine | 100 | 10 |
| 6 | 3 | 3 | L-lysine-d-amphetamine | 1000 | 100 |

Key observations of this study include:

All animals in Groups 1–3 showed no observable signs throughout the conduct of the study.

All animals in Groups 4–6 exhibited increased motor activity within two hours post-dose and which lasted into Day 2.

One female rat dosed at 1000 mg/kg was found dead on Day 2. Necropsy revealed chromodacryorrhea, chromorhinorrhea, distended stomach (gas), enlarged adrenal glands, and edematous and distended intestines.

A total of 4 rats had skin lesions of varying degrees of severity on Day 3.

One male rat dosed at 1000 mg/kg was euthanatized on Day 3 due to open skin lesions on the ventral neck.

All remaining animals appeared normal from Day 4 through Day 7.

Animals were observed for signs of toxicity at 1, 2 and 4 h post-dose, and once daily for 7 days after dosing and cage-side observations were recorded. Animals found dead, or sacrificed moribund were necropsied and discarded. A total of one animal/sex/group was necropsied upon scheduled or unscheduled death.

Cage-side observations and gross necropsy findings are summarized in Table 5. The data are not sufficient to establish a lethal dose, however, the study indicates that the lethal oral dose of L-lysine-d-amphetamine is above 1000 mg/kg, because only one death occurred out of a group of six animals. Although a second animal in this dose group was euthanatized on Day 3, it was done for humane reasons and it was felt that this animal would have fully recovered. Observations suggested drug-induced stress in Groups 4–6 that is characteristic of amphetamine toxicity (NTP, 1990; NIOSH REGISTRY NUMBER: SI1750000; Goodman et. al., 1985). All animals showed no abnormal signs on Days 4–7 suggesting full recovery at each treatment level.

The lack of data to support an established lethal dose is believed to be due to a putative protective effect of conjugating amphetamine with lysine. Intact L-lysine-d-amphetamine has been shown to be inactive, but becomes active upon metabolism into the unconjugated form (d-amphetamine). Thus, at high doses, saturation of metabolism of L-lysine-d-amphetamine into the unconjugated form may explain the lack of observed toxicity, which was expected at doses greater than 100 mg/kg, which is consistent with d-amphetamine sulfate (NTP, 1990). The formation rate of d-amphetamine and the extent of the formation of amphetamine may both attribute to the reduced toxicity. Alternatively, oral absorption of L-lysine-d-amphetamine may also be saturated at such high concentrations, which may suggest low toxicity due to limited bioavailability of L-lysine-d-amphetamine.

Example 25

In Vitro Assessment of L-lysine-d-amphetamine Pharmacodynamic Activity.

It was anticipated that the acylation of amphetamine, as in the amino acid conjugates discussed here, would significantly reduce the stimulant activity of the parent drug. For example, Marvola (1976) showed that N-acetylation of amphetamine completely abolished the locomotor activity increasing effects in mice. To confirm that the conjugate was not directly acting as a stimulant, we tested (Novascreen, Hanover, Md.) the specific binding of Lys-Amp ($10^{-9}$ to $10^{-5}$ M) to human recombinant dopamine and norepinephrine transport binding sites using standard radioligand binding assays. The results (see Table 45) indicate that the Lys-Amp did not bind to these sites. It seems unlikely that the conjugate retains stimulant activity in light of these results. (Marvola, M. (1976). "Effect of acetylated derivatives of some sympathomimetic amines on the acute toxicity, locomotor activity and barbiturate anesthesia time in mice." *Acta Pharmacol Toxicol (Copenh)* 38(5): 474–89).

TABLE 45

Results From Radioligand Binding Experiments with L-lysine-d-amphetamine

| Assay | Radioligand | Reference Compound | Ki (M) for Ref. Cpd. | Activity* |
|---|---|---|---|---|
| NE Transporter | [3H]-Nisoxetine | Desipramine | $4.1 \times 10^{-9}$ | No |
| DA Transporter | [3H]-WIN35428 | GBR-12909 | $7.7 \times 10^{-9}$ | No |

*No activity is defined as producing between −20% and 20% inhibition of radioligand binding (Novascreen).

Example 26

In Vitro Assessment "Kitchen Tests" to Release Amphetamine

It was anticipated that attempts would be made by illicit chemists to treat the compound with various easily accessible physical and chemical methods by which to release free amphetamine from the conjugate. An abuse-resistant preparation would have the additional feature of not releasing d-amphetamine when exposed to water, acid (vinegar), base (baking powder and baking soda), and heat. In several tests with L-lysine-d-amphetamine and GGG-Amp, no amphetamine was detected after the following treatments:

decrease in Cmax (74%). Additionally, $Gly_3$-Amp showed a decrease in bioavailability relative to amphetamine by intranasal and intravenous routes.

TABLE 46

Percent Bioavailability of Amino Acid Amphetamine Compounds Administered by Oral, Intranasal or Intravenous Routes

| Drug | Oral | | Intranasal | | Intravenous | |
| --- | --- | --- | --- | --- | --- | --- |
| | Percent AUC | Percent Cmax | Percent AUC | Percent Cmax | Percent AUC | Percent Cmax |
| Amphetamine | 100 | 100 | 100 | 100 | 100 | 100 |
| E-Amp | 73 | 95 | NA | NA | NA | NA |
| EE-Amp | 26 | 74 | NA | NA | NA | NA |
| L-Amp | 65 | 81 | NA | NA | NA | NA |
| S-Amp | 79/55 | 62/75 | 76 | 65 | NA | NA |
| GG-Amp | 79 | 88 | 88 | 85 | NA | NA |
| GGG-Amp | 111/68 | 74/73 | 32 | 38 | 45 | 46 |
| F-Amp | 95 | 91 | 97 | 95 | 87 | 89 |
| EEF-Amp | 42 | 73 | 39 | 29 | NA | NA |
| FF-Amp | 27 | 64 | NA | NA | NA | NA |
| Gulonate-Amp | 1 | 1 | 0.4 | 0.5 | 3 | 5 |
| K-Amp | 98 | 55 | 0.5 | 0.5 | 3 | 3 |
| KG-Amp | 69 | 71 | 13 | 12 | NA | NA |
| dK/K-Amp | 16 | 7 | 2 | 2 | NA | NA |
| LE-Amp | 40 | 28 | 6 | 6 | NA | NA |
| H-Amp | 16 | 21 | 22 | 42 | NA | NA |

| | Vinegar | Tap Water | Baking Powder | Baking Soda |
| --- | --- | --- | --- | --- |
| L-lysine-d-amphetamine | 0% | 0% | 0% | 0% |
| $Gly_3$-Amp | 0% | 0% | 0% | 0% |

Samples were heated to boiling for 20–60 minutes in each

Example 27

Bioavailability of Various Amino Acid-Amphetamine Compounds Administered by Oral, Intranasal, and Intravenous Routes.

Oral Administration. Male Sprague-Dawley rats were provided water ad libitum, fasted overnight, and dosed by oral gavage with amphetamine or amino acid-amphetamine conjugates containing the equivalent amount of amphetamine.

Intranasal Administration. Male Sprague-Dawley rats were dosed by intranasal administration with 1.8 mg/kg of amphetamine or lysine-amphetamine containing the equivalent amount of amphetamine.

The relative in vivo performance of various amino acid-amphetamine compounds is shown in FIGS. 42–50 and summarized in Table 46. Intranasal bioavailability of amphetamine from Ser-Amp was decreased to some degree relative to free amphetamine. However, this compound was not bioequivalent with amphetamine by the oral route of administration. Phenylalanine was bioequivalent with amphetamine by the oral route of administration, however, little or no decrease in bioavailability by parenteral routes of administration was observed. $Gly_3$-Amp had nearly equal bioavailability (90%) by the oral route accompanied by a Example 28

Decreased Oral $C_{max}$ of d-Amphetamine Conjugates

Male Sprague-Dawley rats were provided water ad libitum, fasted overnight and dosed by oral gavage with amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 29

Decreased Intranasal Bioavailability (AUC and $C_{max}$) of d-Amphetamine Conjugates.

Male Sprague-Dawley rats were provided water ad libitum and doses were administered by placing 0.02 ml of water containing amphetamine conjugate or d-amphetamine sulfate into the nasal flares. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 30

Decreased Intravenous Bioavailability (AUC and $C_{max}$) of d-Amphetamine Conjugates.

Male Sprague-Dawley rats were provided water ad libitum and doses were administered by intravenous tail vein injection of 0.1 ml of water containing amphetamine conjugate or d-amphetamine sulfate. All doses contained equivalent amounts of d-amphetamine base. Plasma d-amphetamine concentrations were measured by ELISA (Amphetamine Ultra, 109319, Neogen, Corporation, Lexington, Ky.). The assay is specific for d-amphetamine with only minimal reactivity (0.6%) of the major d-amphetamine metabolite (para-hydroxy-d-amphetamine) occurring. Plasma d-amphetamine and L-lysine-d-amphetamine concentrations were measured by LC/MS/MS where indicated in examples.

Example 31

Attachment of Amphetamine to Variety of Chemical Moieties

The above examples demonstrate the use of an amphetamine conjugated to a chemical moiety, such as an amino acid, which is useful in reducing the potential for overdose while maintaining its therapeutic value. The effectiveness of binding amphetamine to a chemical moiety was demonstrated through the attachment of amphetamine to lysine (K), however, the above examples are meant to be illustrative only. The attachment of amphetamine to any variety of chemical moieties (i.e. peptides, glycopeptides, carbohydrates, nucleosides, or vitamins) is described below through similar procedures using the following exemplary starting materials.

Amphetamine Synthetic Examples

Synthesis of Gly$_2$-Amp
Gly$_2$-Amp was synthesized by a similar method except the amino acid starting material was Boc-Gly-Gly-OSu.

Synthesis of Glu$_2$-Phe-Amp
Glu$_2$-Phe-Amp was synthesized by a similar method except the amino acid starting material was Boc-Glu(OtBu)-Glu(OtBu)-OSu and the starting drug conjugate was Phe-Amp (see Phe-Amp synthesis).

Synthesis of His-Amp
His-Amp was synthesized by a similar method except the amino acid starting material was Boc-His(Trt)-OSu.

Synthesis of Lys-Gly-Amp
Lys-Gly-Amp was synthesized by a similar method except the amino acid starting material was Boc-Lys(Boc)-OSu and the starting drug conjugate was Gly-Amp (see Gly-Amp synthesis).

Synthesis of Lys-Glu-Amp
Lys-Glu-Amp was synthesized by a similar method except the amino acid starting material was Boc-Lys(Boc)-OSu and the starting drug conjugate was Glu-Amp.

Synthesis of Glu-Amp
Glu-Amp was synthesized by a similar method except the amino acid starting material was Boc-Glu(OtBu)-OSu.

Synthesis of (d)-Lys-(l)-Lys-Amp
(d)-Lys-(l)-Lys-Amp was synthesized by a similar method except the amino acid starting material was Boc-(d)-Lys(Boc)-(l)-Lys(Boc)-OSu.

Synthesis of Gulonic acid-Amp
Gul-Amp was synthesized by a similar method except the carbohydrate starting material was gulonic acid-OSu.

Example 32

Lack of Detection of L-lysine-d-amphetamine in Brain Tissue Following Oral Administration.

Figure 51A:
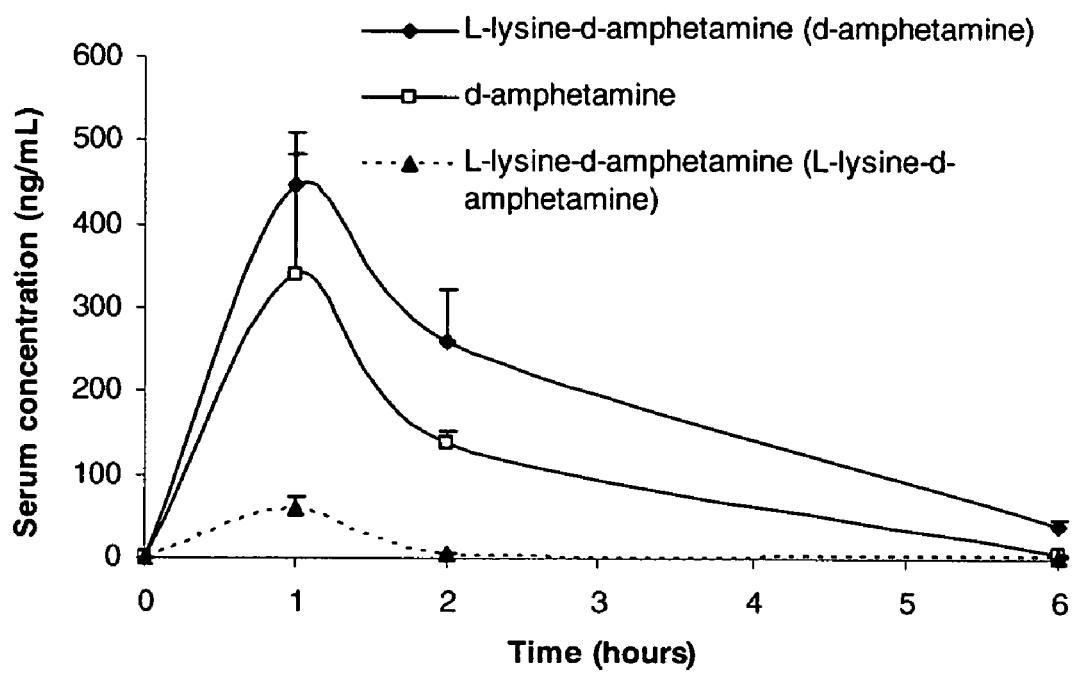
FIGS. 51A–B. Plasma concentrations of d-amphetamine and L-lysine-d-amphetamine in ng/mL for the serum levels (FIG. 51A), and in ng/g for brain tissue (FIG. 51B), following oral administration of L-lysine-d-amphetamine or d-amphetamine sulfate (5 mg/kg d-amphetamine base) to rats. Serum and brain tissue d-amphetamine and L-lysine-d-amphetamine concentrations were measured by LC/MS/MS (compound indicated in parenthesis).
Figure 51B:
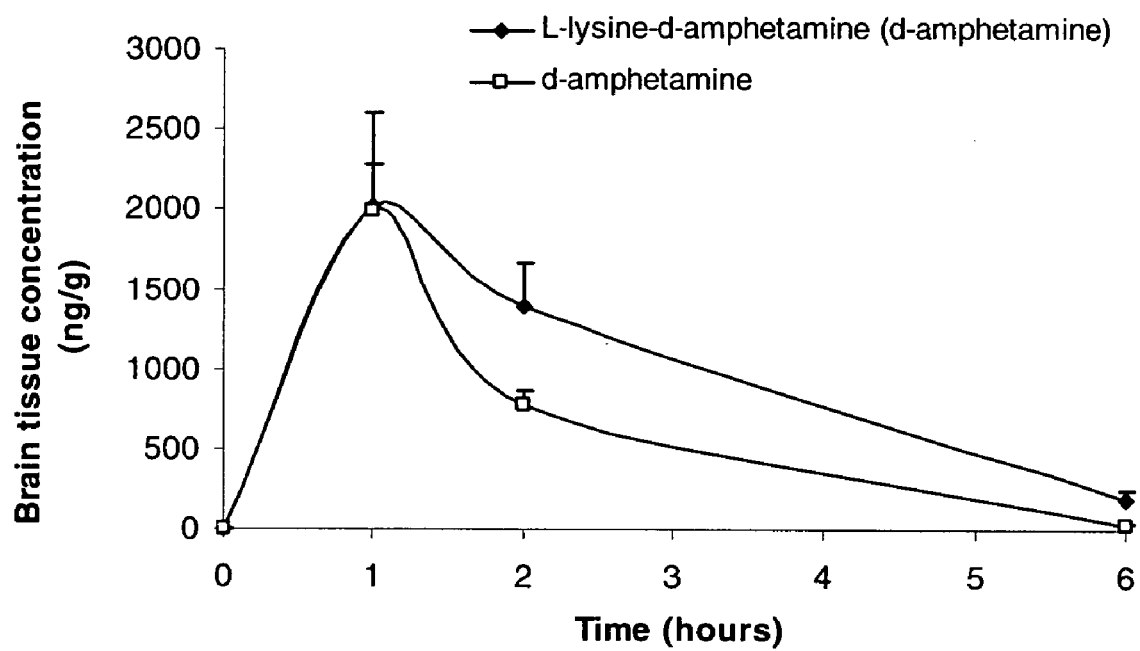

Male Sprague-Dawley rats were provided water ad libitum, fasted overnight and dosed by oral gavage with L-lysine-d-amphetamine or d-amphetamine sulfate. All doses contained equivalent amounts of d-amphetamine base. As shown in FIGS. 51A–B, similar levels of d-amphetamine were detected in serum as well as in brain tissue following administration of d-amphetamine sulfate or L-lysine-d-amphetamine. The conjugate L-lysine-d-amphetamine, however, was present in appreciable amounts in serum but was not detected in brain tissue indicating that the conjugate does not cross the blood brain barrier to access the central nervous system site of action.

Example 33

Clinical Pharmacokinetic Evaluation and Oral Bioavailability of L-lysine-d-amphetamine Compared to Amphetamine Extended Release Products Adderall XR® and Dexadrine Spansule® Used in the Treatment of ADHD

TABLE 47

Treatment Groups and Dosage for Clinical Pharmacokinetic Evaluation of L-lysine-d-amphetamine Compared to Adderall XR ® or Dexadrine Spansule ®

| Drug | Treatment Group | Number of Subjects | Dose | Dose (mg) | Dose (amphetamine base) |
|---|---|---|---|---|---|
| L-lysine-d-amphetamine | A | 10 | 1 × 25 mg capsule | 25 | 7.37 |
| L-lysine-d-amphetamine | B | 10 | 3 × 25 mg capsules | 75 | 22.1 |
| Dexadrine Spansule ® | C | 10 | 3 × 10 mg capsules | 30 | 22.1 |
| Adderall XR ® | D | 10 | 1 × 30 mg capsules plus 1 × 5 mg capsule | 35 | 21.9 |

A clinical evaluation of the pharmacokinetics and oral bioavailability of L-lysine-d-amphetamine in humans was conducted. L-lysine-d-amphetamine was orally administered at doses approximating the lower (25 mg) and higher (75 mg) end of the therapeutic range based on d-amphetamine base content of the doses. Additionally, the higher dose was compared to doses of Adderall XR® (Shire) or Dexadrine Spansule® (GlaxoSmithKline) containing equivalent amphetamine base to that of the higher L-lysine-d-amphetamine dose. Treatment groups and doses are summarized in Table 47. All levels below limit quantifiable (blq<0.5 ng/mL) were treated as zero for purposes of pharmacokinetic analysis.

The concentrations of d-amphetamine and L-lysine-d-amphetamine intact conjugate following administration of L-lysine-d-amphetamine at the low and high dose for each individual subject as well as pharmacokinetic parameters are presented in Tables 48–51. The concentrations of d-amphetamine following administration of Adderall XR® or Dexadrine Spansule® for each individual subject as well as pharmacokinetic parameters are presented in Tables 52 and 53, respectively. Concentration-time curves showing L-lysine-d-amphetamine intact conjugate and d-amphetamine (nglmL, FIGS. 52A and 53A and uM, FIGS. 52B and 53B) are presented in FIGS. 52 and 53. Extended release of d-amphetamine from L-lysine-d-amphetamine was observed for both doses and pharmacokinetic parameters ($C_{max}$ and AUC) were proportional to doses when the lower and higher dose results were compared (Table 43, 50 and 54; FIGS. 52 and 53). Significant levels of d-amphetamine were not observed until one-hour post administration. Only small amounts (1.6 and 2.0 percent of total drug absorption, respectively for 25 and 75 mg doses; $AUC_{inf}$-molar basis) of L-lysine-d-amphetamine intact conjugate were detected with levels peaking at about one hour (Table 49 and 51). The small amount of intact conjugate absorbed was rapidly and completely eliminated, with no detectable concentrations present by five hours, even at the highest dose.

In a cross-over design (identical subjects received Adderall XR® doses following a 7-day washout period), the higher L-lysine-d-amphetamine dose was compared to an equivalent dose of Adderall XR®. Adderall XR® is a once-daily extended release treatment for ADHD that contains a mixture of d-amphetamine and l-amphetamine salts (equal amounts of d-amphetamine sulfate, d-/l-amphetamine sulfate, d-amphetamine saccharate, and d-/l-amphetamine aspartate). An equivalent dose of extended release Dexadrine Spansule® (contains extended release formulation of d-amphetamine sulfate) was also included in the study. As observed in pharmacokinetic studies in rats, oral administration of L-lysine-d-amphetamine resulted in d-amphetamine concentration-time curves similar to those of Adderall XR® and Dexadrine Spansule® (FIGS. 54 and 55). The bioavailability ($AUC_{inf}$) of d-amphetamine following administration of L-lysine-d-amphetamine was approximately equivalent to both extended release amphetamine products (Table 54). Over the course of twelve hours, typically the time needed for effective once-daily treatment of ADHD, the bioavailability for L-lysine-d-amphetamine was approximately equivalent to that of Adderall XR® (d-amphetamine plus l-amphetamine levels) and over twenty percent higher than that of Dexadrine Spansule®. Based on the results of this clinical study, L-lysine-d-amphetamine would be an effective once-daily treatment for ADHD. Moreover, L-lysine-d-amphetamine afforded similar pharmacokinetics in humans and animal models, namely, delayed release of d-amphetamine resulting in extended release kinetics. Based on these observations L-lysine-d-amphetamine should also have abuse-resistant properties in humans.

TABLE 48

Individual Subject d-amphetamine Concentrations and Pharmacokinetic Parameters Following Oral Administration of a 25 mg Dose of L-lysine-d-amphetamine to Humans.

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 0 | 0 | 0.625 | 0 | 0 | 0 | 0 | 0.78 | 0.769 | 0 | 0.2 | 0.4 | 162.1 |
| 1 | 4.29 | 2.95 | 8.67 | 3.36 | 8.33 | 1.1 | 10 | 10.5 | 14 | 3.15 | 6.6 | 4.2 | 63.6 |
| 1.5 | 10 | 12.7 | 16 | 13.8 | 21.4 | 3.94 | 24.7 | 19.5 | 24 | 15.1 | 16.1 | 6.5 | 40.3 |
| 2 | 16.3 | 18.4 | 17 | 21 | 25.9 | 9.29 | 30.9 | 23.6 | 30 | 21.7 | 21.4 | 6.6 | 30.8 |
| 3 | 16.5 | 19.6 | 16.7 | 26.1 | 27 | 17.7 | 30.2 | 23.5 | 27.6 | 28.9 | 23.4 | 5.3 | 22.7 |
| 4 | 23.9 | 18.8 | 14.1 | 24.5 | 30.1 | 17.9 | 33.2 | 21.2 | 24.7 | 25.3 | 23.4 | 5.7 | 24.3 |
| 5 | 21.2 | 18.9 | 14.6 | 21.6 | 22.6 | 17.2 | 27 | 20 | 20.2 | 24.2 | 20.8 | 3.5 | 16.9 |
| 6 | 21.8 | 18 | 12.5 | 21.6 | 23.7 | 15.7 | 25.8 | 18.2 | 20.3 | 20.5 | 19.8 | 3.9 | 19.6 |
| 7 | 18.9 | 15.8 | 12.1 | 17.8 | 20.6 | 14.5 | 26.6 | 21 | 18.3 | 21.8 | 18.7 | 4.1 | 21.9 |
| 8 | 19.3 | 16.6 | 10.4 | 17.9 | 20 | 14.2 | 25.7 | 13.6 | 18.8 | 20.1 | 17.7 | 4.2 | 24.1 |
| 10 | 18.8 | 13.6 | 9.8 | 15.3 | 19.3 | 13.7 | 22.4 | 15.1 | 15.3 | 15.9 | 15.9 | 3.5 | 22.1 |
| 12 | 15.8 | 12.6 | 6.92 | 11.5 | 15.8 | 11.2 | 17.9 | 12 | 13.7 | 15.2 | 13.3 | 3.1 | 23.6 |
| 16 | 13.4 | 10.5 | 6.56 | 9.53 | 14.3 | 10.7 | 12.5 | 10.3 | 10 | 13 | 11.1 | 2.3 | 20.5 |
| 24 | 8.03 | 5.81 | 2.65 | 4.9 | 5.8 | 5.9 | 6.57 | 6.13 | 4.52 | 5.45 | 5.6 | 1.4 | 25.1 |
| 48 | 1.57 | 1.36 | 0 | 1.26 | 0.795 | 1.44 | 1.24 | 1.23 | 0.864 | 0.586 | 1.0 | 0.5 | 46.1 |
| 72 | 0 | 0 | 0 | 0 | 0 | 0 | 0 | 0 | 0 | 0 | 0 | 0 | 0 |
| Parameter | | | | | | | | | | | | | |
| $AUC_{0-12h}$ (ng · h/mL) | 204.0 | 177.4 | 140.4 | 204.9 | 242.7 | 152.4 | 284.6 | 199.2 | 225.5 | 223.3 | 205.4 | 42.5 | 20.7 |
| $AUC_{last}$ (ng · h/mL) | 463.3 | 375.1 | 201.4 | 378.5 | 462.7 | 350.7 | 515.2 | 397.9 | 395.7 | 426.1 | 396.7 | 84.8 | 21.4 |
| $AUC_{inf}$ (ng · h/mL) | 486.7 | 397.1 | 233.5 | 398.8 | 472 | 374 | 532.5 | 416.4 | 407 | 432.2 | 415.0 | 80.1 | 19.3 |
| $C_{max}$ (ng/mL) | 23.9 | 19.6 | 17 | 26.1 | 30.1 | 17.9 | 33.2 | 23.6 | 30 | 28.9 | 25.0 | 5.6 | 22.3 |
| $T_{max}$ (hours) | 4 | 3 | 2 | 3 | 4 | 4 | 4 | 2 | 2 | 3 | 3.1 | 0.876 | 28.2 |
| $T_{1/2}$ (hours) | 10.32 | 11.18 | 8.36 | 11.18 | 8.16 | 11.22 | 9.68 | 10.43 | 9.06 | 7.22 | 9.68 | 1.43 | 14.7 |

TABLE 49

Individual Subject L-lysine-d-amphetamine Intact Conjugate Concentrations and Pharmacokinetic Parameters Following Oral Administration of a 25 mg Dose of L-lysine-d-amphetamine to Humans.

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 4.1 | 5.5 | 10.0 | 0.0 | 3.6 | 0.0 | 9.2 | 9.6 | 8.9 | 0.0 | 5.1 | 4.2 | 82.0 |

TABLE 49-continued

Individual Subject L-lysine-d-amphetamine Intact Conjugate Concentrations and Pharmacokinetic Parameters Following Oral Administration of a 25 mg Dose of L-lysine-d-amphetamine to Humans.

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| 1 | 9.2 | 11.2 | 15.2 | 12.5 | 9.1 | 2.7 | 20.1 | 10.5 | 10.8 | 10.9 | 11.2 | 4.5 | 39.7 |
| 1.5 | 4.0 | 4.4 | 6.1 | 7.5 | 3.6 | 6.2 | 6.6 | 2.8 | 4.2 | 8.4 | 5.4 | 1.8 | 34.1 |
| 2 | 2.1 | 1.4 | 2.5 | 2.9 | 1.9 | 4.0 | 2.3 | 0 | 1.7 | 3.1 | 2.2 | 1.1 | 48.8 |
| 3 | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 |
| 72 | 0 | 0 | 0 | 0 | 0 | 0 | 0 | 0 | 0 | 0 | 0 | 0 | 0 |
| Parameter | | | | | | | | | | | | | |
| $AUC_{last}$ (ng·h/mL) | 9.18 | 10.95 | 16.31 | 10.68 | 8.583 | 5.439 | 18.51 | 10.77 | 12.35 | 10.41 | 11.32 | 3.74 | 33.1 |
| $AUC_{inf}$ (ng·h/mL) | 10.62 | 11.64 | 17.66 | 12.65 | 9.759 | — | 19.56 | — | 13.3 | 12.83 | 13.50 | 3.40 | 25.2 |
| $C_{max}$ (ng/mL) | 9.18 | 11.2 | 15.2 | 12.5 | 9.05 | 6.18 | 20.1 | 10.5 | 10.8 | 10.9 | 11.56 | 3.80 | 32.9 |
| $T_{max}$ (hours) | 1 | 1 | 1 | 1 | 1 | 1.5 | 1 | 1 | 1 | 1 | 1.05 | 0.16 | 15.1 |
| $T_{1/2}$ (hours) | 0.47 | 0.34 | 0.38 | 0.47 | 0.44 | — | 0.32 | — | 0.38 | 0.55 | 0.419 | 0.077 | 18.5 |

TABLE 50

Individual Subject d-amphetamine Concentrations and Pharmacokinetic Parameters Following Oral Administration of a 75 mg Dose of L-lysine-d-amphetamine to Humans.

| | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 0 | 0.748 | 0.506 | 0 | 0 | 0.779 | 0.525 | 0 | 3 | 1.85 | 0.7 | 1.0 | 132.2 |
| 1 | 11.9 | 14.4 | 12.6 | 7.26 | 5.9 | 10.3 | 7.2 | 23.1 | 23 | 27.9 | 14.4 | 7.7 | 53.6 |
| 1.5 | 40.3 | 34.6 | 30.4 | 22.8 | 19.3 | 38.4 | 19 | 52.8 | 51.5 | 55.8 | 36.5 | 13.8 | 37.8 |
| 2 | 84.6 | 48.9 | 68.2 | 34.8 | 32.7 | 57.2 | 33.1 | 91.3 | 61.7 | 70.4 | 58.3 | 21.0 | 36.0 |
| 3 | 72.9 | 64.3 | 55.7 | 60.3 | 62.3 | 61.1 | 44.8 | 95.8 | 62.1 | 83.6 | 66.3 | 14.5 | 21.9 |
| 4 | 84.6 | 65.3 | 58.8 | 51.1 | 77.9 | 63.3 | 47.6 | 89.2 | 54.2 | 86 | 67.8 | 15.5 | 22.8 |
| 5 | 65 | 55.6 | 60.2 | 74 | 83.9 | 59.1 | 56.9 | 77.7 | 54.9 | 82.8 | 67.0 | 11.5 | 17.2 |
| 6 | 71 | 53.5 | 49.4 | 51.5 | 78.3 | 50.8 | 55.1 | 68.8 | 52.9 | 64 | 59.5 | 10.2 | 17.1 |
| 7 | 53.8 | 55.7 | 52.9 | 69.5 | 73.1 | 52.9 | 55.9 | 71.2 | 45.1 | 74.6 | 60.5 | 10.5 | 17.4 |
| 8 | 63.7 | 40.3 | 47.3 | 45.7 | 72.2 | 46.5 | 54.2 | 61.1 | 44.3 | 66.2 | 54.2 | 10.9 | 20.2 |
| 10 | 43.7 | 41.7 | 37 | 58.4 | 67 | 44.3 | 48.4 | 68 | 34.1 | 55.9 | 49.9 | 11.9 | 24.0 |
| 12 | 46.4 | 26.1 | 36.7 | 37.4 | 49.9 | 32.4 | 37.1 | 54.1 | 34.5 | 45.1 | 40.0 | 8.6 | 21.6 |
| 16 | 35.4 | 22.2 | 25.7 | 48 | 44.9 | 24.3 | 28.9 | 44.7 | 31.7 | 34.5 | 34.0 | 9.2 | 27.1 |
| 24 | 16.4 | 11.4 | 14.9 | 13.2 | 18.4 | 16.8 | 20.5 | 21.7 | 15.7 | 18.1 | 16.7 | 3.1 | 18.8 |
| 48 | 2.74 | 2.14 | | 4.17 | 2.73 | 3.75 | 4.81 | 2.81 | 4.26 | 3.36 | 3.4 | 0.9 | 25.9 |
| 72 | 0 | 0 | 0 | 1.07 | 0.661 | 0.687 | 1.49 | 0 | 0 | 0.553 | 0.4 | 0.5 | 120.2 |
| Parameter | | | | | | | | | | | | | |
| $AUC_{0-12h}$ (ng·h/mL) | 666.2 | 525.9 | 531.6 | 570.3 | 704.8 | 545.6 | 513.7 | 790.9 | 523.4 | 742.8 | 611.5 | 104.5 | 17.1 |
| $AUC_{last}$ (ng·h/mL) | 1266 | 918.7 | 1031 | 1257 | 1442 | 1123 | 1223 | 1549 | 1143 | 1417 | 1237.0 | 194.0 | 15.7 |
| $AUC_{inf}$ (ng·h/mL) | 1301 | 948.3 | 1072 | 1278 | 1451 | 1133 | 1251 | 1582 | 1154 | 1425 | 1259.5 | 191.3 | 15.2 |
| $C_{max}$ (ng/mL) | 84.6 | 65.3 | 68.2 | 74 | 83.9 | 63.3 | 56.9 | 95.8 | 62.1 | 86 | 74.0 | 12.9 | 17.4 |
| $T_{max}$ (hours) | 4 | 4 | 2 | 5 | 5 | 4 | 5 | 3 | 3 | 4 | 3.9 | 1.0 | 25.5 |
| $T_{1/2}$ (hours) | 8.78 | 9.59 | 10.02 | 13.26 | 9.24 | 10.41 | 12.8 | 8.05 | 10.92 | 9.47 | 10.3 | 1.7 | 16.3 |

TABLE 51

Individual Subject L-lysine-d-amphetamine Intact Conjugate Concentrations and Pharmacokinetic Parameters Following Oral Administration of a 75 mg Dose of L-lysine-d-amphetamine to Humans.

| | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 10.4 | 22.6 | 6.92 | 10.3 | 0 | 9.21 | 7.88 | 14.5 | 87.8 | 35.5 | 20.5 | 25.6 | 124.7 |
| 1 | 48 | 40.5 | 29 | 41.5 | 21.2 | 30.8 | 23.4 | 127 | 88.9 | 80.1 | 53.0 | 34.6 | 65.2 |
| 1.5 | 28.4 | 15.7 | 16.1 | 20.3 | 26.5 | 19 | 12.7 | 38.7 | 28.6 | 38 | 24.4 | 9.2 | 37.5 |
| 2 | 8.87 | 5.53 | 4.91 | 9 | 18.1 | 5.62 | 6.29 | 12.1 | 9.75 | 11.3 | 9.1 | 4.0 | 44.0 |
| 3 | 2.15 | 1.29 | 1.76 | 1.82 | 10.6 | 0 | 2.31 | 2.57 | 1.73 | 1.73 | 2.6 | 2.9 | 111.6 |
| 4 | 0 | 0 | 1.09 | 0 | 4.65 | 0 | 1.53 | 1.01 | 0 | 0 | 0.8 | 1.5 | 176.9 |
| 5 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 | 0 |
| 72 | 0 | 0 | 0 | 0 | 0 | 0 | 0 | 0 | 0 | 0 | 0 | 0 | 0 |
| Parameter | | | | | | | | | | | | | |
| $AUC_{last}$ (ng · h/mL) | 51.2 | 44.2 | 32.0 | 43.7 | 50.4 | 30.9 | 29.8 | 102.1 | 110.8 | 86.1 | 58.1 | 30.2 | 52.0 |
| $AUC_{inf}$ (ng · h/mL) | 52.5 | 45.0 | 33.0 | 44.9 | 52.3 | 34.2 | 31.4 | 102.9 | 111.7 | 87.0 | 59.5 | 29.9 | 50.2 |
| $C_{max}$ (ng/mL) | 48.0 | 40.5 | 29.0 | 41.5 | 26.5 | 30.8 | 23.4 | 127.0 | 88.9 | 80.1 | 53.6 | 34.1 | 63.6 |
| $T_{max}$ (hours) | 1 | 1 | 1 | 1 | 1.5 | 1 | 1 | 1 | 1 | 1 | 1.05 | 0.16 | 15.1 |
| $T_{1/2}$ (hours) | 0.43 | 0.4 | 0.61 | 0.43 | 1.02 | 0.41 | 0.75 | 0.56 | 0.38 | 0.35 | 0.534 | 0.211 | 39.6 |

TABLE 52

Individual Subject d-amphetamine Concentrations and Pharmacokinetic Parameters Following Oral Administration of a 35 mg Dose of Adderall XR ® (equivalent to 75 mg dose of L-lysine-d-amphetamine based on amphetamine base content) to Humans.

| | Subject 101 | Subject 104 | Subject 106 | Subject 108 | Subject 109 | Subject 111 | Subject 114 | Subject 115 | Subject 118 | Subject 119 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 7.9 | 2.3 | 2.8 | 0.6 | 2.2 | 5.7 | 0 | 16 | 2.3 | 5.3 | 4.5 | 4.7 | 104.3 |
| 1 | 37.6 | 28.9 | 23.3 | 13.7 | 29.8 | 38.2 | 17.9 | 46.2 | 28.8 | 48.8 | 31.3 | 11.5 | 36.6 |
| 1.5 | 49.9 | 42.3 | 31.1 | 23.7 | 39.1 | 34.4 | 30.8 | 65.4 | 34.1 | 53 | 40.4 | 12.5 | 31.0 |
| 2 | 65.9 | 45.8 | 29.2 | 37.4 | 46.2 | 65.4 | 40 | 64.4 | 37 | 67.8 | 49.9 | 14.6 | 29.2 |
| 3 | 95.3 | 51.7 | 36.7 | 23.6 | 64.7 | 62.9 | 44.7 | 56.5 | 31.1 | 64.8 | 53.2 | 20.7 | 38.9 |
| 4 | 83.7 | 73.3 | 56.7 | 40 | 67 | 76.6 | 56.3 | 53.1 | 33.5 | 73.3 | 61.4 | 16.3 | 26.6 |
| 5 | 77.4 | 75.2 | 71.6 | 62.1 | 75.9 | 76.4 | 51.5 | 61.4 | 56.8 | 82.4 | 69.1 | 10.3 | 14.9 |
| 6 | 71.5 | 72.1 | 64 | 59.8 | 66.9 | 63.5 | 56.8 | 59.8 | 58.7 | 85.7 | 65.9 | 8.7 | 13.2 |
| 7 | 72.3 | 63.6 | 71 | 57.9 | 70.6 | 69.7 | 51.9 | 48.1 | 53.7 | 79.7 | 63.9 | 10.5 | 16.4 |
| 8 | 60.4 | 57.1 | 53.8 | 53 | 72 | 66.9 | 56.2 | 56.4 | 51.7 | 66.7 | 59.4 | 6.9 | 11.6 |
| 10 | 50.4 | 45.5 | 53 | 50.7 | 67.6 | 57.4 | 49.1 | 66.6 | 48 | 71.3 | 56.0 | 9.3 | 16.6 |
| 12 | 42.5 | 41.3 | 45.4 | 32.9 | 53.1 | 46 | 37.3 | 74.7 | 42.2 | 60.2 | 47.6 | 12.2 | 25.7 |
| 16 | 31.1 | 29.6 | 35.7 | 39 | 45.2 | 33.9 | 34.3 | 64.9 | 29 | 40.5 | 38.3 | 10.6 | 27.7 |
| 24 | 14.9 | 15.1 | 22.1 | 19.5 | 21.7 | 21.2 | 20.7 | 35.7 | 17.9 | 20.5 | 20.9 | 5.8 | 27.7 |
| 48 | 2.5 | 4.2 | 3.8 | 5.9 | 5.4 | 3.8 | 7.3 | 5.1 | 3.9 | 3 | 4.5 | 1.4 | 32.1 |
| 72 | 0 | 0.3 | 1 | 1 | 0.3 | 1.1 | 2.7 | 0.3 | 0 | 0 | 0.7 | 0.8 | 124.7 |
| Parameter | | | | | | | | | | | | | |
| $AUC_{0-12h}$ (ng · h/mL) | 731.2 | 625.0 | 582.6 | 504.3 | 711.6 | 698.5 | 535.4 | 683.5 | 509.8 | 793.2 | 637.5 | 101.1 | 15.9 |
| $AUC_{last}$ (ng · h/mL) | 1270 | 1230 | 1343 | 1269 | 1568 | 1436 | 1354 | 1920 | 1101 | 1520 | 1401.1 | 229.0 | 16.3 |
| $AUC_{inf}$ (ng · h/mL) | 1301 | 1234 | 1358 | 1286 | 1571 | 1454 | 1418 | 1923 | 1164 | 1557 | 1426.6 | 218.9 | 15.3 |
| $C_{max}$ (ng/mL) | 95.3 | 75.2 | 71.5 | 62 | 75.9 | 76.5 | 56.8 | 74.7 | 58.8 | 85.8 | 73.3 | 11.9 | 16.3 |
| $T_{max}$ (hours) | 3 | 5 | 5 | 5 | 5 | 4 | 6 | 12 | 6 | 6 | 5.70 | 2.41 | 42.2 |
| $T_{1/2}$ (hours) | 8.65 | 9.01 | 10.57 | 11.58 | 8.37 | 10.78 | 16.4 | 7.25 | 11.05 | 8.54 | 10.22 | 2.59 | 25.3 |

TABLE 53

Individual Subject d-amphetamine Concentrations and Pharmacokinetic Parameters Following Oral Administration of a 30 mg Dose of Dexadrine Spansule ® (equivalent to 75 mg dose of L-lysine-d-amphetamine based on amphetamine base content) to Humans.

| | Subject 102 | Subject 103 | Subject 105 | Subject 107 | Subject 110 | Subject 112 | Subject 113 | Subject 116 | Subject 117 | Subject 120 | Mean | SD | CV % |
|---|---|---|---|---|---|---|---|---|---|---|---|---|---|
| Time Hours | | | | | | | | | | | | | |
| 0 | 0 | 0 | 0 | 0 | 0 | 0 | 0 | 0 | 0 | 0 | 0 | 0 | 0 |
| 0.5 | 1.2 | 2.68 | 1.37 | 1.4 | 1.16 | 2.36 | 6.75 | 2.63 | 4.95 | 3.43 | 2.8 | 1.8 | 65.5 |
| 1 | 14.8 | 26.5 | 16.7 | 21.4 | 25.2 | 12.7 | 33.1 | 22.3 | 26 | 21.5 | 22.0 | 6.1 | 27.8 |
| 1.5 | 24.2 | 36.9 | 23.2 | 28.5 | 37.2 | 21.3 | 42.4 | 29.2 | 33.7 | 39.2 | 31.6 | 7.3 | 23.2 |
| 2 | 28.6 | 43.4 | 27.3 | 34.6 | 38.5 | 27.6 | 46.2 | 31.3 | 38.5 | 42 | 35.8 | 6.9 | 19.4 |
| 3 | 27.4 | 37.3 | 30.6 | 40.1 | 41.7 | 30.9 | 52 | 36.5 | 42.9 | 60.1 | 40.0 | 10.0 | 25.2 |
| 4 | 27.1 | 44.1 | 33.5 | 48.7 | 45.2 | 34.7 | 49.1 | 40.7 | 42.4 | 53.2 | 41.9 | 8.1 | 19.2 |
| 5 | 35.1 | 53 | 40.2 | 43.4 | 46.5 | 42.4 | 58.1 | 47 | 52.1 | 68.7 | 48.7 | 9.7 | 20.0 |
| 6 | 33.8 | 58.5 | 40.2 | 46.5 | 43.5 | 37.5 | 56.2 | 40 | 51 | 63 | 47.0 | 9.8 | 20.8 |
| 7 | 37.2 | 50.7 | 31.2 | 41.4 | 44.9 | 42 | 57.8 | 43.6 | 51.6 | 65.7 | 46.6 | 10.1 | 21.7 |
| 8 | 35.9 | 54.3 | 34.9 | 45 | 45 | 36 | 58.7 | 41.8 | 53.9 | 59.2 | 46.5 | 9.5 | 20.4 |
| 10 | 33.1 | 49.1 | 34.3 | 35.5 | 45 | 37 | 51.4 | 38.9 | 46.3 | 60.1 | 43.1 | 8.8 | 20.4 |
| 12 | 34 | 51 | 28.6 | 34.1 | 40.8 | 32.6 | 51.6 | 37.7 | 38.1 | 50.9 | 39.9 | 8.4 | 21.1 |
| 16 | 30.2 | 40.8 | 25.2 | 28 | 33 | 25.8 | 41 | 26.8 | 29.6 | 44.9 | 32.5 | 7.1 | 22.0 |
| 24 | 20.5 | 27.8 | 18.2 | 19.5 | 17.1 | 17.8 | 22.5 | 19.1 | 15.5 | 27.3 | 20.5 | 4.2 | 20.3 |
| 48 | 3.83 | 6.89 | 3.7 | 5.11 | 2.56 | 4.31 | 6.51 | 4.43 | 2.77 | 5.47 | 4.6 | 1.4 | 31.8 |
| 72 | 0.715 | 1.63 | 1 | 1.7 | 0 | 0.622 | 1.29 | 1.22 | 0 | 1.31 | 0.9 | 0.6 | 64.0 |
| Parameter | | | | | | | | | | | | | |
| $AUC_{0-12h}$ (ng · h/mL) | 356.2 | 539.8 | 366.4 | 444.3 | 480.8 | 387.0 | 591.4 | 436.5 | 512.8 | 634.2 | 474.9 | 94.7 | 19.9 |
| $AUC_{last}$ (ng · h/mL) | 1033 | 1517 | 966 | 1135 | 1065 | 1003 | 1473 | 1100 | 1048 | 1589 | 1193 | 236 | 19.8 |
| $AUC_{inf}$ (ng · h/mL) | 1043 | 1544 | 983.5 | 1168 | 1097 | 1013 | 1495 | 1121 | 1085 | 1610 | 1216 | 238 | 19.5 |
| $C_{max}$ (ng/mL) | 37.2 | 58.5 | 40.2 | 48.7 | 46.5 | 42.4 | 58.7 | 47 | 53.9 | 68.7 | 50.18 | 9.74 | 19.4 |
| $T_{max}$ (hours) | 7 | 6 | 5 | 4 | 5 | 5 | 8 | 5 | 8 | 5 | 5.80 | 1.40 | 24.1 |
| $T_{1/2}$ (hours) | 9.92 | 11.74 | 12.07 | 13.8 | 8.7 | 10.76 | 11.47 | 12.23 | 9.36 | 10.92 | 11.10 | 1.50 | 13.6 |

TABLE 54

Pharmacokinetic Parameters of Amphetamine Following Oral Administration of L-lysine-d-amphetamine, Adderall XR ® or Dexadrine Spansule ®.

| | Drug | | | | | | | |
|---|---|---|---|---|---|---|---|---|
| Parameter | L-lysine-d-amphetamine 25 mg | Percent[1] | L-lysine-d-amphetamine 75 mg | Percent[1] | Adderall XR ® | Percent[1] | Dexadrine Spansule ® | Percent[1] |
| $AUC_{0-12h}$ (ng · h/mL) | 205.4 | 33.6 | 611.5 | 100 | 637.5 | 104 | 474.9 | 78 |
| $AUC_{last}$ (ng · h/mL) | 396.7 | 31.5 | 1237 | 100 | 1401.1 | 113 | 1193 | 96 |
| $AUC_{inf}$ (ng · h/mL) | 415.0 | 32.9 | 1260 | 100 | 1427 | 113 | 1216 | 97 |
| $C_{max}$ (ng/mL) | 25.0 | 33.8 | 74 | 100 | 73.3 | 99 | 50.2 | 68 |
| $T_{max}$ (hours) | 3.1 | 79.5 | 3.9 | 100 | 5.7 | 146 | 5.8 | 149 |
| $T_{1/2}$ (hours) | 9.68 | 94 | 10.3 | 100 | 10.22 | 99 | 11.1 | 108 |

[1]Percent relative to L-lysine-d-amphetamine 75 mg dose

It will be understood that the specific embodiments of the invention shown and described herein are exemplary only. Numerous variations, changes, substitutions and equivalents will occur to those skilled in the art without departing from the spirit and scope of the invention. In particular, the terms used in this application should be read broadly in light of similar terms used in the related applications. Accordingly, it is intended that all subject matter described herein and shown in the accompanying drawings be regarded as illustrative only and not in a limiting sense and that the scope of the invention be solely determined by the appended claims.

The invention claimed is:

1. A pharmaceutical composition comprising an unprotected prodrug and one or more pharmaceutically acceptable additives;

wherein said prodrug consists of L-lysine-d-amphetamine or a pharmaceutically acceptable salt thereof;

wherein said composition is in a form suitable for oral administration;

wherein said composition provides release of amphetamine as an active from said prodrug following oral administration; and wherein said prodrug has limited bioavailability of amphetamine when administered through alternative routes of administration.

2. The composition of claim 1 wherein said L-lysine-d-amphetamine or pharmaceutically acceptable salt thereof provides a therapeutically effective amount of amphetamine, but a reduced $C_{max}$ of amphetamine as compared to unbound amphetamine.

3. The composition of claim 1 or 2 wherein said L-lysine-d-amphetamine salt is L-lysine-d-amphetamine mesylate.

4. The composition of claim 1 or 2 wherein said L-lysine-d-amphetamine salt is L-lysine-d-amphetamine hydrochloride.

5. The composition of claim 1 or 2, wherein said form suitable for oral administration is a tablet, a capsule, a caplet, an oral solution, or an oral suspension.

6. The composition of claim 3, wherein said form suitable for oral administration is a tablet, a capsule, a caplet, an oral solution, or an oral suspension.

7. The composition of claim 4, wherein said form suitable for oral administration is a tablet, a capsule, a caplet, an oral solution, or an oral suspension.

8. The composition of claim 2, wherein the pharmaceutically acceptable additive comprises diluents, binders and adhesives, lubricants, plasticizers, distintegrants, colorants, bulking substances, flavorings, sweeteners, buffers or adsorbents.

9. The composition of claim 1, wherein said L-lysine-d-amphetamine or pharmaceutically acceptable salt thereof is in an amount sufficient to provide a pharmacologically effective amount to treat a patient in need of amphetamine.

10. The composition of claim 9, wherein said L-lysine-d-amphetamine or pharmaceutically acceptable salt thereof is in an amount sufficient to provide a therapeutically bioequivalent area under the curve (AUC) of amphetamine when compared to amphetamine alone, but in an amount insufficient to provide a $C_{max}$ which results in euphoria.

11. The pharmaceutical composition of claim 1, wherein said L-lysine-d-amphetamine or pharmaceutically acceptable salt thereof is in an amount sufficient to maintain a steady-state serum release curve of amphetamine which provides a therapeutically effective bioavailability of amphetamine but prevents spiking or increased blood serum concentrations compared to unbound amphetamine.

12. The pharmaceutical composition of claim 1, wherein said L-lysine-d-amphetamine or salt thereof provides sustained release characteristics.

13. The pharmaceutical composition of claim 1, wherein said L-lysine-d-amphetamine or pharmaceutically acceptable salt thereof is in an amount sufficient to provide a therapeutically effective amount of amphetamine, but at a reduced rate of absorption of the amphetamine as compared to unbound amphetamine.

14. The pharmaceutical composition of claim 1, wherein the L-lysine-d-amphetamine or pharmaceutically acceptable salt thereof is in an amount exceeding those within the therapeutic range for unbound amphetamine.

15. A pharmaceutical composition comprising an oral dosage form of an unprotected prodrug consisting of L-lysine-d-amphetamine or pharmaceutically acceptable salt thereof and one or more pharmaceutically acceptable additives.

16. The pharmaceutical composition of claim 15 wherein said prodrug provides an increased rate of clearance of amphetamine when given at doses exceeding those within the therapeutic range of unbound amphetamine.

17. The pharmaceutical composition of claim 15 wherein said prodrug exhibits a reduced rate of absorption of amphetamine as compared to unbound amphetamine when administered at doses exceeding those within the therapeutic range of unbound amphetamine.

18. An oral pharmaceutical dosage form for the administration of amphetamine comprising an unprotected prodrug and one or more pharmaceutically acceptable additives;

wherein said prodrug consists of L-lysine-d-amphetamine or a pharmaceutically acceptable salt thereof;

wherein said composition provides limited release of amphetamine as an active from said prodrug following oral administration; and wherein said prodrug has limited bioavailability of amphetamine when administered through alternative routes of administration.

* * * * *